US010219823B2

(12) United States Patent
Yoshimine

(10) Patent No.: US 10,219,823 B2
(45) Date of Patent: Mar. 5, 2019

(54) ULTRASONIC PROBE

(71) Applicant: OLYMPUS CORPORATION, Hachioji-shi, Tokyo (JP)

(72) Inventor: Hideto Yoshimine, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 202 days.

(21) Appl. No.: 15/284,260

(22) Filed: Oct. 3, 2016

(65) Prior Publication Data

US 2017/0020552 A1 Jan. 26, 2017

Related U.S. Application Data

(63) Continuation of application No. PCT/JP2015/076184, filed on Sep. 15, 2015.

(30) Foreign Application Priority Data

Jan. 7, 2015 (JP) .................................. 2015-001839
Jan. 7, 2015 (JP) .................................. 2015-001840

(51) Int. Cl.
*A61B 17/32* (2006.01)
*A61B 17/56* (2006.01)
(Continued)

(52) U.S. Cl.
CPC .. *A61B 17/320068* (2013.01); *A61B 17/1613* (2013.01); *A61B 17/1684* (2013.01);
(Continued)

(58) Field of Classification Search
CPC ............ A61B 17/22004; A61B 17/225; A61B 17/320068; A61B 17/320092;
(Continued)

(56) References Cited

U.S. PATENT DOCUMENTS

2006/0235305 A1* 10/2006 Cotter ................ A61B 17/1604
600/459
2007/0106158 A1 5/2007 Madan et al.
(Continued)

FOREIGN PATENT DOCUMENTS

CN 101500492 A 8/2009
CN 102176874 A 9/2011
(Continued)

OTHER PUBLICATIONS

Jul. 11, 2017 International Preliminary Report on Patentability issued in International Patent Application No. PCT/JP2015/076184.
(Continued)

*Primary Examiner* — Melanie R Tyson
(74) *Attorney, Agent, or Firm* — Oliff PLC

(57) ABSTRACT

In an ultrasonic probe a tapered section in which a sectional area perpendicular to a longitudinal axis decreases from a proximal side toward a distal side is provided on the distal side with respect to a probe main body section. When the probe main body section and the tapered section vibrate in an established frequency range, a most distal vibration node positioned most distally among vibration nodes is positioned on the proximal side with respect to a proximal end of the tapered section, and a ⅛ wavelength of the vibration is smaller than a taper dimension from the proximal end the tapered section to a distal end of the tapered section in a longitudinal axis direction.

8 Claims, 18 Drawing Sheets

(51) Int. Cl.
*A61B 18/00* (2006.01)
*A61B 17/16* (2006.01)
*A61B 17/3211* (2006.01)

(52) U.S. Cl.
CPC .......... *A61B 17/3211* (2013.01); *A61B 17/56* (2013.01); *A61B 18/00* (2013.01); *A61B 17/1659* (2013.01); *A61B 2017/320072* (2013.01)

(58) Field of Classification Search
CPC ....... A61B 2017/320094; A61B 2017/320069; A61B 2017/320072; A61B 2017/320082; A61B 2017/320089; A61B 2017/320073; A61B 2017/320074; A61B 2017/320098; A61F 9/00745
USPC .......................................................... 606/169
See application file for complete search history.

(56) References Cited

U.S. PATENT DOCUMENTS

| | | | |
|---|---|---|---|
| 2007/0282332 A1 | 12/2007 | Witt et al. | |
| 2010/0106173 A1* | 4/2010 | Yoshimine | A61B 17/320068 606/169 |
| 2013/0040261 A1 | 2/2013 | Kwon et al. | |

FOREIGN PATENT DOCUMENTS

| | | |
|---|---|---|
| CN | 102843989 A | 12/2012 |
| CN | 103120596 A | 5/2013 |
| CN | 104027156 A | 9/2014 |
| JP | H07-255736 A | 10/1995 |
| JP | 2002-143177 A | 5/2002 |
| JP | 2005-152098 A | 6/2005 |
| JP | 2007-054665 A | 3/2007 |
| JP | 2012-501735 A | 1/2012 |
| JP | 2014-054545 A | 3/2014 |
| WO | 01/35812 A2 | 5/2001 |
| WO | 2010/047395 A1 | 4/2010 |

OTHER PUBLICATIONS

Dec. 28, 2015 International Search Report issued in International Patent Application No. PCT/JP2015/076184.
Mar. 20, 2018 Office Action issued in Chinese Patent Application No. 201580014004.8.
Aug. 17, 2018 Extended European Search Report issued in European Patent Application No. 15876924.0.
Nov. 28, 2018 Office Action issued in Chinese Patent Application No. 201580014004.8.

* cited by examiner

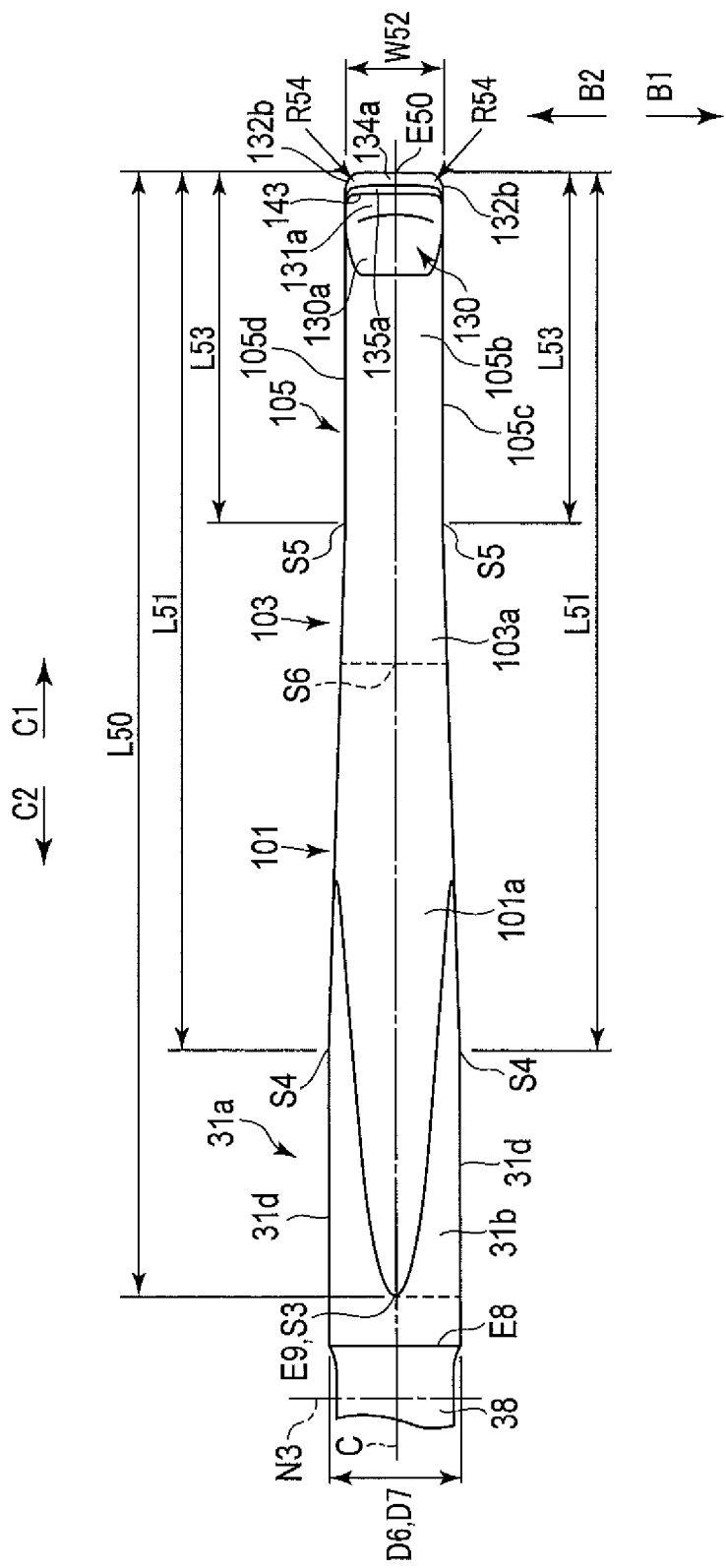
F I G. 4

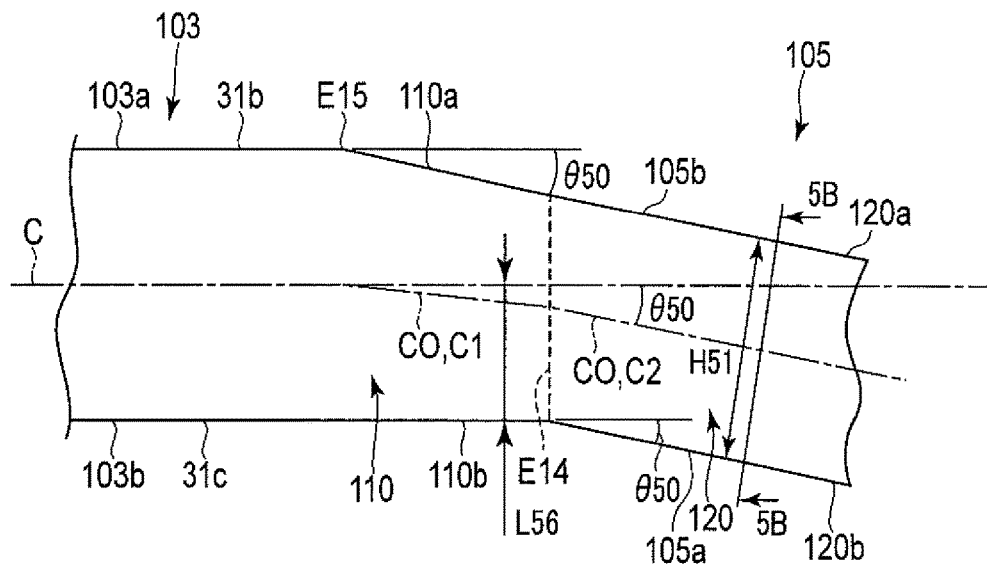
F I G. 5A
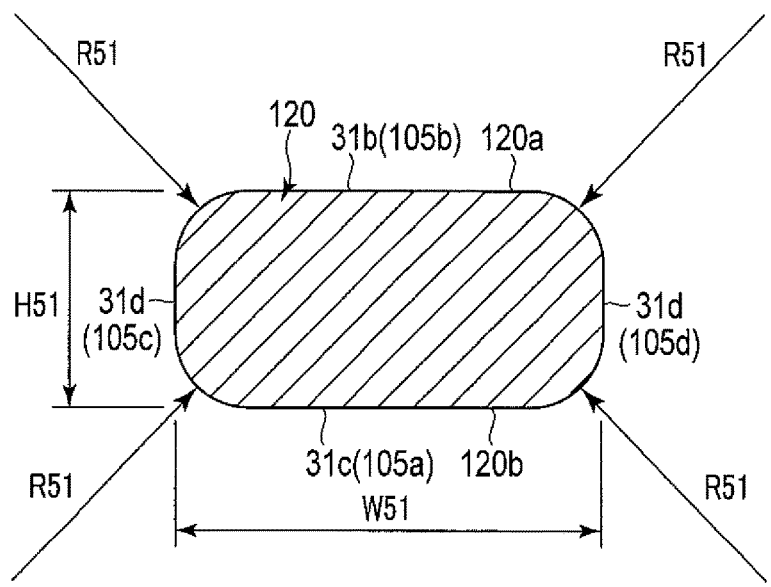
F I G. 5B

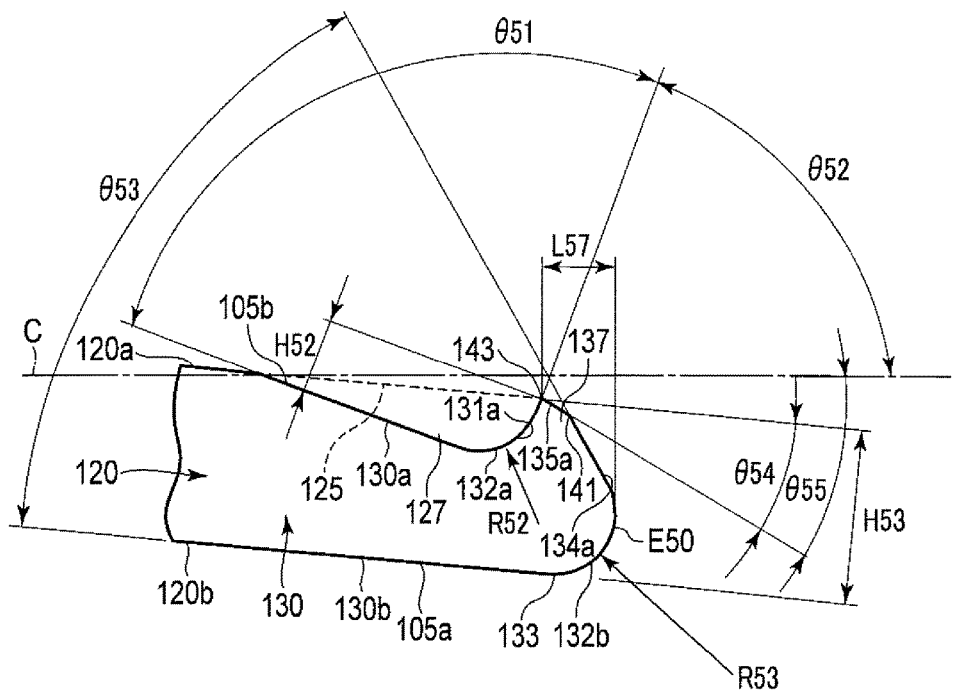
F I G. 6
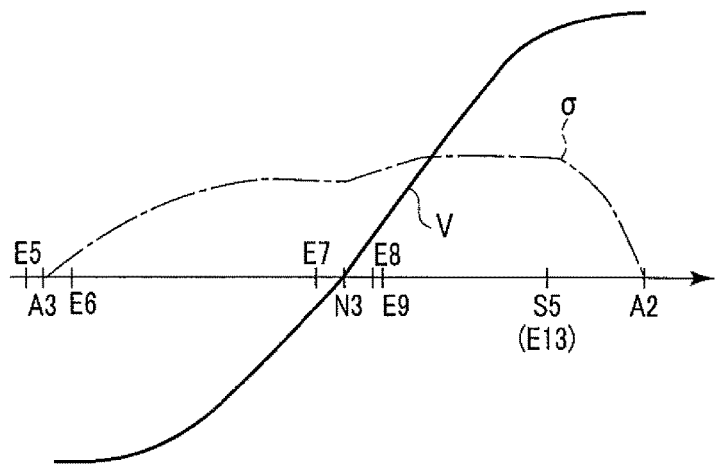
F I G. 7

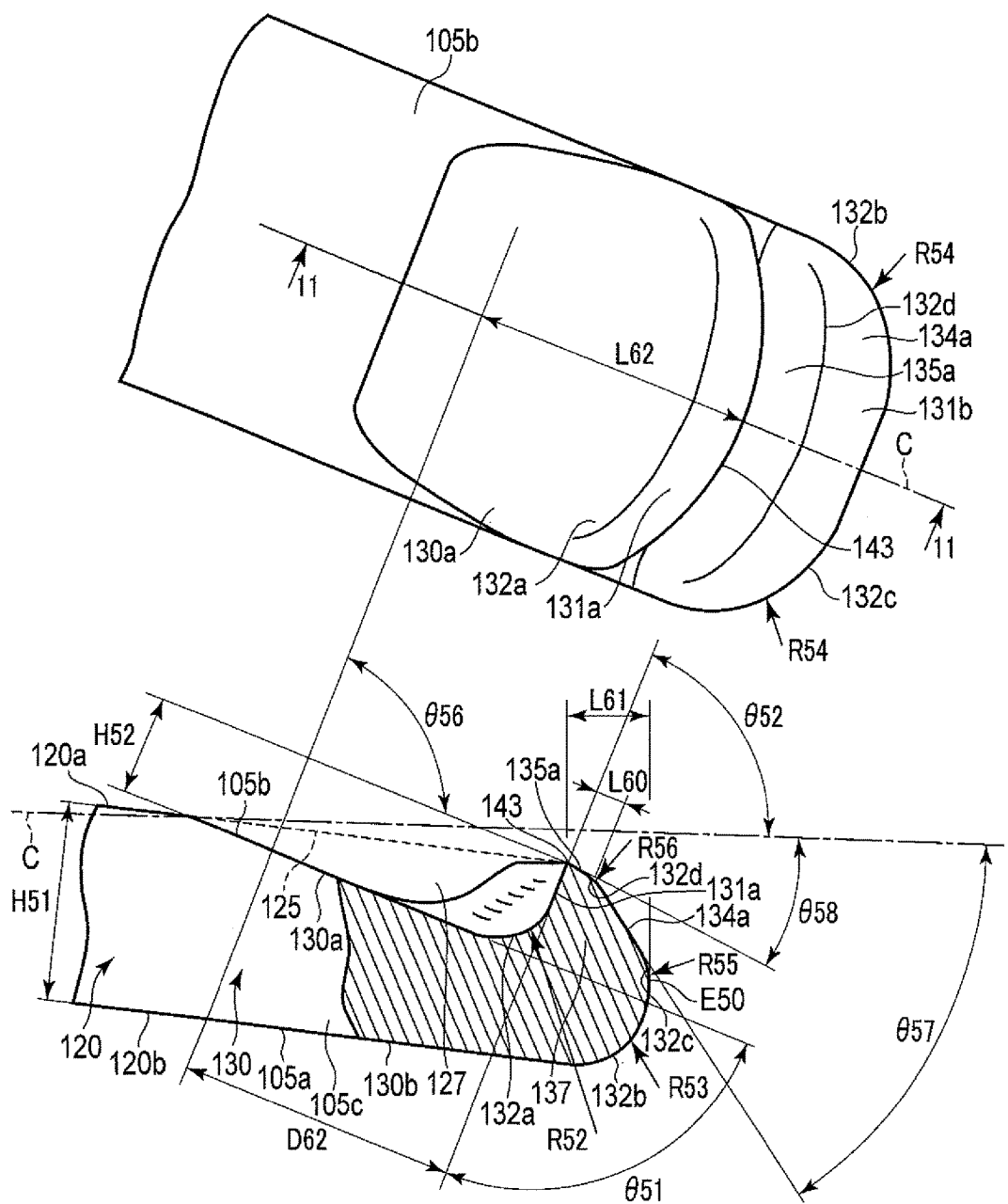
F I G. 11

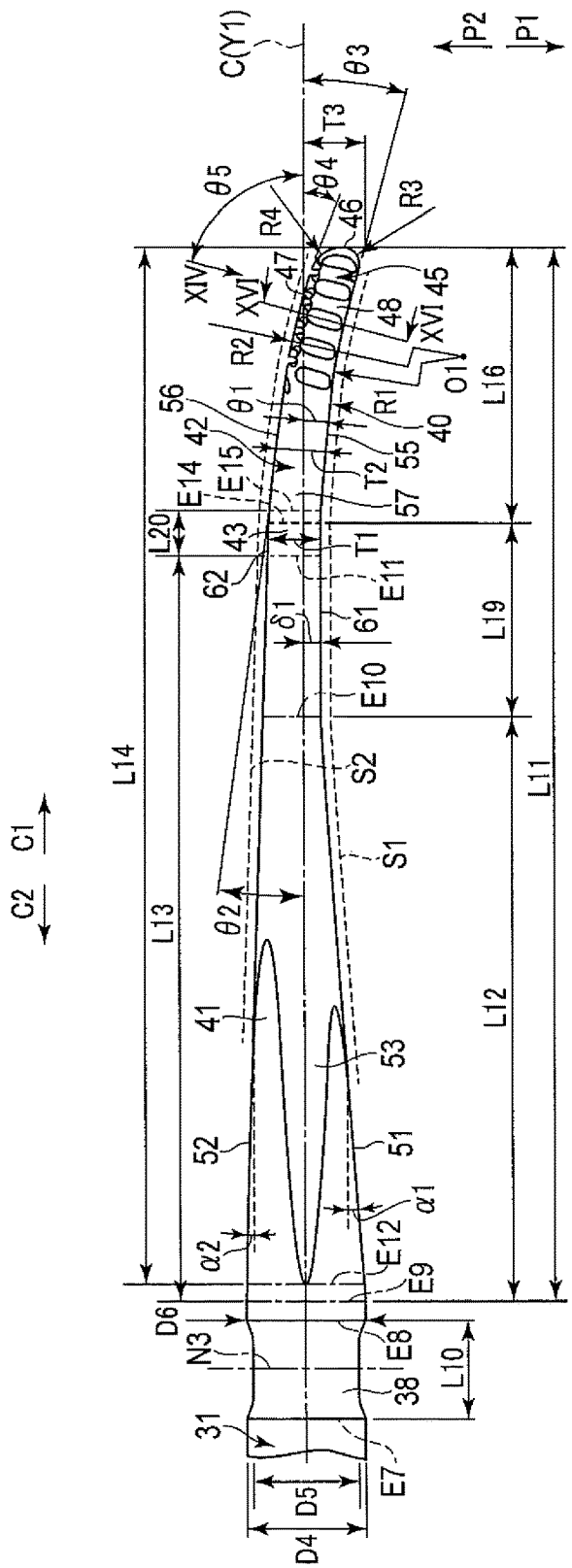
F I G. 12

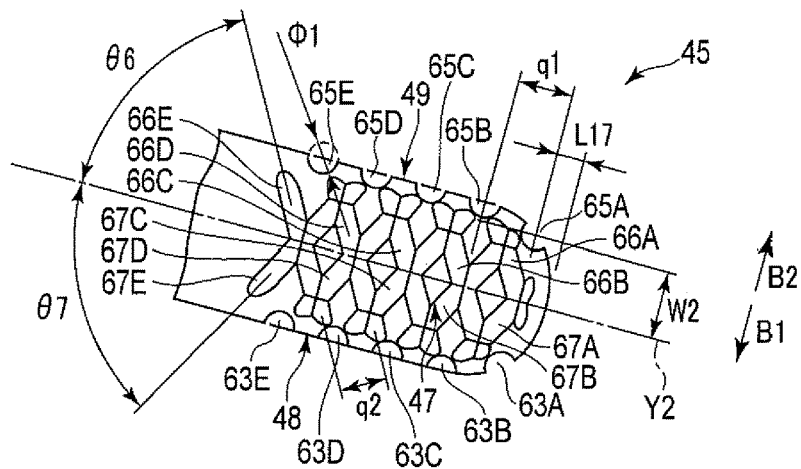
F I G. 14
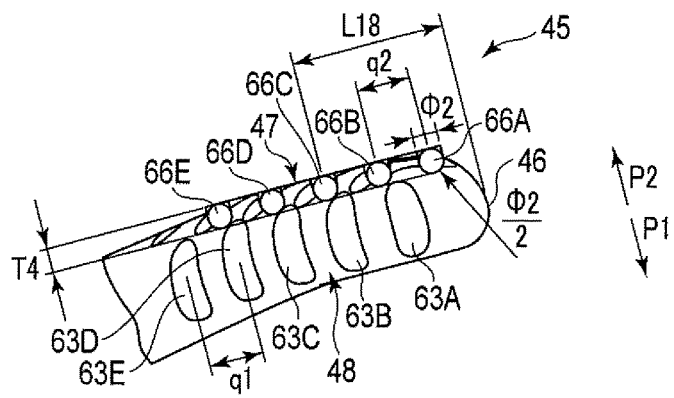
F I G. 15
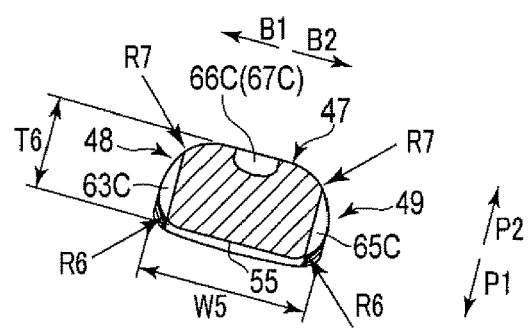
F I G. 16

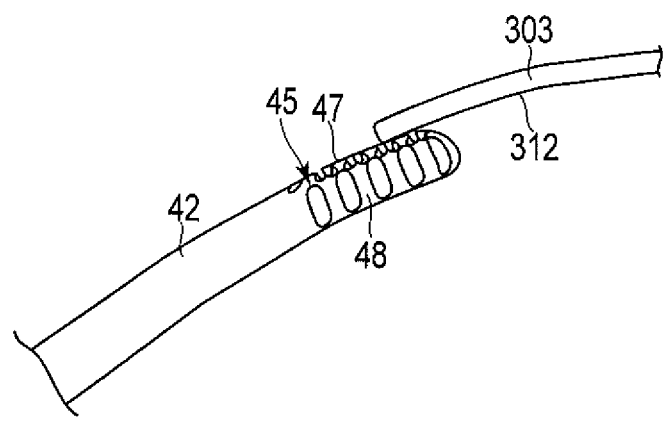
F I G. 19
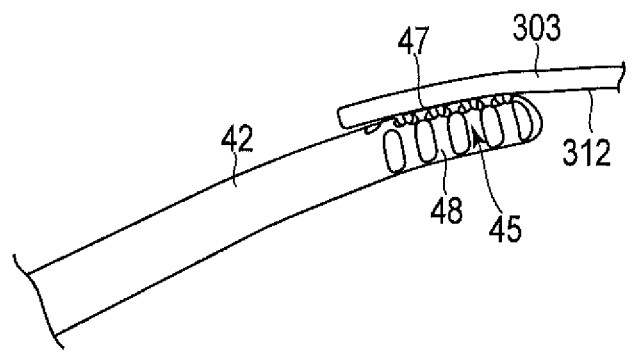
F I G. 20

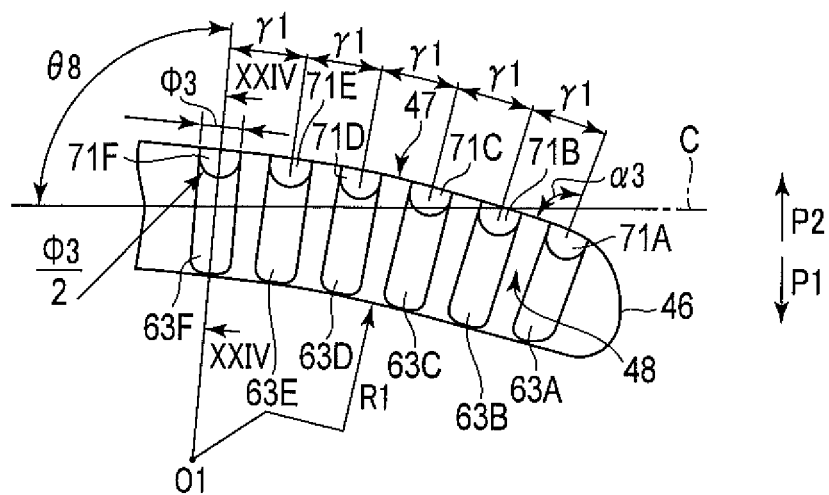
F I G. 23
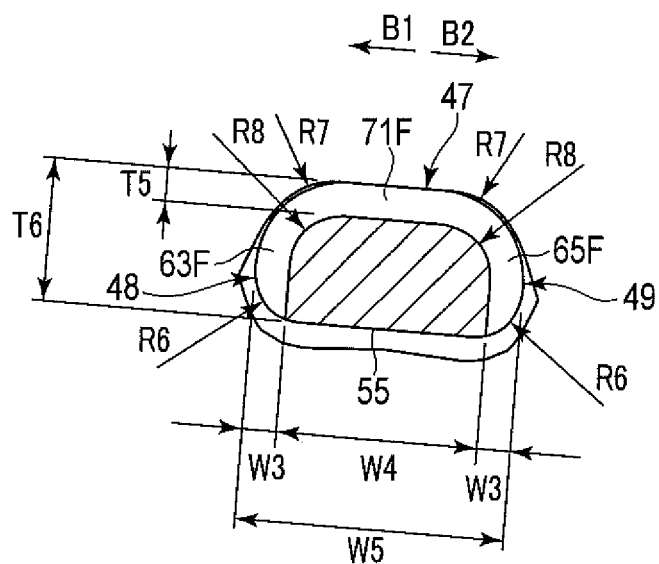
F I G. 24

ULTRASONIC PROBE

CROSS-REFERENCE TO RELATED APPLICATIONS

This is a Continuation Application of PCT Application No. PCT/JP2015/076184, filed Sep. 15, 2015 and based upon and claiming the benefit of priority from prior Japanese Patent Applications No. 2015-001840, filed Jan. 7, 2015; and No. 2015-001839 filed Jan. 7, 2015, the entire contents of both of which are incorporated herein by reference.

BACKGROUND OF THE INVENTION

1. Field of the Invention

The present invention relates to an ultrasonic probe to perform cutting of, for example, a hard bone tissue and a cartilage tissue by ultrasonic vibration.

2. Description of the Related Art

In Jpn. Pat. Appln. KOKAI Publication No. 2005-152098, there is disclosed an ultrasonic treatment device including an ultrasonic probe (an ultrasonic horn). In this ultrasonic treatment device, an ultrasonic vibration generated in a vibration generating section (an ultrasonic vibration mechanism) is transmitted from a proximal side toward a distal side in the ultrasonic probe. In a distal portion of the ultrasonic probe, a scalpel portion is formed as a treating surface. In the scalpel portion, an outer surface of the ultrasonic probe is formed in an uneven state. The ultrasonic vibration is transmitted to the scalpel portion in a state where the scalpel portion is in contact with a treated target, whereby the treated target (e.g., a bone or another hard tissue) is cut.

BRIEF SUMMARY OF THE INVENTION

According to one aspect of the invention, an ultrasonic probe includes that: a probe main body section which is extended along a longitudinal axis, and which is configured to vibrate in an established frequency range in a state where an ultrasonic vibration is transmitted from a proximal side toward a distal side; and a tapered section which is provided on the distal side with respect to the probe main body section, and in which a sectional area perpendicular to the longitudinal axis decreases from the proximal side toward the distal side, the tapered section being configured to vibrate together with the probe main body section in the established frequency range in a state where the ultrasonic vibration is transmitted from the probe main body section, wherein in the state where the probe main body section and the tapered section vibrate in the established frequency range, a most distal vibration node positioned most distally among vibration nodes is positioned on the proximal side with respect to a proximal end of the tapered section, and a ⅛ wavelength of the vibration is smaller than a taper dimension from the proximal end of the tapered section to a distal end of the tapered section in a longitudinal axis direction.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a schematic view of the distal portion of the ultrasonic probe according to the first embodiment seen from a second intersecting direction side;

FIG. 5A is an enlarged schematic view of a sectional area decreasing portion and its periphery in a curving section of the ultrasonic probe according to the first embodiment;

FIG. 5B is a cross-sectional view along the 5B-5B line of FIG. 5A;

FIG. 6 is an enlarged schematic view of a treating section and its periphery in the curving section of the ultrasonic probe according to the first embodiment;

FIG. 7 is a schematic view showing an amplitude of a longitudinal vibration and stress due to an ultrasonic vibration between a second distal vibration antinode and a most distal vibration antinode in a state where the vibrating body unit according to the first embodiment longitudinally vibrates in an established frequency range;

FIG. 11 shows an enlarged schematic view of a treating section and its periphery in a curving section of the ultrasonic probe according to the second embodiment, and a cross-sectional view along the 11-11 line;

FIG. 12 is a schematic view of a distal portion of an ultrasonic probe according to a third embodiment seen from a first width direction side;

FIG. 14 is a schematic view of a second curved extending section according to the third embodiment seen from a direction of an arrow XIV of FIG. 12;

FIG. 15 is a schematic view of the second curved extending section according to the third embodiment seen from a first width direction side;

FIG. 16 is a cross-sectional view along the XVI-XVI line of FIG. 12;

FIG. 19 is a schematic view showing a state where a first cutting surface of a curved extending section of the ultrasonic probe according to the third embodiment is in contact with a lower surface of an acromion;

FIG. 20 is a schematic view showing a state where the first cutting surface of the curved extending section of the ultrasonic probe according to the third embodiment is in contact with a position different from that of FIG. 19 in the lower surface of the acromion;

FIG. 23 is a schematic view of a second curved extending section according to the fourth embodiment seen from a first width direction side; and FIG. 24 is a cross-sectional view along the XXIV-XXIV line of FIG. 23.

DETAILED DESCRIPTION OF THE INVENTION

First Embodiment

Figure 1:
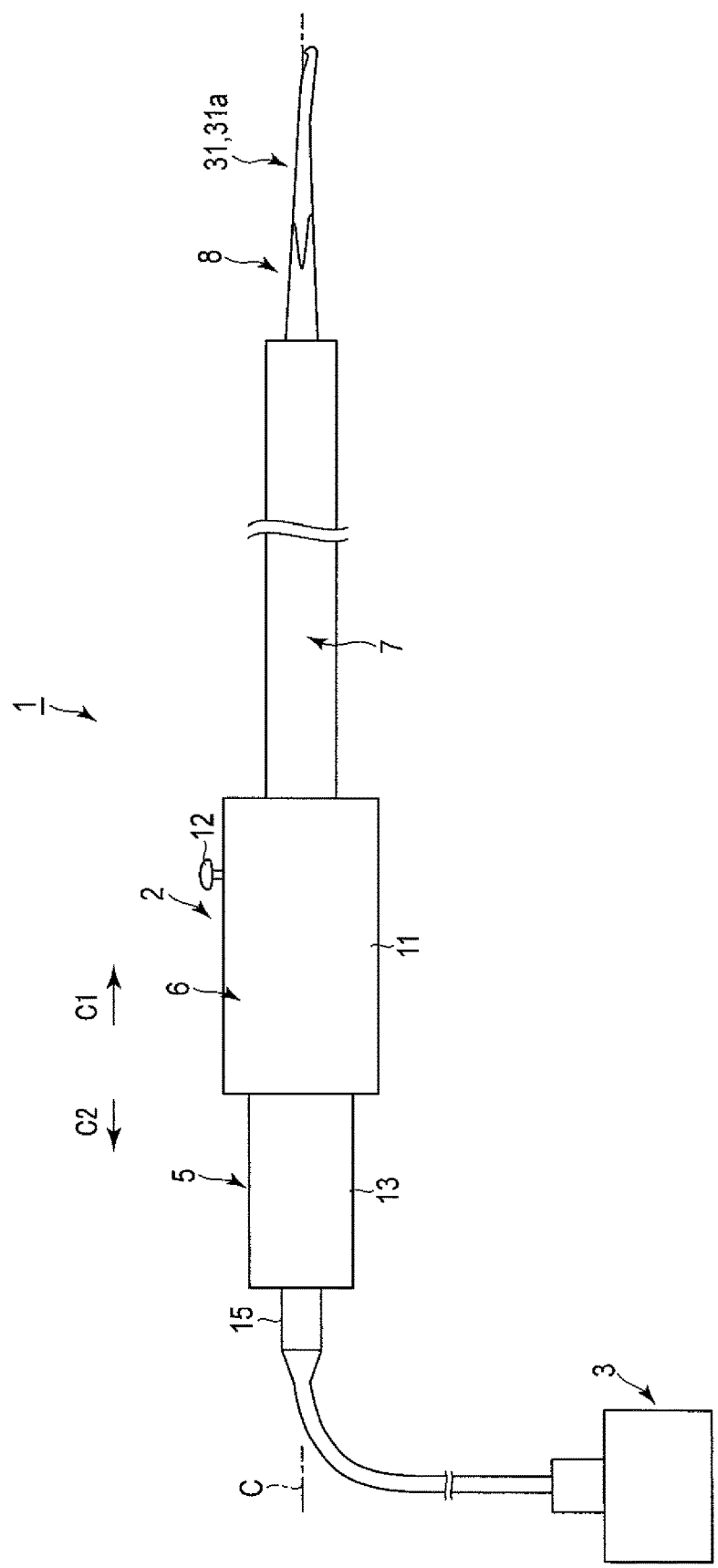
FIG. 1 is a view showing an ultrasonic treatment device according to a first embodiment of the present invention.

A first embodiment of the present invention will be described with reference to FIG. 1 to FIG. 10. FIG. 1 is a view showing an ultrasonic treatment system 1 of the present embodiment. As shown in FIG. 1, the ultrasonic treatment system 1 includes an ultrasonic treatment instrument (a hand piece) 2, an energy control device 3, and a transducer unit 5. The ultrasonic treatment instrument 2 has a longitudinal axis C. Here, a direction parallel to the longitudinal axis C is a longitudinal axis direction. One side of the longitudinal axis direction is a distal side (an arrow C1 side of FIG. 1), and a side opposite to the distal side is a proximal side (an arrow C2 side of FIG. 1).

The ultrasonic treatment tool 2 includes a holding unit 6, a sheath 7, and an ultrasonic probe 8. The holding unit 6 includes a holding casing 11 to be held by an operator, and an energy operating button 12 that is an energy operation input section attached to the holding casing 11 and configured to be operated by the operator. The sheath 7 that is a hollow tubular member extending along the longitudinal axis C is coupled with the distal side of the holding unit 6. The ultrasonic probe (a vibration transmitting member) 8 is inserted through the sheath 7. It is to be noted that a distal portion of the ultrasonic probe 8 projects from a distal end of the sheath 7 toward the distal side.

Furthermore, the transducer unit 5 having a transducer case 13 is coupled with the proximal side of the holding unit 6. The oscillator unit 5 is connected to one end of a cable 15. The other end of the cable 15 is connected to the energy control device 3. The energy control device 3 includes an electric power source, a conversion circuit to convert an electric power from the electric power source into a vibration generating electric power, a processor (a control section) including a CPU (central processing unit) or an ASIC (application specific integrated circuit), and a storage medium such as a memory. Inside the holding casing 11, there is disposed a switch (not shown) in which an ON/OFF state is changed by an input of an energy operation in the energy operating button 12. The switch is electrically connected to the processor of the energy control device 3 via a signal route extending through the vibrator unit 5 and an inside of the cable 15. Furthermore, in the ultrasonic treatment system 1, a vibrating body unit 20 extends through an inside of the holding casing 11 and an inside of the transducer case 13.

Figure 2:
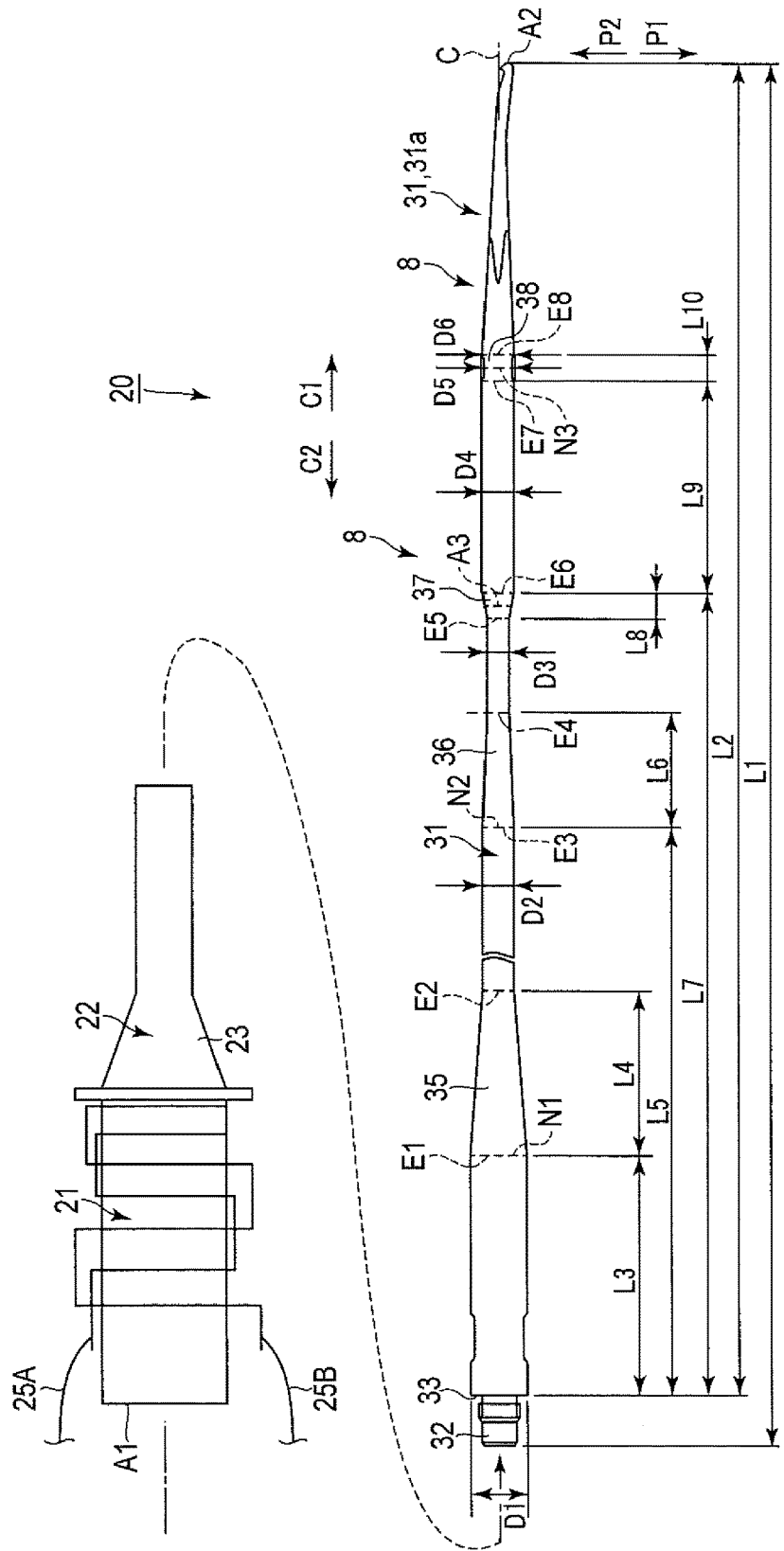
FIG. 2 is a schematic view of a vibrating body unit according to the first embodiment seen from a first width direction side.

FIG. 2 is a view showing a constitution of the vibrating body unit 20. As shown in FIG. 2, the vibrating body unit 20 includes the ultrasonic probe 8 mentioned above, an ultrasonic transducer 21 that is a vibration generating section constituted of piezoelectric elements, and a relay transmitting member 22. The ultrasonic oscillator 21 and the relay transmitting member 22 are arranged in the oscillator case 13, and the relay transmitting member 22 is supported by the transducer case 13. The ultrasonic transducer 21 is attached to the relay transmitting member 22. Inside the holding casing 11, the ultrasonic probe 8 is connected to the distal side of the relay transmitting member 22. In the relay transmitting member 22, a sectional area changing portion 23 is disposed in which a sectional area perpendicular to the longitudinal axis C decreases toward the distal side. The sectional area changing portion (a horn portion) 23 is positioned on the distal side with respect to the ultrasonic transducer 21. The ultrasonic transducer 21 is connected to one end of each of electric wires 25A and 25B. The electric wires 25A and 25B extend through the inside of the cable 15, and the other end of the wire is connected to the energy control device 3.

The switch is switched to an ON state by the input of the energy operation in the energy operating button 12, whereby in the energy control device 3, the control section controls the conversion circuit, to supply the vibration generating electric power (a vibration generating current) to the ultrasonic vibrator 21 through the electric wires 25A and 25B. Consequently, in the ultrasonic transducer 21, an ultrasonic vibration occurs, and the generated ultrasonic vibration is transmitted to the ultrasonic probe 8 via the relay transmitting member 22. In this case, an amplitude of the ultrasonic vibration is enlarged in the sectional area changing portion 23 of the relay transmitting member 22.

The ultrasonic probe 8 includes a probe main body section 31 extending along the longitudinal axis C. The probe main body section 31 substantially linearly extends along the longitudinal axis C which is an axial center. On the proximal side of the probe main body section 31, an engagement connecting portion 32 is provided. The engagement connecting portion 32 is engaged in an engagement groove (not shown) disposed in the relay transmitting member 22 (e.g., by screwing an external thread into an internal thread), whereby the probe main body section 31 is connected to the distal side of the relay transmitting member 22. Thus, the relay transmitting member 22 is connected to the probe main body section 31, whereby an abutment surface 33 formed at a proximal end of the probe main body section 31 abuts on the relay transmitting member 22. The ultrasonic vibration is transmitted from the relay transmitting member 22 to the probe main body section 31 through the abutment surface 33.

Thus, the ultrasonic vibration is transmitted to the probe main body section 31, whereby in the probe main body section 31 (the ultrasonic probe 8), the ultrasonic vibration is transmitted from the proximal side toward the distal side. In a state where the ultrasonic vibration is transmitted through the probe main body section 31, the vibrating body unit 20 performs a longitudinal vibration in a vibrating direction parallel to the longitudinal axis direction in an established frequency range including an established frequency. In this case, a vibration antinode (the most proximal vibration antinode) A1 that is one of vibration antinodes of the longitudinal vibration is positioned at a proximal end of the vibrating body unit 20 (a proximal end of the relay transmitting member 22), and a vibration antinode (the most distal vibration antinode) A2 that is one of the vibration antinodes of the longitudinal vibration is positioned at a distal end of the vibrating body unit 20 (a distal end of the ultrasonic probe 8). Here, the vibration antinode A1 is positioned most proximally among the vibration antinodes of the longitudinal vibration, and the vibration antinode A2 is positioned most distally among the vibration antinodes of the longitudinal vibration. In a certain example, the vibrating body unit 20 is designed in a state of transmitting the ultrasonic vibration therethrough, thereby performing the longitudinal vibration at 47 kHz (the established frequency), and the vibrating body unit actually longitudinally vibrates in the frequency range (the established frequency range) of 46 kHz or more and 48 kHz or less.

The ultrasonic probe 8 has a total length L1 from its distal end to its proximal end (a proximal end of the engagement connecting portion 32) in the longitudinal axis direction. In the certain example, it is preferable that the total length L1 is 183.1 mm. Furthermore, the ultrasonic probe 8 has a longitudinal dimension L2 from the distal end to the abutment surface 33 (the proximal end of the probe main body section 31) in the longitudinal axis direction. In the certain example, it is preferable that the longitudinal dimension L2 is 177.1 mm.

In the probe main body section 31, a horn portion (a first horn portion) 35 is disposed. In the horn portion 35, the sectional area perpendicular to the longitudinal axis C decreases toward the distal side. The horn portion (a sectional area decreasing portion) 35 is positioned on the distal side with respect to the abutment surface 33, and the probe main body section 31 has a longitudinal dimension L3 from the abutment surface 33 to a proximal end (a vibration input end) E1 of the horn portion 35 in the longitudinal axis direction. In the certain example, it is preferable that the longitudinal dimension L3 is 29 mm. Furthermore, the horn portion (the first horn portion) 35 has a horn longitudinal dimension (a first horn longitudinal dimension) L4 from the proximal end (the vibration input end) E1 to a distal end (a vibration output end) E2 in the longitudinal axis direction. In the certain example, it is preferable that the horn longitudinal dimension L4 is 20 mm.

An outer diameter of the probe main body section 31 is kept to be substantially constant from the abutment surface 33 to the proximal end E1 of the horn portion 35 in the longitudinal axis direction. Therefore, the probe main body section 31 has an outer diameter D1 in the abutment surface 33 and at the proximal end E1 of the horn portion 35. In the certain example, it is preferable that the outer diameter D1 is 7 mm. Furthermore, in the horn portion 35, a sectional area decreases toward the distal side, and hence at the distal end E2 of the horn portion 35, the probe main body section 31 has an outer diameter D2 smaller than the outer diameter D1. That is, in the horn portion 35, the outer diameter of the probe main body section 31 decreases from the outer diameter D1 to the outer diameter D2 toward the distal side. In the certain example, it is preferable that the outer diameter D2 is 3.8 mm.

In a state where the vibrating body unit 20 longitudinally vibrates in the predetermined frequency range (e.g., 46 kHz or more and 48 kHz or less), a vibration node N1 that is one of vibration nodes of the longitudinal vibration is positioned at the proximal end E1 of the horn portion 35 or in the vicinity of the proximal end E1, and each of the vibration antinodes of the longitudinal vibration is positioned away from the horn portion 35 in the longitudinal axis direction. Consequently, in the horn portion 35 in which the sectional area decreases toward the distal side, the amplitude of the longitudinal vibration (the ultrasonic vibration) is enlarged. In the certain example, the longitudinal vibration in which the amplitude at the vibration antinode is 18 μm is transmitted to the proximal end E1 of the horn portion 35, and the amplitude of the longitudinal vibration in the horn portion 35 is enlarged. It is to be noted that in a state where the vibrating body unit 20 longitudinally vibrates at the predetermined frequency (e.g., 47 kHz) included in the predetermined frequency range, the vibration node N1 is positioned at the proximal end E1 of the horn portion 35.

In the probe main body section 31, a horn portion (a second horn portion) 36 is provided. In the horn portion 36, the sectional area perpendicular to the longitudinal axis C decreases toward the distal side. The horn portion (a sectional area decreasing portion) 36 is positioned on the distal side from the horn portion (the first horn portion) 35, and the probe main body section 31 has a longitudinal dimension L5 from the abutment surface 33 to a proximal end (a vibration input end) E3 of the horn portion 36 in the longitudinal axis direction. In the certain example, it is preferable that the longitudinal dimension L5 is 88.1 mm. Furthermore, the horn portion (the second horn portion) 36 has a horn longitudinal dimension (a second horn longitudinal dimension) L6 from the proximal end (the vibration input end) E3 to a distal end (a vibration output end) E4 in the longitudinal axis direction. In the certain example, it is preferable that the horn longitudinal dimension L6 is 14 mm.

In the probe main body section 31, the outer diameter is kept to be substantially constant from the distal end E2 of the horn portion (the first horn portion) 35 to the proximal end E3 of the horn portion (the second horn portion) 36 in the longitudinal axis direction. Therefore, the probe main body section 31 has the outer diameter D2 at the proximal end E3 of the horn portion 36. That is, at the distal end E2 of the horn portion 35 and the proximal end E3 of the horn portion 36, the outer diameter of the probe main body section 31 becomes the outer diameter D2 and has about the same size. Furthermore, in the horn portion 36, the sectional area decreases toward the distal side, and hence at the distal end E4 of the horn portion 36, the probe main body section 31 has an outer diameter D3 that is smaller than the outer diameter D2. That is, in the horn portion 36, the outer diameter of the probe main body section 31 decreases from the outer diameter D2 to the outer diameter D3 toward the distal side. In the certain example, it is preferable that the outer diameter D3 is 2.7 mm.

In the state where the vibrating body unit 20 longitudinally vibrates in the established frequency range (e.g., 46 kHz or more and 48 kHz or less), a vibration node N2 that is one of the vibration nodes of the longitudinal vibration is positioned at the proximal end E3 of the horn portion 36 or in the vicinity of the proximal end E3, and each of the vibration antinodes of the longitudinal vibration is positioned away from the horn portion 36 in the longitudinal axis direction. Consequently, in the horn portion 36 in which the sectional area decreases toward the distal side, the amplitude of the longitudinal vibration (the ultrasonic vibration) is enlarged. It is to be noted that in the state where the vibrating body unit 20 longitudinally vibrates at the established frequency (e.g., 47 kHz) included in the established frequency range, the vibration node N2 is positioned at the proximal end E3 of the horn portion 36. Furthermore, in the state where the vibrating body unit 20 longitudinally vibrates in the predetermined frequency range, the vibration node N2 is positioned on the distal side with respect to the vibration node N1.

In the probe main body section 31, a sectional area increasing portion 37 is provided. In the sectional area increasing portion 37, the sectional area perpendicular to the longitudinal axis C increases toward the distal side. The sectional area increasing portion 37 is positioned on the distal side with respect to the horn portion (the second horn portion) 36, and the probe main body section 31 has a longitudinal dimension L7 from the abutment surface 33 to a distal end (a vibration output end) E6 of the sectional area increasing portion 37 in the longitudinal axis direction. In the certain example, it is preferable that the longitudinal dimension L7 is 116.7 mm. Furthermore, the sectional area increasing portion 37 has an extending dimension L8 from a proximal end (a vibration input end) E5 to the distal end (the vibration output end) E6 in the longitudinal axis direction. The extending dimension L8 is small, and hence in the sectional area increasing portion 37, a distance from the proximal end E5 to the distal end E6 decreases.

In the probe main body section 31, the outer diameter is kept to be substantially constant from the distal end E4 of the horn portion (the second horn portion) 36 to the proximal end E5 of the sectional area increasing portion 37 in the longitudinal axis direction. Therefore, the probe main body section 31 has the outer diameter D3 at the proximal end E5 of the sectional area increasing portion 37. That is, at the distal end E4 of the horn portion 36 and the proximal end E5 of the sectional area increasing portion 37, the outer diameter of the probe main body section 31 becomes the outer diameter D3 and has about the same size. Furthermore, in the sectional area increasing portion 37, the sectional area increases toward the distal side, and hence at the distal end E6 of the sectional area increasing portion 37, the probe main body section 31 has an outer diameter D4 that is larger than the outer diameter D3. That is, in the sectional area increasing portion 37, the outer diameter of the probe main body section 31 increases from the outer diameter D3 to the outer diameter D4 toward the distal side. In the certain example, the outer diameter D4 is about the same as the outer diameter D2 at the proximal end E3 of the horn portion 36. In this case, it is preferable that the outer diameter D4 is 3.8 mm.

In the state where the vibrating body unit 20 longitudinally vibrates in the established frequency range, a vibration antinode A3 that is one of the vibration antinodes of the longitudinal vibration is positioned in the sectional area increasing portion 37. The vibration antinode A3 at which stress due to the ultrasonic vibration becomes zero is positioned in the sectional area increasing portion 37, and hence, also in the sectional area increasing portion 37 in which the sectional area increases toward the distal side, the amplitude of the longitudinal vibration (the ultrasonic vibration) hardly decreases. It is to be noted that in the state where the vibrating body unit 20 longitudinally vibrates in the established frequency range, the vibration antinode A3 is positioned on the distal side with respect to the vibration node N2, and in the present embodiment, the vibration antinode A3 is positioned second distally among the vibration antinodes of the longitudinal vibration.

The probe main body section 31 includes a supported portion 38 to be supported by the sheath 7 via an elastic member (not shown). The supported portion 38 is positioned on the distal side with respect to the sectional area increasing portion 37. The probe main body section 31 has a longitudinal dimension L9 from the distal end E6 of the sectional area increasing portion 37 to a proximal end E7 of the supported portion 38 in the longitudinal axis direction. In the certain example, it is preferable that the longitudinal dimension L9 is 24.1 mm. Furthermore, the supported portion 38 has an extending dimension L10 from the proximal end E7 to a distal end E8 in the longitudinal axis direction. The extending dimension L10 is small, and in the certain example, the extending dimension L10 is 3 mm.

In the probe main body section 31, the outer diameter is kept to be substantially constant from the distal end E6 of the sectional area increasing portion 37 to the proximal end E7 of the supported portion 38 in the longitudinal axis direction. Therefore, the probe main body section 31 has the outer diameter D4 at the proximal end E7 of the supported portion 38. That is, at the distal end E6 of the sectional area increasing portion 37 and the proximal end E7 of the supported portion 38, the outer diameter of the probe main body section 31 becomes the outer diameter D4 and has about the same size. In a proximal portion of the supported portion 38, the outer diameter of the probe main body section 31 decreases from the outer diameter D4 to an outer diameter D5. In the certain example, the outer diameter D5 is about 0.4 mm smaller than the outer diameter D4. In the supported portion 38, the outer diameter of the probe main body section 31 is kept to be substantially constant at the outer diameter D5 along a large part in the longitudinal axis direction. Further, in the distal portion of the supported portion 38, the outer diameter of the probe main body section 31 increases from the outer diameter D5 to an outer diameter D6. In consequence, the probe main body section 31 has the outer diameter D6 at the distal end E8 of the supported portion 38. The outer diameter D6 at the distal end E8 of the supported portion 38 is about the same as the outer diameter D4 at the proximal end E7 of the supported portion 38. Consequently, at the proximal end E7 and the distal end E8 of the supported portion 38, the sectional area of the probe main body section 31 which is perpendicular to the longitudinal axis C becomes about the same. In the certain example, it is preferable that the outer diameter D6 is 3.8 mm.

In the state where the vibrating body unit 20 longitudinally vibrates in the established frequency range, a vibration node N3 that is one of the vibration nodes of the longitudinal vibration is positioned in the supported portion 38. Consequently, the probe main body section 31 (the ultrasonic probe 8), which longitudinally vibrates, is also attached to the sheath 7 via the elastic member in the supported portion 38. Furthermore, the probe main body section is supported by the sheath 7 at the vibration node N3 of the longitudinal vibration, and hence in the state where the vibrating body unit 20 longitudinally vibrates in the predetermined frequency range, transmission of the ultrasonic vibration from the supported portion 38 to the sheath 7 is prevented. In the state where the vibrating body unit 20 longitudinally vibrates in the established frequency range, the vibration node (the most distal vibration node) N3 is positioned on the distal side with respect to the vibration node N2, and is positioned most distally among the vibration nodes of the longitudinal vibration. Furthermore, at the proximal end E7 and the distal end E8 of the supported portion 38, the sectional area of the probe main body section 31 which is perpendicular to the longitudinal axis C becomes about the same, and hence in the supported portion 38, the amplitude of the longitudinal vibration hardly changes.

Furthermore, the distal end of the sheath 7 is positioned on the distal side from the distal end E8 of the supported portion 38. Therefore, in the state where the vibrating body unit 20 longitudinally vibrates in the established frequency range, the vibration node N3 positioned most distally among the vibration nodes is positioned inside the sheath 7.

Figure 3:
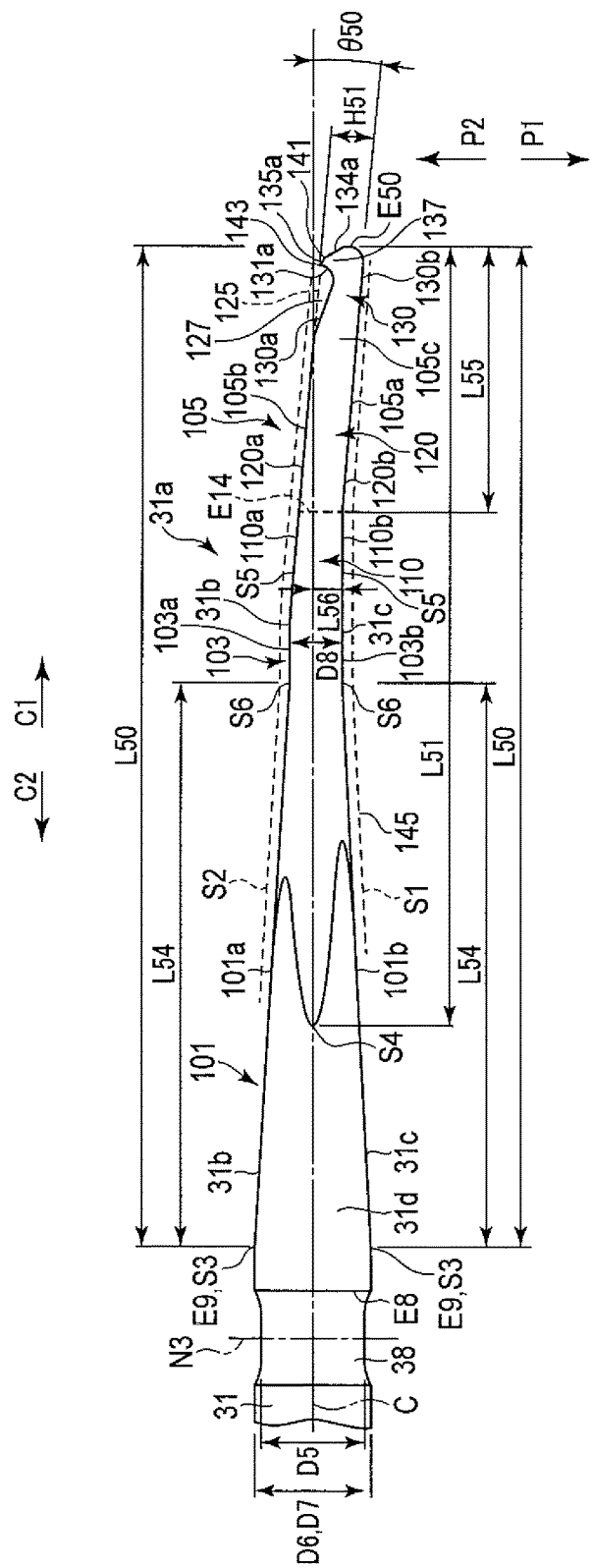
FIG. 3 is a schematic view of a distal portion of an ultrasonic probe according to the first embodiment seen from the first width direction side.

FIG. 3 and FIG. 4 are views showing a constitution of the distal portion of the ultrasonic probe 8. Here, a certain direction that intersects (is substantially perpendicular to) the longitudinal axis C is a first intersecting direction (a direction of an arrow P1 in each of FIG. 2 and FIG. 3), and an opposite direction to the first intersecting direction (a first vertical direction) is a second intersecting direction (a direction of an arrow P2 in each of FIG. 2 and FIG. 3). Furthermore, one of two directions which intersect the longitudinal axis C (substantially perpendicularly) and are perpendicular to (intersect) the first intersecting direction (the first perpendicular direction) and the second intersecting direction (a second perpendicular direction) is a first width direction (a direction of an arrow B1 in FIG. 4). Further, an opposite direction to the first width direction is a second width direction (a direction of an arrow B2 in FIG. 4). Here, FIG. 2 and FIG. 3 are views of the ultrasonic probe 8 seen from a first width direction side, and FIG. 4 is a view of the ultrasonic probe 8 seen from a second perpendicular direction side. It is to be noted that in FIG. 3, a range shown by a broken line S1 and a broken line S2 projects from the distal end of the sheath 7 toward the distal side.

As shown in FIG. 3 and FIG. 4, the probe main body section 31 extends to a position located on the distal side with respect to the supported portion 38. That is, a distal end E9 of the probe main body section 31 is positioned on the distal side from the distal end E8 of the supported portion 38. However, a distance between the distal end E8 of the supported portion 38 and the distal end E9 of the probe main body section 31 in the longitudinal axis direction is small, and is about 0.6 mm in the certain example.

As described above, in the probe main body section 31, the amplitude of the longitudinal vibration is enlarged in the horn portion (the first horn portion) 35 and the horn portion (the second horn portion) 36, and the amplitude of the longitudinal vibration hardly changes in the sectional area increasing portion 37 and the supported portion 38. Due to the above-mentioned constitution, in the certain example, the longitudinal vibration of an amplitude of 80 μm occurs at the distal end E9 of the probe main body section 31, in a case where the longitudinal vibration of an amplitude of 18 μm at the vibration antinode is transmitted to the proximal end (the abutment surface 33) of the probe main body section 31.

In the ultrasonic probe 8, the distal side of the probe main body section 31 is continuous with a distal constituting section 31a. For example, a part located on a forward side with respect to the distal end E9 of the probe main body section 31 functions as the distal constituting section 31a.

As shown in FIG. 3, the distal constituting section 31a has a reference surface 31b including an after-mentioned blade tip portion 143, and an opposite surface 31c disposed on a side opposite to the reference surface 31b. The reference surface 31b is an upper surface of the distal constituting section 31a and the opposite surface 31c is a lower surface of the distal constituting section 31a. Furthermore, the reference surface 31b faces a first intersecting direction side and the opposite surface 31c faces a second intersecting direction side. The reference surface 31b and the opposite surface 31c are narrowed so that the distal constituting section 31a tapers off toward a distal end E50 of the distal constituting section 31a. As shown in FIG. 3 and FIG. 4, on the reference surface 31b and the opposite surface 31c, a narrowing start position S3 is a position that is distant from the distal end E50 as much as a longitudinal dimension L50 in a longitudinal axis C direction. It is preferable that the longitudinal dimension L50 is 32 mm. The narrowing start position S3 of the reference surface 31b and the opposite surface 31c is a continuous position of a proximal end of a tapered section 101 with the distal end E9 of the probe main body section 31, and is also a boundary position between the probe main body section 31 and the tapered section 101.

As shown in FIG. 3 and FIG. 4, in a circumferential direction of the distal constituting section 31a, the reference surface 31b and the opposite surface 31c are continuous with both side surfaces 31d of the distal constituting section 31a. One of the side surfaces 31d faces the first width direction side and the other side surface 31d is directed on a second width direction side. As shown in FIG. 4, parts of the side surfaces 31d are narrowed to taper off toward the distal end E50. As shown in FIG. 3 and FIG. 4, on the side surfaces 31d, a narrowing start position S4 of each side surface 31d is a position that is distant as much as a longitudinal dimension L51 from the distal end E50 in the longitudinal axis C direction. It is preferable that the longitudinal dimension L51 is 25 mm. It is to be noted that a part located on the distal side with respect to a narrowing end position S5 on each side surface 31d, each side surface 31d is not narrowed, and as shown in FIG. 4, the narrowing end position S5 is a position that is distant as much as a longitudinal dimension L53 from the distal end E50. It is preferable that the longitudinal dimension L53 is 10 mm. Furthermore, between the constricting start position S3 and the constricting start position S4, the side surfaces 31d are not constricted.

As shown in FIG. 3 and FIG. 4, the distal constituting section 31a has the tapered section 101 (a sectional area decreasing portion), a relay extending section 103, and a curving section (a curved extending section) 105. A distal portion of the tapered section 101 is continuous with a proximal portion of the relay extending section 103, and a distal portion of the relay extending section 103 is continuous with a proximal portion of the curving section 105.

As shown in FIG. 3 and FIG. 4, in the tapered section 101, the sectional area perpendicular to the longitudinal axis C decreases toward the distal side. It is preferable that a maximum outer diameter D7 of the tapered section 101 (at the narrowing start position S3) is 3.8 mm. It is preferable that a minimum thickness (a minimum outer diameter) D8 of the tapered section 101 (at the narrowing end position S5 or a narrowing end position S6) is 1.7 mm.

As shown in FIG. 3, a part 101a of the tapered section 101 is included in the reference surface 31b and is, for example, an upper surface of the tapered section 101. A part 101b of the tapered section 101 is included in the opposite surface 31c and is, for example, a lower surface of the tapered section 101. The part 101b forms a first narrowed outer surface faces the first intersecting direction side in the tapered section 101, and the part 101a forms a second narrowed outer surface directed on the second intersecting direction side in the tapered section 101. The parts 101a and 101b are narrowed from the narrowing start position S3 to the narrowing end position S6. Consequently, in the part (the first narrowed outer surface) 101b, a first distance from the longitudinal axis C in the first intersecting direction decreases toward the distal side from the proximal side. Further, in the part (the second narrowed outer surface) 101a, a second distance from the longitudinal axis C in the second intersecting direction decreases toward the distal side from the proximal side. The constricting end position S6 is positioned forwardly from (on the distal side from) the narrowing start position S3. It is preferable that a longitudinal dimension L54 from the narrowing start position S3 to the narrowing end position S6 is 18 mm. The parts 101a and 101b function as an after-mentioned narrowing region.

As shown in FIG. 3 and FIG. 4, in the tapered section 101, the side surfaces 31d are narrowed from the narrowing start position S4 to the narrowing end position S5. In the tapered section 101, the side surfaces 31d are not narrowed in a part located on the proximal side with respect to the narrowing start position S4, and this length is a length from the narrowing start position S3 to the narrowing start position S4.

In the tapered section 101, the sectional area perpendicular to the longitudinal axis C decreases toward the distal side. In the state where the vibrating body unit 20 longitudinally vibrates in the established frequency range (e.g., 46 kHz or more and 48 kHz or less), the vibration node (the most distal vibration node) N3 that is one of the vibration nodes of the longitudinal vibration is positioned in the supported portion 38 and positioned in the vicinity of a proximal end (E9) of the tapered section 101. Further, in the state where the vibrating body unit 20 longitudinally vibrates in the predetermined frequency range, each of the vibration antinodes of the longitudinal vibration is positioned away from the tapered section 101 in the longitudinal axis direction. Consequently, in the tapered section 101 in which the sectional area decreases toward the distal side, the amplitude of the longitudinal vibration (the ultrasonic vibration) is enlarged. In the certain example, the distal end E50 longitudinally vibrates at 140 µm to 150 µm, in a case where the longitudinal vibration of an amplitude of 80 µm at the vibration antinode is transmitted to the proximal end (E9) of the tapered section 101.

Furthermore, in the present embodiment, a dimension of the tapered section 101 from the proximal end (E9) to a distal end (S5) in the longitudinal axis direction is larger than a ⅛ wavelength (λ/8) in the state where the vibrating body unit 20 longitudinally vibrates in the established frequency range. In the certain example, in the state where the vibrating body unit 20 longitudinally vibrates at 46 kHz or more and 48 kHz or less (the established frequency range), a ¼ wavelength (λ/4) from the vibration node (the most distal vibration node) N3 to the distal end E50 that is the vibration antinode (the most distal vibration antinode) A2 is 34.4 mm or more and 35.2 mm or less. On the other hand, in this example, a dimension from the proximal end (E9) of the tapered section 101 to the narrowing end position S5 in the longitudinal axis direction is about 22 mm, and is larger than the ⅛ wavelength in the state where the vibrating body unit 20 longitudinally vibrates at 46 kHz or more and 48 kHz or less (the predetermined frequency range). Furthermore, in the tapered section 101, it is preferable that the longitudinal dimension L54 between the proximal end (E9) and the constricting end position S6 in the longitudinal axis direction is also 18.1 mm. Therefore, the longitudinal dimension L54 is also larger than the ⅛ wavelength in the state where the vibrating body unit 20 longitudinally vibrates at 46 kHz or more and 48 kHz or less (the established frequency range).

As shown in FIG. 3, the reference surface 31b and the opposite surface 31c in the relay extending section 103 are not narrowed but are arranged in parallel along the longitudinal axis C. As shown in FIG. 4, the side surfaces 31d are narrowed up to the narrowing end position S5 in the relay extending section 103. A length of the relay extending section 103 is a length from the narrowing end position S6 to the narrowing end position S5. This region functions as an after-mentioned parallel region.

As shown in FIG. 5A, the curving section 105 has a central axis C0 that bends relative to the longitudinal axis C that is the central axis of the probe main body section 31. The central axis C0 of the curving section 105 bends away from the longitudinal axis C (toward the downside) from the proximal portion of the curving section 105 toward a distal portion of the curving section 105. The central axis C0 linearly extends. Further, as shown in FIG. 3 and FIG. 5A, the curving section (the curved extending section) 105 is bent relative to the probe main body section 31 (the longitudinal axis direction) in a part located on the distal side with respect to the probe main body section 31. The curving section 105 linearly bends away from the longitudinal axis C toward the first intersecting direction side. The bent curving section 105 is always disposed in a projection plane of the probe main body section 31, when the ultrasonic probe 8 is seen along the longitudinal axis C from the proximal end toward the distal end (i.e., in projection from the proximal side). As shown in FIG. 4, in the curving section 105, the side surfaces 31d are not constricted and the curving section corresponds to a portion having the longitudinal dimension L53.

As shown in FIG. 3, FIG. 5A and FIG. 6, the curving section (the curved extending section) 105 includes a first curved outer surface 105a facing the first intersecting direction side, and a second curved outer surface 105b facing the second intersecting direction side. The first curved outer surface 105a is a part of the opposite surface 31c, and the second curved outer surface 105b is a part of the reference surface 31b. Furthermore, the curving section 105 includes a third curved outer surface 105c facing the first width direction side, and a fourth curved outer surface 105d directed on the second width direction side. The curving section 105 has a sectional area decreasing portion 110, a sectional area uniform portion 120, and a treating section 130. A proximal portion of the sectional area decreasing portion 110 is continuous with the distal portion of the relay extending section 103. A proximal portion of the sectional area uniform portion 120 is continuous with a distal portion of the sectional area decreasing portion 110. A proximal portion of the treating section 130 is continuous with a distal portion of the sectional area uniform portion 120. The sectional area decreasing portion 110 is provided in the proximal portion of the curving section 105, the treating section 130 is disposed in the distal portion of the curving section 105, and the sectional area uniform portion 120 is interposed between the sectional area decreasing portion 110 and the treating section 130. For example, a femur that is an affected area 200 in a knee joint is treated (cut) with the treating section 130.

As shown in FIG. 3 and FIG. 5A, a part 110a of the sectional area decreasing portion 110 is included in the reference surface 31b and the second curved outer surface 105b, and is, for example, an upper surface of the sectional area decreasing portion 110. The part 110a is narrowed into a tapered state. Specifically, the part 110a is linearly bent relative to the reference surface 31b (a part 103a) in the relay extending section 103 in a direction to approach the longitudinal axis C (downwardly toward the longitudinal axis C). A bending angle (an acute angle) θ50 is 5 degrees or more and 20 degrees or less.

As shown in FIG. 3 and FIG. 5A, a part 110b of the sectional area decreasing portion 110 is included in the opposite surface 31c and the first curved outer surface 105a, and is, for example, a lower surface of the sectional area decreasing portion 110. The part 110*b* is disposed in parallel with the longitudinal axis C. It is preferable that a dimension L56 between the part 110*b* and the longitudinal axis C is 0.95 mm.

As shown in FIG. 5A, due to the part 110*a* and the part 110*b*, the central axis C1 of the sectional area decreasing portion 110 which is included in the central axis C0 of the curving section 105 is linearly bent relative to the longitudinal axis C toward a direction away from the longitudinal axis C (downwardly from the longitudinal axis C). That is, the sectional area decreasing portion 110 bends in the first intersecting direction side relative to the longitudinal axis C.

As shown in FIG. 3 and FIG. 5A, the sectional area uniform portion 120 has a uniform thickness. As shown in FIG. 5A and FIG. 5B, it is preferable that a height (a thickness dimension) H51 of the sectional area uniform portion 120 is 1.4 mm. It is preferable that a width (a width dimension) W51 of the sectional area uniform portion 120 is 2.8 mm. In a periphery of the sectional area uniform portion 120, each corner radius R51 is 0.5 mm.

As shown in FIG. 5A, a part 120*a* of the sectional area uniform portion 120 is included in the reference surface 31*b* and the second curved outer surface 105*b*, and is, for example, an upper surface of the sectional area uniform portion 120. The part 120*a* is continuous with the part 110*a* of the sectional area decreasing portion 110, and is disposed on the same straight line as in the part 110*a*. Consequently, the part 120*a* is, similarly to the part 110*a*, linearly bent relative to the reference surface 31*b* (the part 103*a*) in the relay extending section 103 toward a direction to approach the longitudinal axis C (downwardly toward the longitudinal axis C). A bending angle (an acute angle) θ50 is 5 degrees or more and 20 degrees or less. As shown in FIG. 3 and FIG. 6, the part 120*a* extends up to the longitudinal axis C so that a distal portion of the part 120*a* intersects the longitudinal axis C. As shown in FIG. 3 and FIG. 5A, the part 120*a* is continuous with the treating section 130, and functions as a first bending surface that bends relative to a peripheral surface of the relay extending section 103 to approach the longitudinal axis C, thereby intersecting the longitudinal axis C. Therefore, the parts 110*a* and 120*a* become extending surfaces which extend in a state of bending relative to the probe main body section 31 and the tapered section 101 toward the first intersecting direction side.

As shown in FIG. 3 and FIG. 5A, a part 120*b* of the sectional area uniform portion 120 is included in the opposite surface 31*c* and the first curved outer surface 105*a*, and is, for example, a lower surface of the sectional area uniform portion 120. The part 120*b* is continuous with the part 110*b* of the sectional area decreasing portion 110 included in the opposite surface 31*c*. The part 120*b* is linearly bent relative to the part 110*b* in the direction away from the longitudinal axis C (downwardly from the longitudinal axis C). A bending angle (an acute angle) θ50 is 5 degrees or more and 20 degrees or less in the same manner as in the above-mentioned bending angles θ50. Consequently, the bending angles θ50 correspond to the bending angles of the part 110*a* and the circumferential surface of the sectional area uniform portion 120. In consequence, the part 120*a* is disposed in parallel with the part 120*b*. As shown in FIG. 3 and FIG. 6, a distal portion of the part 120*b* is positioned below the longitudinal axis C.

As shown in FIG. 5A, due to the part 120*a* and the part 120*b*, a central axis C2 of the sectional area uniform portion 120 which is included in the central axis C0 of the curving section 105 is linearly bent relative to the central axis C1 of the sectional area decreasing portion 110 toward the direction away from the longitudinal axis C (downwardly from the longitudinal axis C). That is, the central axis C2 bends toward the first intersecting direction side relative to the central axis C1. A bending angle θ50 is 5 degrees or more and 20 degrees or less in the same manner as in the above-mentioned bending angles θ50. It is to be noted that the central axis C0 of the curving section 105 preferably bends at an angle of 5 degrees or more and 8 degrees or less relative to the longitudinal axis C of the probe main body section 31 (the longitudinal axis direction). That is, it is preferable that the bending angle (the acute angle) θ50 is 5 degrees or more and 8 degrees or less.

As shown in FIG. 3 and FIG. 5A, it is preferable that a longitudinal dimension L55 from the distal end E50 to a bending start position (a first curving start position) E14 of the opposite surface 31*c* (the first curved outer surface 105*a*) is 8.5 mm. The bending start position E14 is a continuous region of the part 110*b* with the part 120*b*. Consequently, the curving section 105 is formed on the basis of the bending start position E14. The longitudinal dimension L55 indicates a sum of a length of the sectional area uniform portion 120 and a length of the treating section 130.

In the bending of the curving section (the curved extending section) 105, the second curved outer surface 105*b* that is an upper surface of the curving section 105 includes the blade tip portion 143 of a treating region and a circumferential surface of an after-mentioned projecting portion 137, and the second curved outer surface is bent relative to an upper surface of the relay extending section 103. Furthermore, the first curved outer surface 105*a* that is a lower surface of the curving section 105 is disposed on a side opposite to the upper surface of the curving section 105 with respect to the central axis C0 of the curving section 105, and the first curved outer surface is bent relative to a lower surface of the relay extending section 103. The upper surface of the curving section 105 includes, for example, the part 110*a*, the part 120*a*, and a part 130*a* on the reference surface 31*b*. The lower surface of the curving section 105 includes, for example, the part 110*b*, the part 120*b*, and a part 130*b* on the opposite surface 31*c*. The part 103*a* is included in the reference surface 31*b*, and is, for example, the upper surface of the relay extending section 103. A part 103*b* is included in the opposite surface 31*c* in the same manner as in the part 110*b*. The part 103*b* is a lower surface of the relay extending section 103. A bending start position (a second curving start position) E15 of the upper surface of the curving section 105 relative to the upper surface (the longitudinal axis direction) of the relay extending section 103 is a continuous region of the part 103*a* with the part 110*a*. The bending start position (the first curving start position) E14 of the lower surface of the curving section 105 relative to the lower surface (the longitudinal axis direction) of the relay extending section 103 is a continuous region of the part 110*b* with the part 120*b*. The bending start position E14 is positioned on the distal side with respect to the bending start position E15. The probe main body section 31 and the curving section 105 vibrate in the established frequency range in a state where the ultrasonic vibration is transmitted from the probe main body section 31 to the curving section 105. In the state where the probe main body section 31 and the curving section 105 are vibrated in the established frequency range, the bending start positions E14 and E15 are positioned forwardly from the most distal vibration node N3 of the vibration nodes, i.e., positioned on the distal side of the curving section 105 with respect to the most distal vibration node.

As shown in FIG. 4, it is preferable that a width W52 of the treating section 130 (a width dimension between the third curved outer surface 105c and the fourth curved outer surface 105d in the treating section 130 in the first width direction and the second width direction) is 2.8 mm in the same manner as in the width W51 of the sectional area uniform portion 120.

As shown in FIG. 3 and FIG. 6, the part 130a of the treating section 130 is included in the reference surface 31b and the second curved outer surface 105b, and is, for example, an upper surface of the treating section 130. The part 130a is linearly bent relative to the part (the extending surface) 120a of the sectional area uniform portion 120 included in the reference surface 31b, in the direction away from the longitudinal axis C (downwardly from the longitudinal axis C). The part 130a is disposed in the treating section 130, and functions as a second bending surface that bends relative to the first bending surface (the extending surface), in a bending direction of the part 120a as the first bending surface and a direction away from the longitudinal axis C (i.e., toward the first intersecting direction side).

As shown in FIG. 3 and FIG. 6, the part 130a smoothly curves into a circular shape, and is continuous with a part 131a included in the reference surface 31b and the second curved outer surface 105b. The part 131a is disposed in the treating section 130, and functions as a third bending surface that bends relative to the part 130a as the second bending surface in a direction to approach the longitudinal axis C on a side reverse to the bending direction of the part 120a as the first bending surface (i.e., toward the second intersecting direction side), and extends toward an extension line 125 of the part 120a as the first bending surface. The part 131a extends up to a position that is on the extension line 125 of the part (the extending surface) 120a or a position below the extension line 125, toward the longitudinal axis C relative to the part 130a. The part 131a is, for example, the upper surface of the treating section 130.

As shown in FIG. 6, when seen from the respective sides of the side surfaces 31d, a curved surface portion 132a between the part 130a and the part 131a has a corner radius R52, and the corner radius R52 is 0.5 mm. In the curved surface portion 132a, the part 131a has an angle θ51 relative to the part 130a, and the angle θ51 is 90 degrees. It is preferable that a height H52 of the part 131a relative to the part 130a is 0.6 mm. An angle (the acute angle) θ52 formed between the longitudinal axis C direction and the part 131a is 55 degrees or more and 85 degrees or less.

As shown in FIG. 6, due to the parts 130a and 131a, a concave portion (a concave surface) 127 is formed in a distal portion of the reference surface 31b (the second curved outer surface 105b). The concave surface 127 is concaved relative to the part (the extending surface) 120a toward the first intersecting direction side.

As shown in FIG. 3 and FIG. 6, the part 130b of the treating section 130 is included in the opposite surface 31c and the first curved outer surface 105a, and is, for example, a lower surface of the treating section 130. The part 130b is continuous with the part 120b of the sectional area uniform portion 120 included in the opposite surface 31c, and is disposed on the same straight line as in the part 120b. The part 130b extends up to a region located forwardly (on the distal side) from the curved surface portion 132a. The part 130b smoothly curves into a circular shape toward the longitudinal axis C and a rear side, and is continuous with a part 134a included in the reference surface 31b and the second curve outer surface 105b. The part 134a is, for example, the upper surface of the treating section 130.

As shown in FIG. 6, when seen from the respective sides of the side surfaces 31d, a curved surface portion 132b between the part 130b and the part 134a has a corner radius R53, and the corner radius R53 is 0.5 mm. The part 134a tilts at an angle 953 relative to the part 130b. The angle 953 is 55 degrees. As shown in FIG. 4, when seen from a reference surface 31b side, the curved surface portion 132b has a corner radius R54, and the corner radius R54 is 0.5 mm.

As shown in FIG. 6, a boundary point 133 between the part 130b and the curved surface portion 132b is a region which is most distant from the longitudinal axis C in the treating section 130, in a thickness direction (a radius direction) of the distal constituting section 31a. The boundary point 133 is positioned between the longitudinal axis C and the opposite surface 31c in one region (e.g., E9) of the tapered section 101 having the maximum outer diameter D7, in the thickness direction of the distal constituting section 31a. That is, the boundary point 133 is positioned on the second intersecting direction side with respect to a region of an outer surface which is directed on the first intersecting direction side at the proximal end of the tapered section 101. That is, when the distal end is seen from the proximal end along the longitudinal axis C (in the projection from the proximal side in the longitudinal axis direction), the curving section 105 including the treating section 130 having the boundary point 133 is always disposed in the projection plane of the tapered section 101 (the probe main body section 31).

As shown in FIG. 3 and FIG. 6, the part 134a is bent rearward, and is continuous with a part 135a included in the reference surface 31b (the second curved outer surface 105b). This continuous region (a bent portion) becomes a boundary portion 141. The boundary portion 141 is linearly formed along the width directions (the arrows B1 and B2 directions) of the treating section 130, and is an end portion (a boundary) between the part 134a and the part 135a. The part 135a is, for example, the upper surface of the treating section 130.

As shown in FIG. 6, the part 135a is bent at an angle θ54 relative to the extension line 125. The angle (an acute angle) θ54 is 25 degrees. In other words, the part 135a tilts at the angle θ54 relative to the central axis C2 of the sectional area uniform portion 120.

As shown in FIG. 3 and FIG. 6, the part 135a is continuous with the part 131a. The part 135a tilts at an angle θ55 around a continuous region between the part 135a and the part 131a toward the part 134a (away from the longitudinal axis C (downward)). The angle θ55 is 30 degrees or more and 45 degrees or less. The part 135a functions as a cutting surface that bends relative to the part 131a that is a third bending surface in the bending direction of the part 120a that is a first bending surface. It is to be noted that in the present embodiment, the part 134a is disposed forwardly with respect to (on the distal side from) the part 135a, and functions as an extending surface that bends relative to the part 135a in the direction away from the longitudinal axis C. Therefore, the part 135a as the cutting surface tilts relative to a longitudinal axis direction in a state where the part extends toward the first intersecting direction side as it extends toward the distal side. Furthermore, the part 134a as the extending surface is continuous with the distal side of the part 135a. Further, the part 135a bends relative to the part 134a toward the first intersecting direction side in a state where the acute angle relative to the longitudinal axis direction is larger than that of the part 134a.

As shown in FIG. 3 and FIG. 6, the continuous region between the part 135a and the part 131a functions as the blade tip portion 143. Consequently, the part 135a has the blade tip portion 143. Further, the part 135a bends relative to the blade tip portion 143 in the bending direction of the part 120a and a direction away from the extension line 125 of the part 120a, with the blade tip portion 143 being a center. Furthermore, the parts 134a and 135a tilt relative to the longitudinal axis C. Therefore, the part 135a that is the cutting surface extends from the blade tip portion 143 toward the distal side.

As shown in FIG. 6, it is preferable that a longitudinal dimension L57 in a longitudinal direction between the distal end E50 formed in the curved surface portion 132b (a distal end of the part 134a) and the blade tip portion 143 is 0.6 mm. As shown in FIG. 3, FIG. 4 and FIG. 6, the blade tip portion 143 is formed linearly along the width direction of the treating section 130, and is an end portion (a boundary) of the part 131a and the part 135a. It is preferable that a height H53 (a thickness dimension in the thickness direction) between the blade tip portion 143 and the boundary point 133 (the first curved outer surface 105a) is 1.4 mm. The height H53 is a height of a distal portion of the treating section 130 including the projecting portion 137 that will be described later, and is shorter than the width W52 of the treating section 130. That is, at a position of a projecting end (143) of the projecting portion 137 in the longitudinal axis direction, the thickness dimension (H53) of the curved extending section 105 between the projecting end (143) and the first curved outer surface 105a in the thickness direction is smaller than the width dimension (W52) between the third curved outer surface 105c and the fourth curved outer surface 105d in the first width direction and the second width direction. It is to be noted that the width W52 is preferably 2.8 mm as described above. The blade tip portion 143 is disposed at the highest position in the treating section 130, the part 131a and the part 135a. As shown in FIG. 6, the part 135a including the blade tip portion 143 is positioned on the extension line 125 of the part 120a or below the extension line 125 (on the first intersecting direction side). The blade tip portion 143 is disposed in a continuous region of the part 131a as the third bending surface with the part 135a as the cutting surface (a treating surface). As shown in FIG. 6, the blade tip portion 143 functions as a treating region positioned on the extension line 125 of the part 120a as the first bending surface or positioned on a side opposite to the longitudinal axis C with respect to a boundary that is the extension line 125 of the part 120a as the first bending surface. That is, the blade tip portion 143 is disposed at a position that is on the extension line 125 or a position below the extension line 125. Furthermore, the blade tip portion 143 is positioned on the first intersecting direction side with respect to the longitudinal axis of the probe main body section 31.

As shown in FIG. 6, in the above-mentioned shape of the treating section 130, the treating section 130 has the projecting portion 137 projecting toward a side reverse to a bending direction of the central axis C0 of the curving section 105 relative to the longitudinal axis C (i.e., toward the second intersecting direction side), and the blade tip portion 143 of the treating region disposed at the end of the projecting portion 137 and therefore disposed at the position reverse to the bending direction of the central axis C0 relative to the longitudinal axis C to treat the knee joint. That is, the blade tip portion 143 is a projecting end of the projecting portion 137, and the projecting end of the projecting portion 137 is formed by the part 131a and the part 135a that is the cutting surface. The projecting portion 137 becomes a part of the second curved outer surface 105b. Furthermore, the concave portion (the concave surface) 127 formed by the parts 130a and 131a is continuous between the part 120a that is the extending surface and the part 135a that is the cutting surface in the second curved outer surface 105b, and is concaved relative to the part 135a toward the first intersecting direction side.

The projecting portion 137 is, for example, a regional portion surrounded with the curved surface portion 132a and the parts 131a, 135a and 134a. The curved surface portion 132a and the parts 131a, 135a and 134a constitute a circumferential surface of the projecting portion 137. The end (the projecting end) of the projecting portion 137 is a continuous region of the part 131a with the part 135a. A maximum height of the projecting portion 137 is the height H52 of the part 131a relative to the part 130a.

The distal constituting section 31a has the tapered section 101, the relay extending section 103 and the curving section (the curved extending section) 105 as described above. When a viewpoint is changed, the ultrasonic probe 8 has a narrowed region, a parallel region and an intersecting region.

As shown in FIG. 3, the narrowed region is disposed in the distal constituting section 31a, and is tapered and narrowed toward the longitudinal axis C. The constricted region has the parts 101a and 101b. The parts 101a and 101b are vertically symmetrically arranged about the longitudinal axis C, and have the same length, shape and tilt as each other. Consequently, a narrowing angle (a second narrowing angle) on an upper surface (a second narrowed outer surface) is the same as a narrowing angle (a first narrowing angle) on a lower surface (a first narrowed outer surface). The narrowed region vibrates together with the probe main body section 31 and the curving section 105 in the established frequency range in a state where the ultrasonic vibration is transmitted from the probe main body section 31 to the curving section 105 through the narrowed region. In the state where the narrowed region is vibrated together with the probe main body section 31 and the curving section 105 in the predetermined frequency range, each of the longitudinal dimension L54 of the narrowed region and a dimension from the proximal end (E9) of the narrowed region to the narrowing end position S5 is larger than a ⅛ wavelength of the vibration. The constricted region and the treating section 130 disposed on the distal side with respect to the narrowed region are arranged in a ¼ wavelength of the vibration.

As shown in FIG. 3 and FIG. 5A, a parallel region is disposed forwardly with respect to (on the distal side from) the distal portion of the probe main body section 31 and the narrowed region, and is continuous with the narrowed region, and the parts 103a, 103b and 110b are parallel to the longitudinal axis C. The parallel region has, for example, the reference surface 31b and the opposite surface 31c in the relay extending section 103, and the opposite surface 31c in the sectional area decreasing portion 110. In other words, the parallel region has, for example, the parts 103a and 103b of the relay extending section 103 and the part 110b of the sectional area decreasing portion 110. The part 103a is an upper surface (a second axis parallel outer surface) that is continuous between the part (the second narrowed outer surface) 101a and the second curved outer surface 105b and is parallel to the longitudinal axis C. The parts 103b and 110b are lower surfaces (first axis parallel outer surfaces) which are continuous between the part (the first narrowed outer surface) 101b and the first curved outer surface 105a and are arranged on a side opposite to the upper surface with respect to the longitudinal axis C. The parts 103b and 110b are parallel to the longitudinal axis C, and are longer than the part 103a that forms the upper surface (the second axis parallel outer surface). The part 103a and the part 103b are vertically symmetrically arranged about the longitudinal axis C, and have the same length and shape each other. The part 110b is provided, and hence the lower surface in the parallel region is longer than the upper surface in the parallel region, and extends to the distal side more than the upper surface in the parallel region.

As shown in FIG. 5A and FIG. 6, the intersecting region is disposed in the curving section 105, is continuous with the parallel region, and intersects the longitudinal axis C. The intersecting region has, for example, the reference surface 31b in the curving section 105. In other words, the intersecting region has the part 120a of the sectional area uniform portion 120.

As described above, the bent curving section 105 is always disposed in the projection plane of the probe main body section 31, when the ultrasonic probe 8 is seen along the longitudinal axis C from its proximal end toward its distal end. Further, the part 101b is narrowed toward the longitudinal axis C. The continuous part 103b is continuous with the distal end of the part 101b and parallel to the longitudinal axis C, and the part 110b is continuous with the distal end of the part 103b and parallel to the longitudinal axis C. The parts 103b and 110b are always arranged in the projection plane of the probe main body section 31. The parts 120b and 130b are linearly bent in the direction away from the longitudinal axis C, but are always arranged in the projection plane of the probe main body section 31 in the same manner as in the parts 103b and 110b. Consequently, as shown in FIG. 3, a space 145 is formed on an opposite surface 31c side and in the projection plane of the probe main body section 31. The space 145 is positioned between the proximal end E9 (the proximal end of the part 101a) and the distal end of the part 130b in the longitudinal axis C direction, and positioned on the lateral side of the distal constituting section 31a. The space 145 is disposed on a side reverse to the blade tip portion 143 with respect to the distal constituting section 31a.

Next, a function and an effect of the ultrasonic probe 8 of the present embodiment will be described.

For example, in a surgical operation under endoscope observation of, for example, the knee joint, an unshown port (opening) disposed to approach the affected area 200 is usually set at a predetermined position.

In the shape of the ultrasonic probe 8, when the ultrasonic probe 8 is seen from a proximal portion toward the distal portion of the ultrasonic probe 8 along the longitudinal axis of the ultrasonic probe 8, differently from the present embodiment, it is defined that the distal portion of the ultrasonic probe is bent relative to the proximal portion so that the distal portion of the ultrasonic probe 8 is always disposed outside the projection plane of the proximal portion of the ultrasonic probe. Further, it is defined that the treating section 130 is disposed in the distal portion. In this case, the port is usually narrow, a tubular member is thin, a cavity in the knee joint is narrow, and a circumferential surface of the femur is formed into a curved surface. Consequently, in the above-mentioned shape of the ultrasonic probe 8, inserting properties of the ultrasonic probe 8 to the tubular member and approaching properties of the treating region in the ultrasonic probe 8 to the affected area 200 would deteriorate. In the ultrasonic probe 8, a direction in which the affected area can be treated is determined in accordance with the vibrating direction. When the ultrasonic probe 8 does not come in contact with the affected area 200 in an appropriate state, an efficiency of the treatment deteriorates. Furthermore, the cavity is narrow, and the affected area is formed into the curved surface. Consequently, the above-mentioned shape of the ultrasonic probe 8 is not suitable to treat the affected area 200 in the narrow cavity. Furthermore, in the above-mentioned shape of the ultrasonic probe 8, the probe would come in contact with an area other than the affected area to damage the area other than the affected area, before coming in contact with the affected area. Consequently, the ultrasonic probe is not suitable to treat the affected area in the narrow cavity.

In the present embodiment, the curving section 105 is bent relative to the probe main body section 31. When a distal end of the curving section 105 is seen from its proximal end along the longitudinal axis C direction, the curving section 105 including the treating section 130 having the boundary point 133 is always disposed in the projection plane of the tapered section 101. The central axis of the curving section 105 bends at an angle of five degrees or more and eight degrees or less relative to the longitudinal axis C of the probe main body section 31.

Figure 8A:
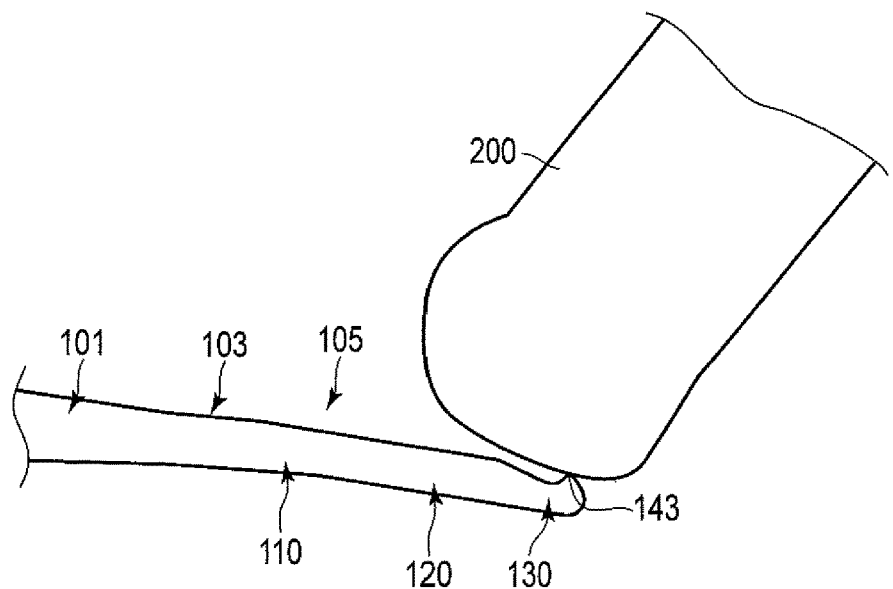
FIG. 8A is a schematic view showing one example of a treatment of the ultrasonic probe.
Figure 8B:
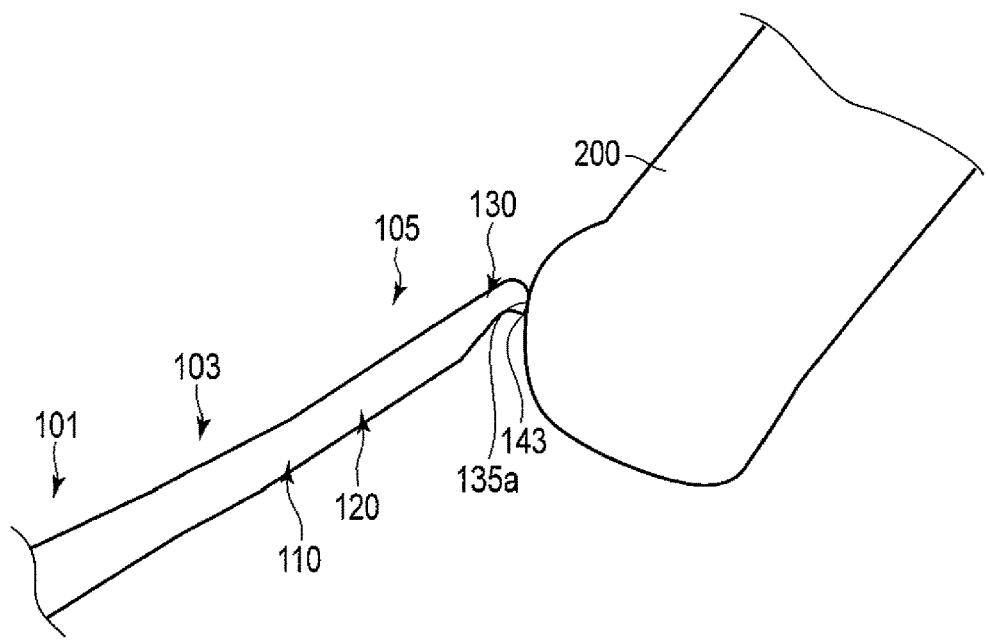
FIG. 8B is a schematic view showing another example of the treatment of the ultrasonic probe which is different from the example of FIG. 8A.

Consequently, even when the port is narrow and the tubular member is thin, the inserting properties of the ultrasonic probe 8 into the tubular member can improve in the ultrasonic probe 8 having the curving section 105, as long as the probe main body section 31 is inserted into the tubular member. Furthermore, the ultrasonic probe 8 having the curving section 105 can be inserted through the tubular member in accordance with a degree of the curve of the curving section 105, and during the insertion, the curving section 105 does not have to abut on an inner peripheral surface of the tubular member. Further, as shown in FIG. 8A and FIG. 8B, it is possible to improve the approaching properties of the blade tip portion 143 as the treating region in the ultrasonic probe 8 to the femur that is the affected area 200, and it is possible to improve the treatment efficiency to the affected area 200. In the present embodiment, as shown in FIG. 8A and FIG. 8B, by rotating the ultrasonic probe 8 around the axis of the probe main body section 31 and changing an orientation of the blade tip portion 143, it is possible to easily treat any regions of the femur and to improve the treatment efficiency and a treatment quality. In a case where the affected area 200 is present in a innermost area of a cruciate ligament, the blade tip portion 143 can easily approach the affected area 200.

In the present embodiment, the part 120a as the first bending surface (the extending surface) is bent relative to the circumferential surface of the probe main body section 31 to approach the longitudinal axis C, thereby intersecting with the longitudinal axis C. Further, the blade tip portion 143 that is the treating region (the projecting end of the projecting portion 137) is positioned on the extension line 125 of the part 120a as the first bending surface. Alternatively, the extension line 125 of the part 120a that is the first bending surface is the boundary, and the blade tip portion is positioned on the side opposite to the longitudinal axis C with respect to the boundary (i.e., positioned on the first intersecting direction side from the extension line 125). The blade tip portion 143 is linearly formed along the width direction of the treating section 130.

Consequently, even when a cavity between the femur and a tibia is narrow and a lower surface of the femur is formed into a curved surface, the affected area 200 can appropriately be treated with the ultrasonic probe 8 in accordance with the shape of the ultrasonic probe 8. Furthermore, the affected area is not limited to the knee joint, and in a narrow cavity of a joint (e.g., a shoulder joint) other than the knee joint, the affected area 200 can appropriately be treated with the ultrasonic probe 8 in accordance with the shape of the ultrasonic probe 8. Furthermore, as shown in FIG. 8A and FIG. 8B, it is possible to improve the approaching properties of the blade tip portion 143 as the treating region in the ultrasonic probe 8 to the femur that is the affected area 200, and it is possible to improve the treatment efficiency to the affected area 200. Especially, even when the ultrasonic probe 8 (the probe main body section 31) is obliquely approached to the affected area 200, the blade tip portion 143 tilts, and hence the treatment efficiency can improve. Furthermore, in the present embodiment, as shown in FIG. 8A and FIG. 8B, by rotating the probe main body section 31 around the axis of the probe main body section 31 and changing the orientation of the blade tip portion 143, it is possible to easily treat any regions of the femur and to improve the treatment efficiency and the treatment quality. In the case where the affected area 200 is present in the innermost area of the cruciate ligament, the blade tip portion 143 can easily approach the affected area 200.

The blade tip portion 143 that is the treating region is disposed at a position on a side reverse to the bending direction of the central axis C0 of the curving section 105. Consequently, the blade tip portion 143 can always be disposed within a projection area of the probe main body section 31. When the probe main body section 31 is inserted into the thin tubular member, the blade tip portion 143 can be prevented from abutting on the inner peripheral surface of the tubular member. Furthermore, it is possible to improve the approaching properties of the blade tip portion 143 even to any regions of the femur.

The treating section 130 is a thin distal portion of the curving section 105. A height of the distal portion of the treating section 130 (the projecting end of the projecting portion 137) is shorter than a width of the treating section 130, and hence strength of the treating section 130 can be acquired in a state where the treating section 130 is thin. The strength is acquired, and hence even when an amplitude V of the longitudinal vibration is enlarged in the tapered section 101, the treating section 130 can be prevented from breaking. Furthermore, in the state where the breakage is prevented, the hard affected area 200, e.g., a bone or the like can be treated by use of the enlarged amplitude V of the longitudinal vibration. Furthermore, the treating section 130 is thin, and hence the treating section 130 can easily approach the affected area 200.

The bending start position (the second curve start position) E15 is positioned on the proximal side with respect to the bending start position (the first curve start position) E14. Consequently, the space 145 can be formed as an escaping portion, and hence the approaching properties to the affected area 200 can improve in the narrow cavity. Specifically, for example, the lower surface of the femur as the affected area 200 is treated. When the space 145 is formed, for example, the opposite surface 31*c* can be prevented from abutting on an upper surface of the tibia which faces the lower surface of the femur. That is, the area other than the affected area 200 can be prevented from being unintentionally treated, and prevented from being damaged. Further, the ultrasonic probe 8 can easily access the affected area 200 even in the narrow space. Furthermore, the distal portion of the curving section 105 can be thinned and lightened, and the treatment efficiency in the narrow cavity can improve.

The bending start positions E14 and E15 are positioned on a distal portion side of the curving section 105 with respect to the most distal vibration node N3. Consequently, the amplitude V of the longitudinal vibration which is enlarged in the tapered section 101 can be transmitted to the blade tip portion 143, and the treatment efficiency can improve.

The distal portion of the probe main body section 31 can be tapered by the constricted region, the parallel region and the intersecting region, and the approaching properties can improve. Furthermore, the space 145 as the escaping portion can be formed, and hence the treatment efficiency in the narrow cavity can improve. Specifically, it is defined that, for example, the lower surface of the femur of the affected area 200 is treated. Thus, the space 145 is formed, so that, for example, the opposite surface 31*c* can be prevented from abutting on the upper surface of the tibia which faces the lower surface of the femur. That is, the area other than the affected area 200 can be prevented from being unintentionally treated, and can be prevented from being damaged. Further, the ultrasonic probe 8 can easily access the affected area 200 even in the narrow space. Furthermore, the distal portion of the curving section 105 can be thinned and lightened, and the treatment efficiency in the narrow cavity can improve.

In a case where the affected area 200 is hard as in, for example, the bone, it is necessary to enlarge the amplitude V of the longitudinal vibration. In the present embodiment, the amplitude V of the longitudinal vibration can securely be enlarged by the tapered section 101 including the narrowed region.

The part 135*a* including the blade tip portion 143 tilts at the angle θ55 relative to the longitudinal axis C toward the part 134*a* with the blade tip portion 143 being a center. Consequently, when the probe main body section 31 advances and retreats along the longitudinal axis C direction, for example, a side surface of the affected area 200 which is in the form of a curved surface can be treated by the part 135*a* including the blade tip portion 143. Furthermore, the affected area 200 is cut by the part 135*a*, so that a region abraded by the blade tip portion 143 is prevented from being only concaved and a stepped area is prevented from being formed in the circumferential surface of the affected area 200.

The part 131*a*, the part 135*a* and the part 134*a* form the projecting portion 137, i.e., the distal side of the blade tip portion (the projecting end) 143 in the projecting portion 137 is formed in two steps. Consequently, in the present embodiment, it is possible to acquire thickness and strength of the treating section 130 as compared with a case where the tilt does not change in a region located on the distal side from the blade tip portion 143. Furthermore, a length of the cutting surface (the treating surface) is 25% or more of the longitudinal dimension L57 from the blade tip portion 143 to the distal end E50 of the curving section 105 (the distal end of the part 134*a*). Consequently, it is possible to acquire thickness and strength of the projecting portion 137 (the treating section 130). Thus, the strength is acquired, and hence even when the amplitude V of the longitudinal vibration is enlarged in the tapered section 101, it is possible to prevent breakage of the projecting portion 137. Further, in the state where the breakage is prevented, it is possible to treat the hard affected area 200, e.g., the bone or the like by use of the enlarged amplitude V of the longitudinal vibration.

In the present embodiment, the tapered section 101 and the relay extending section 103 are arranged, and a predetermined length is acquired. Consequently, even when the amplitude is enlarged, it is possible to prevent stress from being concentrated on a predetermined region of the distal end constituting section 31*a*, and it is possible to disperse the stress in the whole distal constituting section 31*a*.

FIG. 7 shows the amplitude V of the longitudinal vibration and stress σ due to the ultrasonic vibration, between the second distal vibration antinode A3 and the most distal vibration antinode A2 in a state where the vibrating body unit 20 longitudinally vibrates in the established frequency range. In FIG. 7, an abscissa shows a position in a longitudinal axis direction and an ordinate shows the amplitude V and the stress σ. Furthermore, in FIG. 7, a solid line shows change of the amplitude V of the longitudinal vibration and a one-dot chain line shows change of the stress σ.

As shown in FIG. 7, in a state where the vibrating body unit 20 longitudinal vibrates in the established frequency range, the tapered section 101 is positioned on the distal side with respect to the most distal vibration node N3, and the amplitude V of the longitudinal vibration is enlarged in the tapered section 101. For example, the longitudinal vibration in which the amplitude at the vibration antinode is 80 μm is enlarged into the longitudinal vibration in which the amplitude at the vibration antinode is 140 μm or more and 150 μm or less by the tapered section 101. Furthermore, the stress σ due to the ultrasonic vibration increases at the vibration node and in a portion in which a sectional area perpendicular to a transmitting direction of the ultrasonic vibration decreases, and the stress becomes zero at the vibration antinode. Therefore, as shown in FIG. 7, the stress σ increases between the vibration node N3 and the narrowing end position S5 that is a distal end of the tapered section 101.

Here, in the present embodiment, a dimension from the proximal end (E9) of the tapered section 101 to the narrowing end position S5 in the longitudinal axis direction is larger than a ⅛ wavelength (λ/8) in the state where the vibrating body unit 20 longitudinally vibrates in the established frequency range. Further, in the tapered section 101, the longitudinal dimension L54 between the proximal end (E9) and the constricting end position S6 in the longitudinal axis direction is also larger than the ⅛ wavelength in the state where the vibrating body unit 20 longitudinally vibrates in the established frequency range. The dimension from the proximal end (E9) of the tapered section 101 to the narrowing end position S5 (the narrowing end position S6) in the longitudinal axis direction increases, so that the stress σ due to the ultrasonic vibration is kept to be substantially uniform along the total length between the vibration node N3 and the narrowing end position S5 of the tapered section 101. That is, between the vibration node N3 and the narrowing end position S5 of the tapered section 101, the stress is effectively prevented from locally increasing (i.e., generation of a peak is effectively prevented). For example, in a certain example, even when the longitudinal vibration (of, e.g., 80 μm) in which the amplitude at the vibration antinode increases is transmitted to the proximal end (E9) of the tapered section 101, the stress σ is kept to be substantially uniform at about 300 Mpa between the vibration node N3 and the narrowing end position S5 of the tapered section 101 in the state where the vibrating body unit 20 longitudinally vibrates in the established frequency range (e.g., 46 kHz or more and 48 kHz or less). That is, in the present embodiment, the stress is prevented from locally increasing up to about 700 Mpa between the vibration node N3 and the narrowing end position S5 of the tapered section 101 (e.g., at the narrowing end position S5 that is the distal end of the tapered section 101). The stress σ is prevented from locally increasing, and hence it is possible to effectively prevent the ultrasonic probe 8 from breaking due to the ultrasonic vibration.

In the present embodiment, in the case where the hard affected area 200, e.g., the bone or the like is treated with the ultrasonic probe 8 by use of the ultrasonic vibration, it is necessary to enlarge the amplitude V of the longitudinal vibration in the tapered section 101, and it is necessary to press the blade tip portion 143 onto the affected area 200. During the treatment, the tapered section 101 including the narrowed region and the curving section 105 would break due to the enlarged amplitude V and pressing. In the present embodiment, the longitudinal dimension L54 is larger than the ⅛ wavelength in the state where the vibrating body unit 20 of the ultrasonic probe 8 longitudinally vibrates. The constricted region and the treating section 130 are arranged in a ¼ wavelength in the state where the vibrating body unit 20 longitudinally vibrates. Consequently, the stress is dispersed in the longitudinal dimension L54, that is, the stress is prevented from locally increasing as described above. Furthermore, the stress decreases in the relay extending section 103 and the curving section 105. Therefore, it is possible to effectively prevent the ultrasonic probe 8 from breaking due to the ultrasonic vibration, and the enlargement of the amplitude V is compatible with the prevention of the breakage.

In the present embodiment, the probe main body section 31 and the distal constituting section 31a are formed so that any stepped areas are not formed, and the distal constituting section 31a is only narrowed. Consequently, it is possible to inhibit generation of cavitation, and it is possible to prevent the cavitation from disturbing an observation view field when the affected area 200 is treated. In other words, an operator's visibility can improve. Further, it is possible to prevent the cavitation from damaging the affected area 200, and it is possible to prevent the cavitation from damaging the probe main body section 31 and the distal constituting section 31a.

The corners R51 are formed in the periphery of the sectional area uniform portion 120, the corner R52 is formed in the curved surface portion 132a, and the corner R53 and the corner R54 are formed in the curved surface portion 132b of the part 130b. Consequently, in the sectional area uniform portion 120 and the curved surface portion 132b, it is possible to inhibit the generation of the cavitation and it is possible to prevent the cavitation from damaging the affected area 200. Furthermore, in the above description, even when the sectional area uniform portion 120, the curved surface portion 132a and the curved surface portion 132b come in contact with the affected area 200, the corners R51, R52, R53 and R54 can prevent damages on the affected area 200.

Second Embodiment

In the present embodiment, differences from the first embodiment will only be described with reference to FIG. 9, FIG. 10 and FIG. 11.

It is preferable that a total length L1 is 183.2 mm. It is preferable that a longitudinal dimension L2 is 177.2 mm. It is preferable that a longitudinal dimension L53 is 10 mm.

Figure 9:
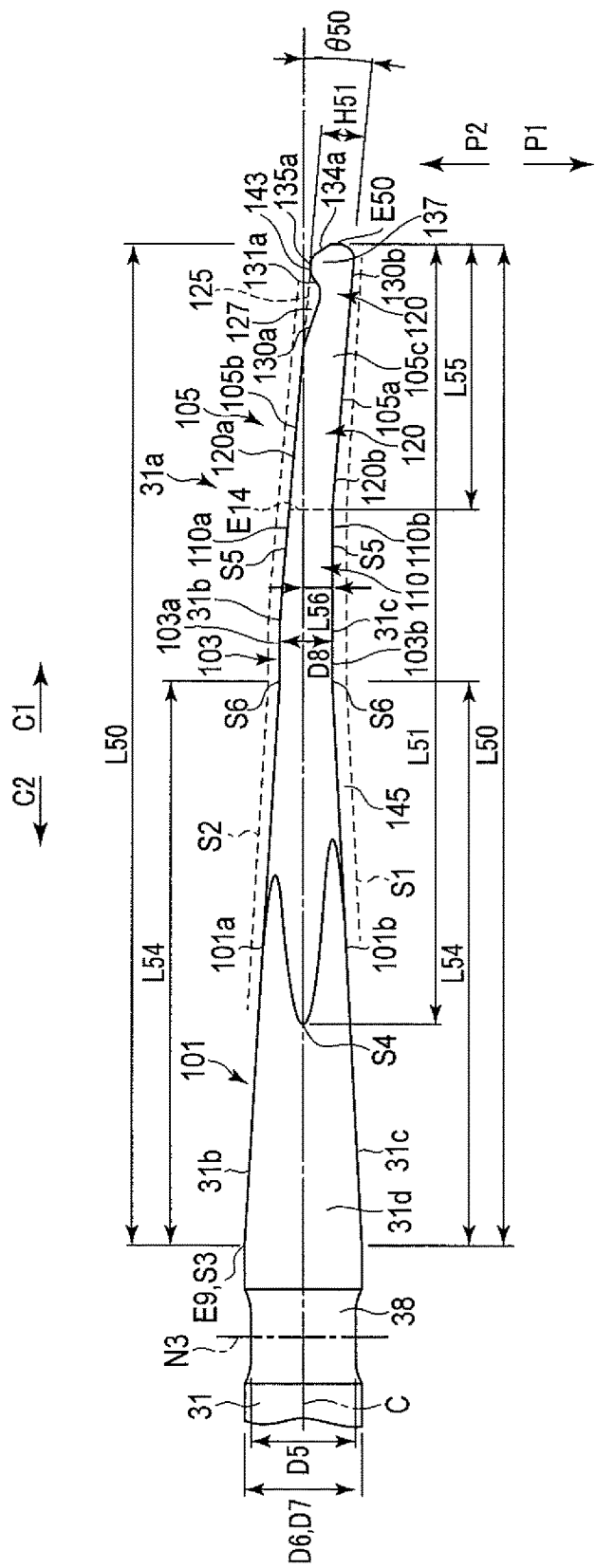
FIG. 9 is a schematic view of a distal portion of an ultrasonic probe according to a second embodiment seen from a first width direction side.
Figure 10:
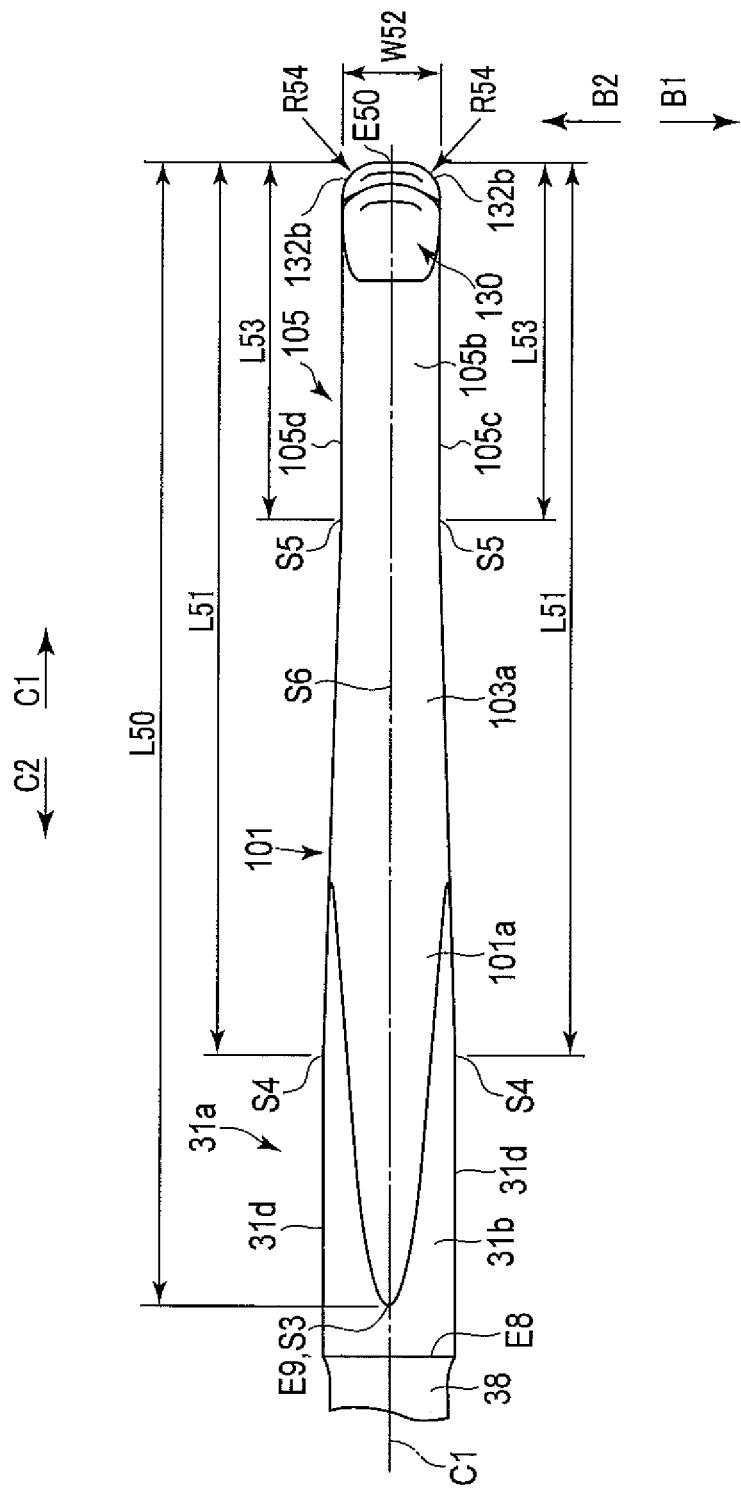
FIG. 10 is a schematic view of the distal portion of the ultrasonic probe according to the second embodiment seen from a second intersecting direction side.

As shown in FIG. 9 and FIG. 11, in a curved surface portion 132a, for example, a corner radius R52 is 0.4 mm. It is preferable that a height H52 of a part 131a relative to a part 130a is 0.7 mm.

As shown in FIG. 11, when seen from a reference surface 31b side, a corner radius R54 of each curved surface portion 132b is 1 mm.

As shown in FIG. 11, an angle θ56 formed between a part 135a and a perpendicular direction perpendicular to a planar direction of the part 130a is 70 degrees. It is preferable that a longitudinal dimension L60 of the part 135a is 0.2 mm.

As shown in FIG. 11, the curved surface portion 132b is curved smoothly in a circular shape along a longitudinal axis C and toward the rear, and is continuous with a part 134*a* included in the reference surface 31*b* (a second curved outer surface 105*b*). In a cross section perpendicular to width directions (a first width direction and a second width direction), a curved portion 132*c* between the curved surface portion 132*b* and the part 134*a* has a corner radius R55 and the corner radius R55 is 0.4 mm. The part 134*a* is bent at an angle θ57 relative to the longitudinal axis C. The angle θ57 is 55 degrees.

As shown in FIG. 11, the part 134*a* is curved smoothly in a circular shape along the longitudinal axis C and toward the rear, and is continuous with the part 135*a*. In the cross section perpendicular to the width direction, a curved portion 132*d* between the part 134*a* and the part 135*a* has a corner radius R56, and the corner radius R56 is 0.4 mm. The part 135*a* is bent at an angle θ58 relative to the longitudinal axis C. The angle θ58 is 25 degrees.

As shown in FIG. 11, it is preferable that a longitudinal dimension L61 in a longitudinal direction between a distal end E50 formed in the curved surface portion 132*b* (a distal end of the part 134*a*) and a blade tip portion 143 is 0.6 mm.

As shown in FIG. 11, the part 135*a* is bent relative to the blade tip portion 143 in a bending direction of a part 120*a* about the blade tip portion 143 so that the whole surface of the part 135*a* including the blade tip portion 143 is disposed on an extension line 125 of the part 120*a*. Alternatively, the part 135*a* is bent relative to the blade tip portion 143 in the bending direction of the part 120*a* about the blade tip portion 143 so that the whole surface of the part 135*a* including the blade tip portion 143 is positioned on a side opposite to the longitudinal axis C with respect to a boundary that is the extension line 125 of the part 120*a*. That is, the whole surface of the part 135*a* including the blade tip portion 143 is disposed on the same plane as the extension line 125 or on a plane below the extension line 125.

As shown in FIG. 11, each of the part 131*a* and the part 135*a* including the blade tip portion 143 is formed into a circular shape. In this case, it is preferable that a longitudinal dimension L62 between a central position to form a circle of the blade tip portion 143 and the blade tip portion 143 is 2 mm. The central position is formed on a part 130*a* side (a proximal side).

In the present embodiment, it is possible to obtain effects similar to those of the first embodiment. In the present embodiment, in place of a boundary portion 141, the curved portion 132*d* that does not have any edges is formed between the part 135*a* and the part 134*a*, and the curved portions 132*c* and 132*d* can further inhibit generation of cavitation. Each of the part 131*a* and the part 135*a* including the blade tip portion 143 is formed into the circular shape. Consequently, treating properties to an affected area 200 can improve.

Third Embodiment

Next, a third embodiment of the present invention will be described with reference to FIG. 12 to FIG. 20. In the third embodiment, the constitution of the first embodiment is modified as follows. It is to be noted that the same components as in the first embodiment are denoted with the same reference signs to omit their descriptions.

Also in the present embodiment, a probe main body section 31 includes a horn portion 35, a horn portion 36, a sectional area increasing portion 37 and a supported portion 38 in the same manner as in the first embodiment. In a certain example, it is preferable that a total length L1 of an ultrasonic probe 8 is 182.9 mm. Furthermore, in the certain example, it is preferable that a longitudinal dimension L2 from a distal end of the ultrasonic probe 8 to an abutment surface 33 (a proximal end of the probe main body section 31) is 177.5 mm.

Furthermore, in the certain example of the present embodiment, it is preferable that a longitudinal dimension L3 from the abutment surface 33 to a proximal end (a vibration input end) E1 of the horn portion 35 in a longitudinal axis direction is 29 mm. Furthermore, it is preferable that a horn longitudinal dimension (a first horn longitudinal dimension) L4 of the horn portion (a first horn portion) 35 from the proximal end (the vibration input end) E1 to a distal end (a vibration output end) E2 in the longitudinal axis direction is 20 mm. Also in the present embodiment, in the horn portion 35, an outer diameter of the probe main body section 31 decreases from an outer diameter D1 to an outer diameter D2 toward a distal side. In the certain example, it is preferable that the outer diameter D1 is 7 mm. Further, it is preferable that the outer diameter D2 is 3.8 mm.

Furthermore, in the certain example of the present embodiment, it is preferable that a longitudinal dimension L5 from the abutment surface 33 to a proximal end (a vibration input end) E3 of the horn portion 36 in the longitudinal axis direction is 88.1 mm. Further, it is preferable that a horn longitudinal dimension (a second horn longitudinal dimension) L6 of the horn portion (a second horn portion) 36 from the proximal end (the vibration input end) E3 to a distal end (a vibration output end) E4 in the longitudinal axis direction is 14 mm. Also in the present embodiment, in the horn portion 36, the outer diameter of the probe main body section 31 decreases from the outer diameter D2 to an outer diameter D3 toward the distal side. In the certain example, it is preferable that the outer diameter D3 is 2.7 mm.

In the certain example of the present embodiment, it is preferable that a longitudinal dimension L7 from the abutment surface 33 to a distal end (a vibration output end) E6 of the sectional area increasing portion 37 in the longitudinal axis direction is 116.7 mm. An extending dimension L8 of the sectional area increasing portion 37 from a proximal end (a vibration input end) E5 to the distal end (the vibration output end) E6 in the longitudinal axis direction is small. Also in the present embodiment, in the sectional area increasing portion 37, the outer diameter of the probe main body section 31 increases from the outer diameter D3 to an outer diameter D4 toward the distal side. In the certain example, the outer diameter D4 is about the same as the outer diameter D2 at the proximal end E3 of the horn portion 36, and it is preferable that the outer diameter D4 is 3.8 mm.

In the certain example of the present embodiment, it is preferable that a longitudinal dimension L9 from the distal end E6 of the sectional area increasing portion 37 to a proximal end E7 of the supported portion 38 in the longitudinal axis direction is 24.1 mm. Furthermore, in the supported portion 38, an extending dimension L10 from the proximal end E7 to a distal end E8 in the longitudinal axis direction is 3 mm. Further, in the supported portion 38, an outer diameter of a proximal portion decreases from the outer diameter D4 to an outer diameter D5 and an outer diameter of a distal portion increases from the outer diameter D5 to an outer diameter D6. In the certain example, the outer diameter D5 is slightly (about 0.4 mm) smaller than the outer diameter D4. Further, the outer diameter D6 is about the same as the outer diameter D4, and it is preferable that the diameter D6 is 3.8 mm.

Furthermore, in a state where a vibrating body unit 20 longitudinally vibrates in an established frequency range (46 kHz or more and 48 kHz or less), a vibration node N1 is positioned at the proximal end E1 of the horn portion 35 or in the vicinity of the proximal end E1, and a vibration node N2 is positioned at the proximal end E3 of the horn portion 36 or in the vicinity of the proximal end E3. Furthermore, in the state where the vibrating body unit 20 longitudinally vibrates in the established frequency range, a vibration antinode A3 is positioned in the sectional area increasing portion 37, and a vibration antinode (the most distal vibration antinode) A2 is positioned at the distal end of the ultrasonic probe 8. Further, in the state where the vibrating body unit 20 longitudinally vibrates in the predetermined frequency range, a vibration node (the most distal vibration node) N3 that is one of the vibration nodes of the longitudinal vibration is positioned in the supported portion 38. According to the above-mentioned constitution, also in the certain example of the present embodiment, the longitudinal vibration in which an amplitude at the vibration antinode is 80 µm occurs at a distal end E9 of the probe main body section 31, in a state where the longitudinal vibration in which the amplitude at the vibration antinode is 18 µm is transmitted to the proximal end (the abutment surface 33) of the probe main body section 31.

Figure 13:
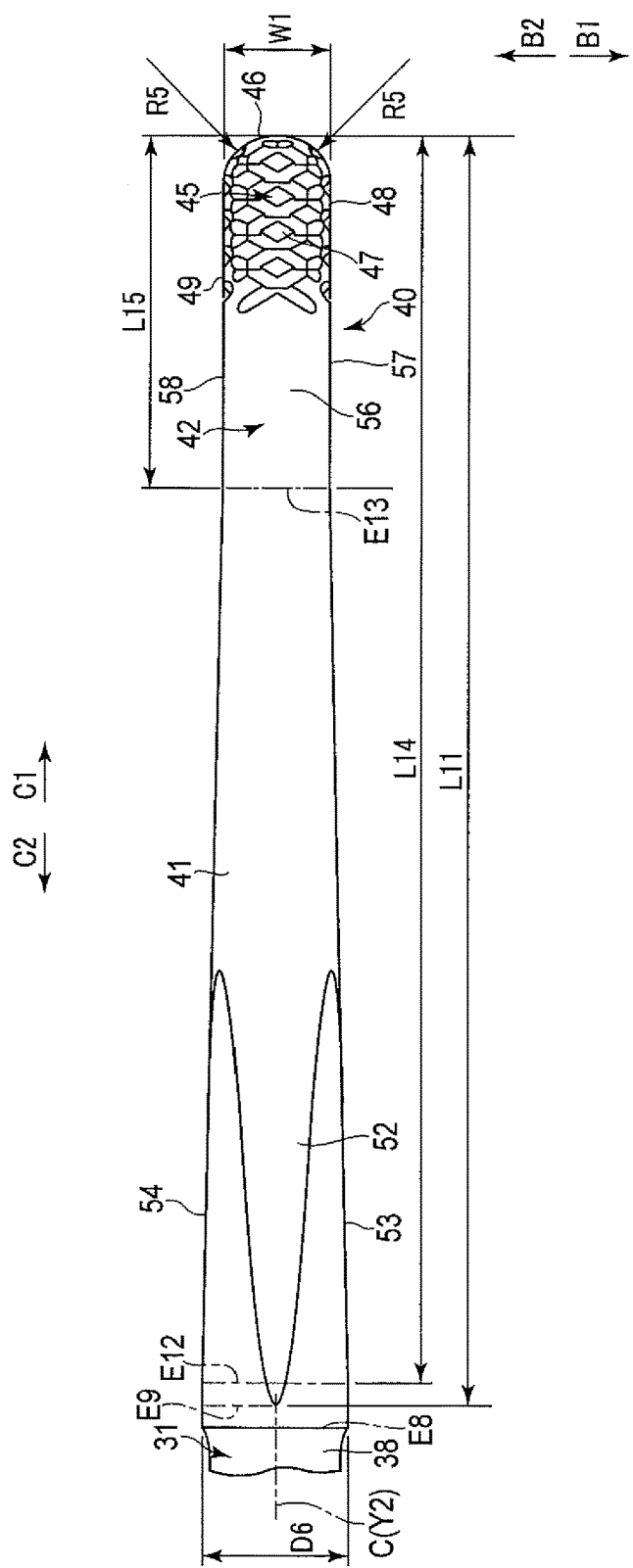
FIG. 13 is a schematic view of the distal portion of the ultrasonic probe according to the third embodiment seen from a second intersecting direction side.

FIG. 12 and FIG. 13 are views showing a constitution of a distal portion of the ultrasonic probe 8. FIG. 12 is a view of the ultrasonic probe 8 seen from a first width direction side (an arrow B1 side of FIG. 13), and FIG. 13 is a view of the ultrasonic probe 8 seen from a second intersecting direction side (an arrow P2 side of FIG. 12). It is to be noted that in FIG. 12, a range shown by a broken line S1 and a broken line S2 projects from a distal end of a sheath 7 toward the distal side.

As shown in FIG. 12 and FIG. 13, also in the present embodiment, the distal end E9 of the probe main body section 31 is positioned on the distal side with respect to the distal end E8 of the supported portion 38. Additionally, a distance between the distal end E8 of the supported portion 38 and the distal end E9 of the probe main body section 31 in the longitudinal axis direction is small and is about 0.6 mm in the certain example.

In the present embodiment, a tapered section (a sectional area decreasing portion) 41 is continuous on the distal side of the probe main body section 31. In the tapered section (a third horn portion) 41, a sectional area perpendicular to a longitudinal axis C decreases toward the distal side. A proximal end of the tapered section 41 is continuous with the distal end E9 of the probe main body section 31. Therefore, the distal end E9 of the probe main body section 31 becomes a boundary position between the probe main body section 31 and the tapered section 41. The ultrasonic probe 8 has a longitudinal dimension L11 from the distal end to the proximal end (E9) of the tapered section 41 in the longitudinal axis direction. In the certain example, it is preferable that the longitudinal dimension L11 is 32.5 mm.

The tapered section 41 includes a first narrowed outer surface 51 facing a first intersecting direction side (an arrow P1 side of FIG. 12). In the tapered section 41, a distance (a first distance) δ from the longitudinal axis C to the first narrowed outer surface 51 in a first intersecting direction decreases from a proximal side toward the distal side, between the proximal end (E9) and a first narrowing end position (a first distance decreasing end position) E10 in the longitudinal axis direction. The first narrowing end position E10 is positioned on the distal side with respect to the proximal end (E9) of the tapered section 41. Consequently, the tapered section 41 has a first narrowing dimension (a first distance decreasing dimension) L12 between the proximal end (E9) and the first constricting end position E10 in the longitudinal axis direction. In the certain example, it is preferable that the first narrowing dimension L12 is 18 mm. In the present embodiment, the proximal end (E9) of the tapered section 41 becomes a proximal end of the first narrowed outer surface 51, and the first narrowing end position E10 becomes a distal end of the first narrowed outer surface 51.

Furthermore, the tapered section 41 includes a second narrowed outer surface 52 facing the second intersecting direction side. On the tapered section 41, a distance (a second distance) δ' from the longitudinal axis C to the second narrowed outer surface 52 in a second intersecting direction decreases from the proximal side toward the distal side, between the proximal end (E9) and a second narrowing end position (a second distance decreasing end position) E11 in the longitudinal axis direction. The second narrowing end position E11 is positioned on the distal side with respect to the first narrowing end position E10. Consequently, the tapered section 41 has a second narrowing dimension (a second distancing decrease dimension) L13 that is larger than the first narrowing dimension L12, between the proximal end (E9) and the second narrowing end position E11 in the longitudinal axis direction. In the certain example, it is preferable that the second constricting dimension L13 is 23 mm. In the present embodiment, the proximal end (E9) of the tapered section 41 becomes a proximal end of the second narrowed outer surface 52, and the second narrowing end position E11 becomes a distal end of the second constricted outer surface 52. Consequently, in the tapered section 41, the distal end of the first constricted outer surface 51 (the first constricting end position E10) is positioned on a proximal side as compared with the distal end of the second narrowed outer surface 52 (the second narrowing end position E11), and the distal end of the first narrowed outer surface 51 is disposed away from the distal end of the second narrowed outer surface 52 in the longitudinal axis direction.

Due to the above-mentioned constitution, in the tapered section 41, a thickness (a dimension) T of the ultrasonic probe 8 in the first intersecting direction and the second intersecting direction decreases toward the distal side, between the proximal end (E9) and the second narrowing end position E11 in the longitudinal axis direction. Therefore, the proximal end (E9) of the tapered section 41 becomes a thickness decreasing start position, and the second narrowing end position E11 becomes a thickness decreasing end position. Furthermore, in projection from a first width direction (one side of a width direction), a first narrowing angle α1 that is a narrowing angle (an acute angle) of the first narrowed outer surface 51 relative to the longitudinal axis direction is larger than a second narrowing angle α2 that is a narrowing angle (an acute angle) of the second narrowed outer surface 52 relative to the longitudinal axis direction, and the first narrowing angle is different from the second narrowing angle α2.

Furthermore, the tapered section 41 includes a third narrowed outer surface 53 directed in the first width direction, and a fourth narrowed outer surface 54 facing a second width direction (an arrow B2 side of FIG. 13). In the tapered section 41, between a width decreasing start position E12 and a width decreasing end position E13 in the longitudinal axis direction, a distance from the longitudinal axis C to the third narrowed outer surface 53 in the first width direction and a distance from the longitudinal axis C to the fourth narrowed outer surface 54 in the second width direction decrease from the proximal side toward the distal side. Consequently, in the tapered section 41, a width (a dimension) W of the ultrasonic probe 8 in the first width direction and the second width direction decreases toward the distal side, between the width decreasing start position E12 and the width decreasing end position E13 in the longitudinal axis direction. The ultrasonic probe 8 has a longitudinal dimension L14 from the distal end to the width decreasing start position E12 in the longitudinal axis direction. The longitudinal dimension L14 is smaller than the longitudinal dimension L11 from the distal end of the ultrasonic probe 8 to the proximal end (E9) of the tapered section 41 in the longitudinal axis direction. Therefore, the width decreasing start position E12 is positioned on the distal side with respect to the proximal end (E9) of the tapered section 41. However, the distance between the proximal end (E9) of the tapered section 41 and the width decreasing start position E12 in the longitudinal axis direction is small. In the certain example, it is preferable that the longitudinal dimension L14 is 32 mm. Further, in this example, the distance between the proximal end (E9) of the tapered section 41 and the width decreasing start position E12 in the longitudinal axis direction is about 0.5 mm. In the present embodiment, the width decreasing start position E12 becomes a proximal end of each of the third constricted outer surface 53 and the fourth constricted outer surface 54, and the width decreasing end position E13 becomes a distal end of each of the third narrowed outer surface 53 and the fourth narrowed outer surface 54.

The ultrasonic probe 8 has a longitudinal dimension L15 from the distal end to the width decreasing end position E13 in the longitudinal axis direction. In the present embodiment, the width decreasing end position E13 is positioned on the distal side with respect to the second narrowing end position E11. Further, the width decreasing end position E13 becomes a distal end of the tapered section 41. However, a distance between the second narrowing end position (the distal end of the second narrowed outer surface 52) E11 and the width decreasing end position E13 in the longitudinal axis direction is small. In the certain example, it is preferable that the longitudinal dimension L15 is 9 mm. Further, in this example, the distance between the second narrowing end position E11 and the width decreasing end position E13 in the longitudinal axis direction is about 0.5 mm.

The distance (the first distance) δ from the longitudinal axis C to the first narrowed outer surface 51 (an outer peripheral surface of the ultrasonic probe 8) in the first intersecting direction (a first perpendicular direction) decreases down to a distance δ1, between the proximal end (E9) of the tapered section 41 and the first narrowing end position E10 in the longitudinal axis direction. Therefore, at the first narrowing end position (the distal end of the first narrowed outer surface 51) E10, the ultrasonic probe 8 has the distance (the first distance) δ1 from the longitudinal axis C to the first narrowed outer surface 51 toward the first intersecting direction. The distance δ1 is smaller than a value of ½ of the outer diameter D6 at the distal end E9 of the probe main body section 31. In the certain example, the distance δ1 is 0.45 mm or more and 0.5 mm or less.

Between the proximal end (E9) of the tapered section 41 and the second narrowing end position E11 in the longitudinal axis direction, the thickness (the dimension) T of the ultrasonic probe 8 in the first intersecting direction and the second intersecting direction decreases down to a thickness T1. Therefore, at the second narrowing end position (the distal end of the second narrowed outer surface 52) E11, the ultrasonic probe 8 has the thickness T1 in the first intersecting direction (the first perpendicular direction) and the second intersecting direction (a second perpendicular direction). The thickness T1 is smaller than the outer diameter D6 at the distal end E9 of the probe main body section 31. In the certain example, it is preferable that the thickness T1 is 1.65 mm.

Between the width decreasing start position E12 and the width decreasing end position E13 in the longitudinal axis direction, the width (the dimension) W of the ultrasonic probe 8 in the first width direction and the second width direction decreases down to a width dimension W1. Therefore, at the width decreasing end position (the distal end of each of the third constricted outer surface 53 and the fourth constricted outer surface 54) E13, the ultrasonic probe 8 has the width dimension W1 in the first width direction and the second width direction. The width dimension W1 is smaller than the outer diameter D6 at the distal end E9 of the probe main body section 31. In the certain example, it is preferable that the width dimension W1 is 2.8 mm.

The tapered section 41 is constituted as described above, and hence in the tapered section 41, the sectional area perpendicular to the longitudinal axis C decreases toward the distal side. In the state where the vibrating body unit 20 longitudinally vibrates in the established frequency range (e.g., 46 kHz or more and 48 kHz or less), the vibration node (the most distal vibration node) N3 that is one of the vibration nodes of the longitudinal vibration is positioned in the supported portion 38, and is positioned in the vicinity of the proximal end (E9) of the tapered section 41. Further, in the state where the vibrating body unit 20 longitudinally vibrates in the predetermined frequency range, each of the vibration antinodes of the longitudinal vibration is positioned away from the tapered section 41 in the longitudinal axis direction. Consequently, in the tapered section 41 in which the sectional area decreases toward the distal side, the amplitude of the longitudinal vibration (ultrasonic vibration) is enlarged. In the certain example, in a case where the longitudinal vibration in which the amplitude in the tapered section 41 is 80 μm is transmitted, the amplitude of the longitudinal vibration at the distal end of the ultrasonic probe 8 is 140 μm or more and 150 μm or less.

Furthermore, in the present embodiment, a tapering dimension of the tapered section 41 from the proximal end (E9) to the distal end (E13) in the longitudinal axis direction is larger than a ⅛ wavelength (λ/8) in the state where the vibrating body unit 20 longitudinally vibrates in the established frequency range. That is, the ⅛ wavelength (λ/8) in the state where the vibrating body unit 20 longitudinally vibrates in the established frequency range is smaller than the tapering dimension of the tapered section 41 from the proximal end (E9) to the distal end (E13) in the longitudinal axis direction. In the certain example, in the state where the vibrating body unit 20 longitudinally vibrates at 46 kHz or more and 48 kHz or less (in the established frequency range), a ¼ wavelength (λ/4) from the vibration node (the most distal vibration node) N3 to the vibration antinode (the most distal vibration antinode) A2 is 34 mm or more and 35 mm or less. On the other hand, in this example, the tapering dimension of the tapered section 41 from the proximal end (E9) to the distal end (E13) in the longitudinal axis direction is about 23.5 mm, and is larger than the ⅛ wavelength in the state where the vibrating body unit 20 longitudinally vibrates at 46 kHz or more and 48 kHz or less (in the predetermined frequency range). Furthermore, in the tapered section 41, the first narrowing dimension L12 between the proximal end (E9) and the first narrowing end position E10 in the longitudinal axis direction is also 17.9 mm or more and 18 mm or less. Therefore, the first narrowing dimension L12 (i.e., the dimension of the first constricted outer surface 51 in the longitudinal axis direction) is also larger than the ⅛ wavelength in the state where the vibrating body unit 20 longitudinally vibrates at 46 kHz or more and 48 kHz or less (in the established frequency range). It is to be noted that the first narrowing end position E10 is positioned most proximally among the positions (e.g., E10, E11 and E13) at which the narrowing ends on an outer peripheral surface of the tapered section 41 (the narrowed outer surfaces 51 to 54).

In the ultrasonic probe 8, a curved extending section 40 is disposed on the distal side with respect to the tapered section 41 (and the probe main body section 31). The curved extending section 40 extends in a state of curving relative to the probe main body section 31 and the tapered section 41 (i.e., the longitudinal axis C) toward the first intersecting direction side. The curved extending section 40 includes a first curved outer surface 55 facing the first intersecting direction side (a side on which the curved extending section 40 curves), and a second curved outer surface 56 directed on the second intersecting direction side (a side opposite to the side on which the curve extending section 40 curves). Furthermore, the curved extending section 40 includes a third curved outer surface 57 facing the first width direction side, and a fourth curved outer surface 58 facing on a second width direction side. It is to be noted that by transmitting the ultrasonic vibration to the curved extending section 40 from the probe main body section 31 through the tapered section 41, the curved extending section 40 longitudinally vibrates together with the probe main body section 31 and the tapered section 41 in the established frequency range.

In projection from the first width direction (one side of the width direction), in the first curved outer surface 55 of the curved extending section 40, a region located on the distal side with respect to a first curve start position E14 curves relative to the longitudinal axis direction (the probe main body section 31) toward the first intersecting direction side. Furthermore, in the projection from the first width direction, in the second curved outer surface 56 of the curved extending section 40, a region located on the distal side with respect to a second curve start position E15 curves relative to the longitudinal axis direction toward the first intersecting direction side. That is, the first curved outer surface 55 starts curving relative to the longitudinal axis C in the first intersecting direction side at the first curve start position E14, and the second curved outer surface 56 starts curving relative to the longitudinal axis C toward the first intersecting direction side at the second curve start position E15. In the present embodiment, the second curve start position (a proximal end of the second curved outer surface 56) E15 is positioned on the distal side with respect to the first curve start position (a proximal end of the first curved outer surface 55) E14, and is positioned away from the first curve start position E14 in the longitudinal axis direction. Additionally, in the present embodiment, a distance between the first curve start position E14 and the second curve start position E15 in the longitudinal axis direction is small, and is about 0.3 mm in the certain example. Furthermore, in a certain modification different from the present embodiment, the first curve start position (the proximal end of the first curved outer surface 55) E14 may be positioned on the distal side with respect to the second curve start position (the proximal end of the second curved outer surface 56) E15 in the curved extending section 40.

The curved extending section 40 extends toward the distal side from the first curve start position E14 which is the proximal end (a curve proximal end). The ultrasonic probe 8 has a longitudinal dimension L16 from the distal end to the proximal end (E14) of the curved extending section 40 in the longitudinal axis direction. The longitudinal dimension L16 is smaller than the longitudinal dimension L15 from the distal end of the ultrasonic probe 8 to the width decreasing end position E13 in the longitudinal axis direction. Consequently, the proximal end (E14) of the curved extending section 40 is positioned on the distal side with respect to the width decreasing end position E13. In the certain example, the longitudinal dimension L16 is 8.4 mm or more and 8.5 mm or less.

Furthermore, in the ultrasonic probe 8, a relay extending section 43 is continuous between the tapered section 41 and the curved extending section 40 in the longitudinal axis direction. The relay extending section 43 extends from the width decreasing end position E13 (the distal end of the tapered section 41) to the first curve start position E14 (a proximal end of the curved extending section 40). Here, a distance between the width decreasing end position E13 and the proximal end (E14) of the curved extending section 40 in the longitudinal axis direction is small. Consequently, a dimension of the relay extending section 43 in the longitudinal axis direction is small. In the certain example, the dimension of the relay extending section 43 in the longitudinal axis direction is about 0.5 mm.

A first axis parallel outer surface 61 directed in the first intersecting direction is continuous between the first narrowed outer surface 51 and the first curved outer surface 55 in the longitudinal axis direction. The first axis parallel outer surface 61 extends in parallel (substantially parallel) with the longitudinal axis C between the first narrowing end position E10 and the first curve start position E14. Therefore, the first constricting end position E10 becomes a proximal end of the first axis parallel outer surface 61 and the first curve start position E14 becomes a distal end of the first axis parallel outer surface 61. Further, the first axis parallel outer surface 61 has an extending dimension (a first extending dimension) L19 in the longitudinal axis direction. On the first axis parallel outer surface 61, the distance δ from the longitudinal axis C toward the first intersecting direction is kept to be substantially constant at the distance δ1, from the first narrowing end position E10 to the first curve start position E14.

Furthermore, a second axis parallel outer surface 62 facing the second intersecting direction is continuous between the second narrowed outer surface 52 and the second curved outer surface 56 in the longitudinal axis direction. The second axis parallel outer surface 62 extends in parallel (substantially parallel) with the longitudinal axis C, between the second narrowing end position E11 and the second curve start position E15. Therefore, the second constricting end position E11 becomes a proximal end of the second axis parallel outer surface 62, and the second curve start position E15 becomes a distal end of the second axis parallel outer surface 62. Further, the second axis parallel outer surface 62 has an extending dimension (a second extending dimension) L20 in the longitudinal axis direction. The extending dimension L19 of the first axis parallel outer surface 61 is larger than the extending dimension L20 of the second axis parallel outer surface 62. On the second axis parallel outer surface 62, the distance δ' from the longitudinal axis C toward the second intersecting direction is kept to be substantially constant from the second narrowing end position E11 to the second curve start position E15.

Due to such a constitution as described above, between the second narrowing end position E11 and the first curve start position (the proximal end of the curved extending section 40) E14 in the longitudinal axis direction, the thickness T of the ultrasonic probe 8 in the first intersecting direction and the second intersecting direction is kept to be substantially constant at the thickness T1. Furthermore, between the width decreasing end position E13 and the distal end of the ultrasonic probe 8 in the longitudinal axis direction, the width W of the ultrasonic probe 8 in the first width direction and the second width direction is kept to be substantially constant at the width dimension W1. Therefore, in the relay extending section 43 extending from the width decreasing end position E13 to the first curve start position (the proximal end of the curved extending section 40) E14, the dimension becomes substantially constant at the width dimension W1 and substantially constant at the thickness T1 along the total length in the longitudinal axis direction. Further, in the relay extending section 43, the sectional area perpendicular to the longitudinal axis C becomes substantially constant along the total length in the longitudinal axis direction.

Here, there is stipulated a reference plane (a first reference plane) Y1 passing along the longitudinal axis C and perpendicularly (substantially perpendicularly) to the first intersecting direction and the second intersecting direction. In the relay extending section 43, the distance (the first distance) δ1 from the longitudinal axis C to the first axis parallel outer surface 61 (the outer peripheral surface of the ultrasonic probe 8) toward the first intersecting direction is smaller than a value of ½ of the thickness T1 of the ultrasonic probe 8 in the first intersecting direction and the second intersecting direction. Consequently, in the tapered section 41 and the relay extending section 43, the ultrasonic probe 8 is non-symmetrical about the reference plane Y1 which is a central plane. Further, in the tapered section 41 and the relay extending section 43, a cross section gravity center in the cross section perpendicular to the longitudinal axis C shifts from the longitudinal axis C toward the second intersecting direction side. Especially, between the first narrowing end position E10 and the first curve start position E14, there increases the shift of the cross section gravity center relative to the longitudinal axis C in the second intersecting direction side. Furthermore, there is stipulated a reference plane (a second reference plane) Y2 passing along the longitudinal axis C and perpendicularly (substantially perpendicularly) to the first width direction and the second width direction. In the tapered section 41 and the relay extending section 43, the ultrasonic probe 8 is substantially symmetric about the reference plane Y2 which is a central plane.

The curved extending section 40 includes a first curved extending section 42 that extends from the first curve start position E14 at the proximal end of the curved extending section 40 toward the distal side and curving relative to the probe main body section 31 and the tapered section 41 toward the first intersecting direction side. In the projection from the first width direction (one side of the width direction), in a region of an outer peripheral surface of the first curved extending section 42 which faces the first intersecting direction side, a tangent line at the first curve start position E14 has an acute angle θ1 relative to the longitudinal axis direction. Furthermore, in the projection from the first width direction, in a region of the outer peripheral surface of the first curved extending section 42 which is directed on the second intersecting direction side, a tangent line at the second curve start position E15 has an acute angle θ2 relative to the longitudinal axis direction. The acute angle θ1 and the acute angle θ2 are larger than 0° and 10° or less. In the certain example, the acute angle θ1 is 50, whereas the acute angle θ2 is 7.5°. Consequently, the acute angle θ2 is larger than the acute angle θ1.

In the curved extending section 40, a second curved extending section 45 is continuous with the distal side of the first curved extending section 42. The second curved extending section 45 extends in a state of curving relative to the first curved extending section 42 toward the first intersecting direction side. In the projection from the first width direction (one side of the width direction), a region of an outer peripheral surface of the second curved extending section 45 which faces the first intersecting direction side extends in a circular shape of a curbing radius R1. Furthermore, in the projection from the first width direction, a region of the outer peripheral surface of the second curve extending section 45 which is directed on the second intersecting direction side extends in a circular shape of a curving radius R2.

A center O1 of each of the circle of the curving radius R1 and the circle of the curving radius R2 is positioned on the first intersecting direction side with respect to the curved extending section 40 (the ultrasonic probe 8). Consequently, in the projection from the first width direction (the second width direction), in a region of the outer peripheral surface of the second curved extending section 45 which faces the first intersecting direction side, an acute angle relative to the longitudinal axis direction increases toward the distal side. Similarly, in the projection from the first width direction (the second width direction), in a region of the outer peripheral surface of the second curved extending section 45 which is directed on the second intersecting direction side, an acute angle relative to the longitudinal axis direction increases toward the distal side. Therefore, in the second curved extending section 45, the acute angle relative to the longitudinal axis direction increases toward the distal side.

In the region of the outer peripheral surface of the second curved extending section 45 which faces the first intersecting direction side, a tangent line at a distal end has an acute angle θ3 relative to the longitudinal axis direction. Furthermore, in the region of the outer peripheral surface of the second curved extending section 45 which faces the second intersecting direction side, a tangent line at a distal end has an acute angle θ4 relative to the longitudinal axis direction. That is, at a distal end of the first curved outer surface 55, the curved extending section 40 has the acute angle θ3 relative to the longitudinal axis direction. Further, at a distal end of the second curved outer surface 56, the curved extending section 40 has the acute angle θ4 relative to the longitudinal axis direction. In the certain example, the curving radius R1 is 15 mm and the acute angle θ3 is 15°. Furthermore, the acute angle θ4 is stipulated in accordance with the curving radius R2. For example, in a case where the curving radius R2 is 12.5 mm, the acute angle θ4 is 25°, and in a case where the curving radius R2 is 16.5 mm, the acute angle θ4 is 20°. Further, in a case where the curving radius R2 is 30 mm, the acute angle θ4 is 15°. In the certain example, on the second curved outer surface 56 (the region of the outer peripheral surface of the second curved extending section 45 which faces the second intersecting direction side), the acute angle θ4 of the tangent line at the distal end relative to the longitudinal axis direction is 10° or more and 30° or less, and more preferably 20° or more and 25° or less.

Furthermore, a direction that is perpendicular (substantially perpendicular) to an extending direction and that is perpendicular (substantially perpendicular) to the width direction in the ultrasonic probe 8 is a thickness direction. In the curved extending section 40, the extending direction of the ultrasonic probe 8 is not parallel to the longitudinal axis, and hence in the curved extending section 40, the thickness direction is not parallel to the first intersecting direction and the second intersecting direction. The ultrasonic probe 8 is kept to be substantially constant at a thickness dimension T2 in the thickness direction from the second curve start position E15 to the distal end in the longitudinal axis direction. That is, between the second curve start position E15 and the distal end of the ultrasonic probe 8, the thickness dimension T2 that is a distance between the first curved outer surface 55 and the second curved outer surface 56 is kept to be substantially constant. In the certain example, the thickness dimension T2 is 1.5 mm. Therefore, the acute angles θ1 to θ4 and the curving radiuses R1 and R2 are determined in a state where the thickness dimension T2 of the ultrasonic probe 8 is substantially constant from the second curve start position E15 to the distal end.

Furthermore, the region of the outer peripheral surface of the second curved extending section 45 which faces the first intersecting direction side has a separation distance T3 from the longitudinal axis C toward the first intersecting direction at the distal end. In the certain example, it is preferable that the separation distance T3 is 1.9 mm.

The second curved extending section 45 includes a distal surface 46 that forms the distal end of the ultrasonic probe 8. In the projection from the first width direction (one side of the width direction), a portion between the first curved outer surface 55 (the region of the outer peripheral surface of the second curved extending section 45 which is directed on the first intersecting direction side) and the distal surface 46 is formed into a curved surface of a corner radius R3. Furthermore, in the projection from the first width direction, a portion between the second curved outer surface 56 (the region of the outer peripheral surface of the second curved extending section 45 which faces the second intersecting direction side) and the distal surface 46 is formed into a curved surface of a corner radius R4. In the certain example, the corner radius R3 is 0.5 mm and the corner radius R4 is 0.9 mm. Furthermore, in projection from the second intersecting direction (one side of the intersecting direction), there is formed into a curved surface of a corner radius R5 each of a portion between a third curved outer surface 57 (the region of the outer peripheral surface of the second curved extending section 45 which faces the first width direction side) and the distal surface 46 and a portion between a fourth curved outer surface 58 (the region of the outer peripheral surface of the second curved extending section 45 which is directed on the second width direction side) and the distal surface 46. In the certain example, the corner radius R5 is 1.25 mm.

FIG. 14 is a view of the second curved extending section 45 (a distal portion of the curved extending section 40) seen from a direction of an arrow XIV of FIG. 12, and is a view of the second curved extending section 45 seen from one side of the thickness direction. Furthermore, FIG. 15 is a view of the second curved extending section 45 seen from the first width direction side. Further, FIG. 16 is a cross-sectional view along the XVI-XVI line of FIG. 12, and shows a cross section perpendicular to an extending direction of the second curved extending section 45. Here, the direction of the arrow XIV matches a direction of rotating as much as an acute angle θ5 from the distal side toward the second intersecting direction side in the projection from the first width direction. The acute angle θ5 is, for example, 75°.

As shown in FIG. 12 to FIG. 16, cutting surfaces (treating surfaces) 47 to 49 are disposed in the second curved extending section 45. A first cutting surface 47 is disposed on the second curved outer surface 56 (a region of an outer surface of the curved extending section 40 which faces the second intersecting direction side). Further, a second cutting surface 48 is provided on the third curved outer surface 57 (a region of the outer surface of the curved extending section 40 which is directed on the first width direction side), and a third cutting surface 49 is disposed on the fourth curved outer surface 58 (a region of the outer surface of the curved extending section 40 which faces the second width direction side). After-mentioned grooves are formed in each of the abrading surfaces 47 to 49. Furthermore, each of the cutting surfaces 47 to 49 extends from a distal end (the distal surface 46) of the curved extending section 40 toward the proximal side. The first cutting surface 47 is provided in the second curved extending section 45 and on the second curved outer surface 56. Consequently, in the projection from each of the first width direction and the second width direction, the first abrading surface 47 is formed into a circular shape in which the center (O1) is positioned on the first intersecting direction side with respect to the curved extending section 40.

The second curved extending section 45 has a thickness dimension T6 between the first cutting surface 47 and the first curved outer surface 55 in the thickness direction of the curved extending section 40. The thickness dimension T6 between the first abrading surface 47 and the first curved outer surface 55 is about the same size as the thickness dimension T2. Furthermore, the second curved extending section 45 has a width dimension W5 between the second cutting surface 48 (the third curved outer surface 57) and the third cutting surface 49 (the fourth curved outer surface 58) in the first width direction and the second width direction. The width dimension W5 between the second abrading surface 48 and the third abrading surface 49 is about the same size as the width dimension W1. Consequently, in a range in which the first cutting surface 47 extends (the second curved extending section 45), the thickness dimension T6 (T2) between the first cutting surface 47 and the first curved outer surface 55 in the thickness direction of the curved extending section 40 is smaller than the width dimension W5 (W1) between the third curved outer surface 57 and the fourth curved outer surface 58 in the first width direction and the second width direction.

In the second cutting surface 48, a plurality of (five in the present embodiment) extending grooves (first extending grooves) 63A to 63E are formed. Each of the extending grooves 63A to 63E extends substantially perpendicularly to the extending direction of the curved extending section 40, and extends along the thickness direction of the curved extending section 40 in the present embodiment. Furthermore, the extending grooves 63A to 63E are lined in parallel in the extending direction of the curved extending section 40, and each of the extending grooves 63A to 63E has a space q1 between the extending groove and the adjacent extending groove (corresponding one or two of the grooves 63A to 63E) in the extending direction of the curved extending section 40. Furthermore, the most distal extending groove 63A positioned most distally among the extending grooves 63A to 63E is stipulated. The second curved extending section 45 has an extending dimension L17 from the distal end of the ultrasonic probe 8 to the most distal extending groove 63A in the extending direction of the curved extending section 40. In the certain example, the space q1 is 0.9 mm and the extending dimension L17 is 0.45 mm.

Furthermore, when there is stipulated the reference plane (the second reference plane) Y2 passing along the longitudinal axis C and perpendicularly to the first width direction and the second width direction, a bottom position of each of the extending grooves 63A to 63E is disposed as much as a width direction distance W2 away from the reference plane Y2 in the first width direction. In the certain example, the width direction distance W2 is 1.1 mm. Furthermore, when seen from one side of the thickness direction (a first cutting surface 47 side), each of the extending grooves (the first extending grooves) 63A to 63E has a semicircular shape formed by a semicircular portion of a circle having a diameter φ1. In the certain example, the diameter φ1 is 0.5 mm.

In the third cutting surface 49, a plurality of (five in the present embodiment) extending grooves (second extending grooves) 65A to 65E are formed. Each of the extending grooves 65A to 65E is substantially symmetric with the corresponding extending groove (corresponding one of the grooves 63A to 63E) about the reference plane Y2 which is the central plane. Consequently, similarly to the extending grooves (the first extending grooves) 63A to 63E, each of the extending grooves 65A to 65E extends along the thickness direction of the curved extending section 40, and the space q1, the extending dimension L17, the width direction distance W2 and the diameter φ1 are stipulated in connection with the extending grooves (the second extending grooves) 65A to 65E.

Furthermore, the first cutting surface 47 is different in extending pattern of the grooves from the second cutting surface 48 and the third cutting surface 49. In the first cutting surface 47, there are formed a plurality of (five in the present embodiment) inclined grooves (first inclined grooves) 66A to 66E and a plurality of (five in the present embodiment) inclined grooves (second inclined grooves) 67A to 67E. Each of the inclined grooves 66A to 66E extends in a state of inclining as much as an acute angle (a first acute angle) 86 relative to the extending direction of the curved extending section 40. That is, each of the inclined grooves (the first inclined grooves) 66A to 66E inclines relative to the longitudinal axis direction in projection from the first cutting surface 47 side. Here, in the projection from the first abrading surface 47 side, one side of an extending direction of each of the inclined grooves 66A to 66E matches a direction of rotating as much as the acute angle θ6 from the proximal side toward the second width direction side. Furthermore, each of the inclined grooves 67A to 67E extends in a state of inclining as much as an acute angle (a second acute angle) θ7 relative to the extending direction of the curved extending section 40. That is, each of the inclined grooves (the second inclined grooves) 67A to 67E inclines relative to the longitudinal axis direction toward a side opposite to the inclined grooves (the first inclined grooves) 66A to 66E in the projection from the first-cutting surface 47 side. Here, in the projection from the first cutting surface 47 side, one side of the extending direction of each of the inclined grooves 67A to 67E matches a direction of rotating as much as the acute angle θ7 from the proximal side toward the first width direction side. On the first abrading surface 47, each of the inclined grooves 66A to 66E intersects the corresponding inclined groove (corresponding one of the grooves 67A to 67E), and forms a meshed structure (crosshatch structure). In the certain example, the acute angle (the first acute angle) θ6 and the acute angle (the second acute angle) θ7 are 45° or more and 65° or less, and are preferably about 60°.

Each of the inclined grooves (the first inclined grooves) 66A to 66E has a space q2 between the inclined groove and the inclined groove (corresponding two or one of the grooves 66A to 66E) that is adjacent (in a direction perpendicular to the extending direction of the inclined grooves 66A to 66E). Furthermore, there is stipulated the reference inclined groove (a first reference inclined groove) 66C positioned third distally in the inclined grooves 66A to 66E.

The second curved extending section 45 has an extending dimension L18 from the distal end of the ultrasonic probe 8 to a distal position of the reference inclined groove 66C in the extending direction of the curved extending section 40. In the certain example, the space q2 is 0.8 mm and the extending dimension L18 is 2.25 mm. Furthermore, each of the inclined grooves 66A to 66E has a depth T4 and a width 42. Furthermore, a bottom surface of each of the inclined grooves 66A to 66E seen from a second cutting surface 48 side (one side of the width direction) is formed into a circular shape of a radius φ2/2. In the certain example, the depth T4 of each of the inclined grooves 66A to 66E is 0.35 mm and the width φ2 is 0.35 mm.

Each of the inclined grooves (the second inclined grooves) 67A to 67E is substantially symmetric with the corresponding first inclined groove (corresponding one of the grooves 66A to 66E) about the reference plane Y2 which is the central plane. Consequently, similarly to the inclined grooves 66A to 66E, the space q2, the extending dimension L18, the depth T4 and the width φ2 are stipulated in connection with the inclined grooves 67A to 67E.

Furthermore, each of the extending grooves (the first extending grooves) 63A to 63E and each of the extending grooves (the second extending grooves) 65A to 65E match a position of an intersecting portion of the corresponding inclined groove (corresponding one of the grooves 66A to 66E) and the corresponding inclined groove (corresponding one of the grooves 67A to 67E) in the longitudinal axis direction. For example, the respective extending grooves 63C and 65C match a position of an intersecting portion of the inclined groove (the first inclined groove) 66C and the inclined groove (the second inclined groove) 67C in the longitudinal axis direction.

In the cross section of the second curved extending section 45 which is perpendicular to the extending direction, there is formed into a curved surface of a corner radius R6 each of a portion between the first curved outer surface 55 (a region of an outer surface which faces the first intersecting direction side) and the second cutting surface 48 and a portion between the first curved outer surface 55 and the third cutting surface 49. Furthermore, in the cross section of the second curved extending section 45 which is perpendicular to the extending direction, there is formed into a curved surface of a corner radius R7 each of a portion between the first cutting surface 47 and the second cutting surface 48 and a portion between the first cutting surface 47 and the third cutting surface 49. In the certain example, the corner radius R6 is 0.5 mm and the corner radius R7 is 0.9 mm.

The curved surface portion of the corner radius R6 is formed along the range S1 of FIG. 3 in the longitudinal axis direction, and the curved surface portion of the corner radius R7 is formed along the range S2 of FIG. 3 in the longitudinal axis direction. That is, the curved surface portion of the corner radius R6 and the curved surface portion of the corner radius R7 extend from the distal end of the ultrasonic probe 8 to the tapered section 41 in the longitudinal axis direction, and the curved surface portion of the corner radius R6 and the curved surface portion of the corner radius R7 are formed in a projecting portion (an exposed portion) of the ultrasonic probe 8 from the distal end of the sheath 7. Consequently, in a part of the tapered section 41 and the curved extending section 40, in the cross section perpendicular to the extending direction, there is formed into the curved surface of the corner radius R6 in each of a portion between a region of an outer surface which faces the first intersecting direction side and a region of an outer surface which faces the first width direction side and a portion between the region of the outer surface which faces the first intersecting direction side and a region of the outer surface which faces the second width direction side. Further, in the part of the tapered section 41 and the curved extending section 40, in the cross section perpendicular to the extending direction, there is formed into the curved surface of the corner radius R7 in each of a portion between a region of the outer surface which is directed on the second intersecting direction side and the region of the outer surface which is directed on the first width direction side and a portion between the region of the outer surface which is directed on the second intersecting direction side and the region of the outer surface which is directed on the second width direction side.

Figure 17:
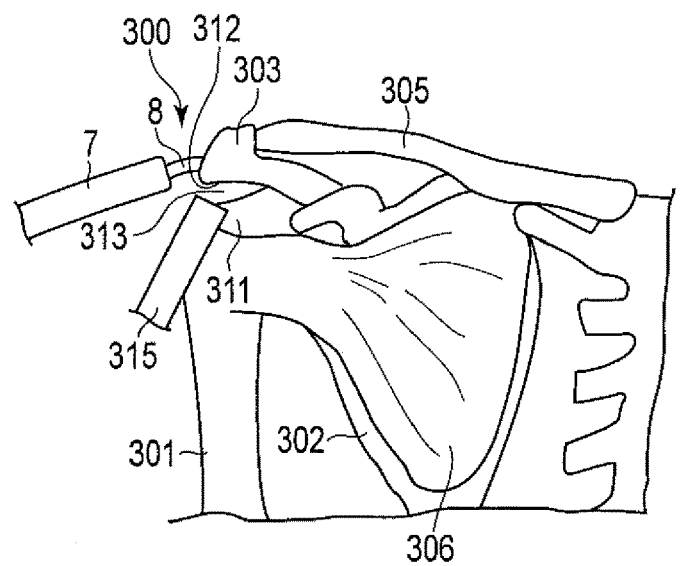
FIG. 17 is a schematic view of a state where a bone is cut in a shoulder joint by use of an ultrasonic treatment device according to the third embodiment, which is seen from a front side of the shoulder joint.
Figure 18:
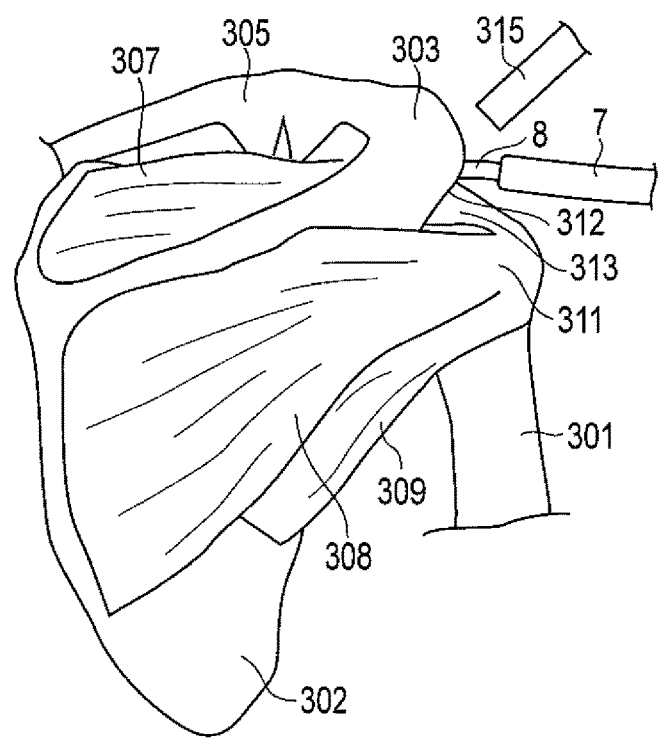
FIG. 18 is a schematic view of a state where the bone is cut in the shoulder joint by use of the ultrasonic treatment device according to the third embodiment, which is seen from a rear side of the shoulder joint.

Next, a function and an effect of the ultrasonic probe 8 of the present embodiment will be described. FIG. 17 and FIG. 18 are views showing a state where a bone is cut in a shoulder joint 300 by use of an ultrasonic treatment system 1. FIG. 17 is a view of the shoulder joint 300 seen from a front side (a chest side), and FIG. 18 is a view of the shoulder joint 300 seen from a rear side (a back side). As shown in FIG. 17 and FIG. 18, the shoulder joint 300 is a joint between a humerus 301 and a scapula 302. The scapula 302 includes an acromion 303. The acromion 303 is coupled with a clavicle 305. From the scapula 302, there origin a subscapularis muscle 306, a supraspinatus muscle 307, an infraspinatus muscle 308 and a teres minor muscle 309. On a lower side of the acromion 303, a rotator cuff 311 is formed as a tendon of the subscapularis muscle 306, the supraspinatus muscle 307, the infraspinatus muscle 308 and the teres minor muscle 309. The humerus 301 extends from the rotator cuff 311. Furthermore, a cavity 313 is formed between a lower surface 312 of the acromion 303 and the rotator cuff 311.

In the present embodiment, a distal portion of a rigid endoscope (an arthroscope) 315 and a distal portion of the ultrasonic probe 8 are inserted into the cavity 313 between the acromion 303 and the rotator cuff 311. Each of the rigid endoscope 315 and the ultrasonic probe 8 is inserted from the outside of a human body into the cavity 313 through one of an insertion area of the front side, an insertion area of a lateral side and an insertion area of the rear side. However, the insertion area of the rigid endoscope 315 is different from the insertion area of the ultrasonic probe 8. In FIG. 17 and FIG. 18, the rigid endoscope 315 is inserted into the cavity 313 from the insertion area of the front side, and the ultrasonic probe 8 is inserted into the cavity 313 through the insertion area of the lateral side. Further, in the cavity 313 under observation with the rigid endoscope 315, one of the cutting surfaces 47 to 49 of the ultrasonic probe 8 is brought into contact with the lower surface 312 of the acromion 303. The ultrasonic vibration is transmitted to the cutting surfaces 47 to 49 in a state where the one of the abrading surfaces 47 to 49 is in contact with the lower surface 312 of the acromion 303, whereby cutting of a bone spur (a bone) is performed in the lower surface 312 of the acromion 303. It is to be noted that the abrading of the bone spur in the lower surface 312 of the acromion 303 is performed in a state where the second curved extending section 45 is immersed in a liquid (physiological saline).

FIG. 19 and FIG. 20 are views showing a state where the first cutting surface 47 of the second curved extending section 45 of the ultrasonic probe 8 is in contact with the lower surface 312 of the acromion 303. In FIG. 20, the first cutting surface 47 is brought into contact with a position different from that of FIG. 19 in the lower surface 312 of the acromion 303. Here, in the ultrasonic probe 8, the first curved extending section 42 curves toward a first perpendicular direction side relative to the probe main body section 31 extending along the longitudinal axis C, and the second curved extending section 45 curves further toward the first perpendicular direction side relative to the first curved extending section 42. Further, in the second curved extending section 45, an acute angle relative to the longitudinal axis direction increases toward the distal side, and in the second curved extending section 45 and the second curved outer surface 56, the first cutting surface 47 is disposed. Consequently, in the present embodiment, in the projection from each of the first width direction and the second width direction, the first cutting surface 47 is formed into the circular shape in which the center (O1) is positioned on the first intersecting direction side with respect to the curved extending section 40. The cavity 313 between the acromion 303 and the rotator cuff 311 is narrow, and the lower surface 312 of the acromion 303 is formed into a curved surface. The first curved extending section 42 and the second curved extending section 45 are formed as described above, so that the first cutting surface 47 can appropriately be brought into contact with the lower surface 312 of the acromion 303 which is formed into the curved surface.

For example, in FIG. 19 and FIG. 20, the positions which come in contact with the first cutting surface 47 are different from each other in the lower surface 312 of the acromion 303, and hence a contact angle of the first abrading surface 47 with the lower surface 312 of the acromion 303 varies. In the present embodiment, the first curved extending section 42 and the second curved extending section 45 are formed as described above, and hence even when the contact angle of the first cutting surface 47 with the lower surface 312 of the acromion 303 changes, it is possible to appropriately bring the first cutting surface 47 into contact with the lower surface 312 of the acromion 303. For example, in each of FIG. 19 and FIG. 20, the first cutting surface 47 appropriately comes in contact with the lower surface 312 of the acromion 303. That is, at any position of the lower surface 312 of the acromion 303 (i.e., even when the contact angle of the first cutting surface 47 with the lower surface 312 of the acromion 303 is any angle), the first cutting surface 47 can appropriately be brought into contact with the lower surface 312 of the acromion 303.

Furthermore, in the present embodiment, the first cutting surface 47 is provided on the second curved outer surface 56 of the curved extending section 40, and on the second curved outer surface 56 (a region of an outer peripheral surface of the curved extending section 40 which faces the second intersecting direction side), the acute angle θ4 of the tangent line at the distal end relative to the longitudinal axis direction is 10° or more and 30° or less (preferably 20° or more and 25° or less). By setting the acute angle θ4 to be 10° or more and 30° or less (especially 20° or more and 25° or less), the first cutting surface 47 has a shape corresponding to the lower surface 312 of the acromion 303, and at any position of the lower surface 312 of the acromion 303, the first cutting surface 47 can further easily and appropriately be brought into contact with the lower surface 312 of the acromion 303.

Furthermore, in the first cutting surface 47, each of the inclined grooves (the first inclined grooves) 66A to 66E intersects the corresponding second inclined groove (corresponding one of the grooves 67A to 67E), and the crosshatch structure is formed. The crosshatch structure is formed on the first cutting surface 47, and hence by longitudinally vibrating the second curved extending section 45 by the ultrasonic vibration in a state where the first cutting surface 47 is in contact with the bone, the bone (the bone spur) is appropriately cut. That is, it is possible to appropriately cut the hard bone. Furthermore, in the present embodiment, the acute angle θ6 of each of the inclined grooves (the first inclined grooves) 66A to 66E relative to the extending direction of the ultrasonic probe 8 (i.e., a vibrating direction by the longitudinal vibration) and the acute angle θ7 of each of the inclined grooves (the second inclined grooves) 67A to 67E relative to the extending direction of the ultrasonic probe 8 (i.e., the vibrating direction by the longitudinal vibration) are 45° or more and 65° or less. Thus, each of the acute angles θ6 and θ7 is in the above-mentioned range, so that cutting properties of the bone improve in a case where the lower surface 312 of the acromion 303 is cut with the first cutting surface 47 by use of the ultrasonic vibration.

In the present embodiment, the bone may be cut by bringing the second cutting surface 48 or the third cutting surface 49 into contact with the lower surface 312 of the acromion 303. Furthermore, in a case where the first cutting surface 47 is brought into contact with the lower surface 312 of the acromion 303 to cut the bone (the bone spur), the bone is cut by the second cutting surface 48 and the third cutting surface 49 in the vicinity of an area to be cut by the first cutting surface 47. Thus, the bone is cut by the cutting surface 48 or 49, thereby preventing only the area cut by the first cutting surface 47 from being concaved and preventing a stepped area from being formed on the lower surface 312 of the acromion 303.

Furthermore, the extending grooves 63A to 63E of the second cutting surface 48 and the extending grooves 65A to 65E of the third cutting surface 49 extend substantially perpendicularly (along the thickness direction of the curved extending section 40) to the extending direction of the ultrasonic probe 8 (i.e., the vibrating direction by the longitudinal vibration). The extending grooves (the first extending grooves) 63A to 63E extend substantially perpendicularly to the vibrating direction by the longitudinal vibration, and hence the cutting properties of the bone improve in a case where the bone is cut with the second cutting surface 48 by use of the ultrasonic vibration. Similarly, the extending grooves (the second extending grooves) 65A to 65E extend substantially perpendicularly to the vibrating direction by the longitudinal vibration, and hence the cutting properties of the bone improve in a case where the bone is cut with the third cutting surface 49 by use of the ultrasonic vibration.

Furthermore, each of the extending grooves (the first extending grooves) 63A to 63E and each of the extending grooves (the second extending grooves) 65A to 65E match in a position of an intersecting portion of the corresponding inclined groove (corresponding one of the grooves 66A to 66E) and the corresponding inclined groove (corresponding one of the grooves 67A to 67E) in the longitudinal axis direction. The extending grooves 63A to 63E and 65A to 65E and the inclined grooves 66A to 66E and 67A to 67E are arranged as described above, so that when the bone is cut with the cutting surfaces 47 to 49, the bone is evenly and uniformly cut and the cutting properties further improve.

Furthermore, in the present embodiment, the distal end of the first narrowed outer surface 51 (the first narrowing end position E10) is positioned on the proximal side with respect to the distal end of the second narrowed outer surface 52 (the second narrowing end position E11), and the extending dimension L19 of the first axis parallel outer surface 61 is larger than the extending dimension L20 of the second axis parallel outer surface 62. Consequently, in a case where the first cutting surface 47 moves to a position to be contactable with the lower surface 312 of the acromion 303, the region of the outer surface which faces the first intersecting direction side (the back-surface-side region) in the curved extending section 40, the tapered section 41 and the relay extending section 43 is hard to come in contact with a biological tissue or the like other than a treated target (the lower surface of the acromion 303). Therefore, the first cutting surface 47 is easily movable to the position at which the surface can come in contact with the lower surface 312 of the acromion 303.

Furthermore, in the present embodiment, in the state where the vibrating body unit 20 longitudinally vibrates in the established frequency range, the tapered section 41 is positioned on the distal side with respect to the most distal side vibration node N3, and an amplitude V of the longitudinal vibration is enlarged in the tapered section 41. For example, the longitudinal vibration in which the amplitude at the vibration antinode is 80 μm is enlarged to the longitudinal vibration in which the amplitude at the vibration antinode is 140 μm or more and 150 μm or less by the tapered section 41. Furthermore, stress σ due to the ultrasonic vibration increases at the vibration node and in a portion in which a sectional area perpendicular to a transmitting direction of the ultrasonic vibration decreases, and the stress becomes zero at the vibration antinode. Therefore, in the present embodiment, the stress σ increases between the vibration node N3 and the distal end (E13) of the tapered section 41 (see FIG. 7).

Here, in the present embodiment, the dimension of the tapered section 41 from the proximal end (E9) to the distal end (E13) in the longitudinal axis direction is larger than the ⅛ wavelength (λ/8) in the state where the vibrating body unit 20 longitudinally vibrates in the established frequency range. Further, in the tapered section 41, the first narrowing dimension L12 between the proximal end (E9) and the first narrowing end position E10 in the longitudinal axis direction is also larger than the ⅛ wavelength in the state where the vibrating body unit 20 longitudinally vibrates in the established frequency range. The dimension of the tapered section 41 from the proximal end (E9) to the distal end (E13) in the longitudinal axis direction increases, so that the stress σ due to the ultrasonic vibration is kept to be substantially constant along the total length between the vibration node N3 and the distal end (E13) of the tapered section 41. That is, between the vibration node N3 and the distal end (E13) of the tapered section 41, the stress is effectively prevented from locally increasing (i.e., generation of a peak is prevented). For example, in the certain example, even when the longitudinal vibration in which the amplitude at the vibration antinode increases (e.g., 80 μm) is transmitted to the proximal end (E9) of the tapered section 41, the stress σ is kept to be substantially uniform at about 300 MPa between the vibration node N3 and the distal end (E13) of the tapered section 41 in the state where the vibrating body unit 20 longitudinally vibrates in the established frequency range (e.g., 46 kHz or more and 48 kHz or less). That is, in the present embodiment, the stress is prevented from locally increasing to about 700 MPa (e.g., at the distal end (E13) of the tapered section 41) between the vibration node N3 and the distal end (E13) of the tapered section 41. The stress σ is prevented from locally increasing, and hence breakage of the ultrasonic probe 8 due to the ultrasonic vibration can effectively be prevented.

Furthermore, in the present embodiment, the cross section gravity center in the cross section perpendicular to the longitudinal axis C shifts from the longitudinal axis C toward the second intersecting direction side in the tapered section 41 and the relay extending section 43. Especially, between the first narrowing end position E10 and the first curve start position (the curve proximal end) E14, there increases the shift of the cross section gravity center relative to the longitudinal axis C on the second intersecting direction side. Consequently, in the present embodiment, shift of the center of gravity onto the first intersecting direction side which is caused by the curve of the curved extending section 40 relative to the longitudinal axis direction is canceled by the shift of the center of gravity onto the second intersecting direction side which is caused by the tapered section 41 and the relay extending section 43. Consequently, in the state where the ultrasonic vibration of the ultrasonic probe 8 is transmitted toward the distal side, it is possible to decrease generation of irregular vibration (transverse vibration or torsional vibration) except the longitudinal vibration.

In the present embodiment, in the projection from the first width direction (one side of the width direction), the portion between the first curved outer surface 55 and the distal surface 46 is formed into the curved surface of the corner radius R3. Furthermore, in the projection from the first width direction, the portion between the second curved outer surface 56 and the distal surface 46 is formed into the curved surface of the corner radius R4. Further, in the projection from the second intersecting direction (one side of the intersecting direction), each of the portion between the third curved outer surface 57 and the distal surface 46 and the portion between the fourth curved outer surface 58 and the distal surface 46 is formed into the curved surface of the corner radius R5. Consequently, on the distal surface 46 of the ultrasonic probe 8, there decreases a ratio of the surface (the outer surface) perpendicular to the extending direction of the ultrasonic probe 8 (i.e., the vibrating direction of the longitudinal vibration). The ratio of the surface perpendicular to the vibrating direction of the longitudinal vibration decreases, so that even when the ultrasonic probe 8 longitudinally vibrates in the state where the second curved extending section 45 is immersed into the liquid (physiological saline), generation of cavitation in the vicinity of the distal surface 46 is decreased. Due to the decrease of the generation of the cavitation, visibility of an operator in a treatment improves.

Furthermore, in the projecting portion (the exposed portion) of the ultrasonic probe 8 from the distal end of the sheath 7, in the cross section perpendicular to the extending direction, there is formed into the curved surface of the corner radius R6 in each of the portion between the region of the outer surface which faces the first intersecting direction side and the region of the outer surface which faces the first width direction side and the portion between the region of the outer surface which faces the first intersecting direction side and the region of the outer surface which faces the second width direction side. Further, in the projecting portion (the exposed portion) of the ultrasonic probe 8 from the distal end of the sheath 7, in the cross section perpendicular to the extending direction, there is formed into the curved surface of the corner radius R7 in each of the portion between the region of the outer surface which faces the second intersecting direction side and the region of the outer surface which faces the first width direction side and the portion between the region of the outer surface which faces the second intersecting direction side and the region of the outer surface which faces the second width direction side. Consequently, on the outer peripheral surface of the tapered section 41, the relay extending section 43 and the curve extending section 40, any edges are not formed. Therefore, even when the projecting portion (the exposed portion) of the ultrasonic probe 8 from the distal end of the sheath 7 comes in contact with the biological tissue or the like other than the treated target, it is possible to effectively prevent damages on the biological tissue.

Fourth Embodiment

Next, a fourth embodiment of the present invention will be described with reference to FIG. 21 to FIG. 24. In the fourth embodiment, the constitution of the third embodiment is modified as follows. It is to be noted that the same components as in the third embodiment are denoted with the same reference signs to omit their descriptions.

Also in the present embodiment, similarly to the third embodiment, an ultrasonic probe 8 includes a probe main body section 31, a tapered section 41 and a curved extending section 40 (a first curved extending section 42 and a second curved extending section 45). Further, the probe main body section 31 includes a horn portion 35, a horn portion 36, a sectional area increasing portion 37 and a supported portion 38 in the same manner as in the first embodiment. In a certain example, it is preferable that a total length L1 of the ultrasonic probe 8 is 183.4 mm. Furthermore, in the certain example, it is preferable that a longitudinal dimension L2 from a distal end of the ultrasonic probe 8 to an abutment surface 33 (a proximal end of the probe main body section 31) in a longitudinal axis direction is 177.5 mm.

Furthermore, in the certain example of the present embodiment, it is preferable that a longitudinal dimension L3 from the abutment surface 33 to a proximal end (a vibration input end) E1 of the horn portion 35 in the longitudinal axis direction is 29 mm. Furthermore, it is preferable that a horn longitudinal dimension (a first horn longitudinal dimension) L4 of the horn portion (a first horn portion) 35 from the proximal end (the vibration input end) E1 to a distal end (a vibration output end) E2 in the longitudinal axis direction is 20 mm. Also in the present embodiment, in the horn portion 35, an outer diameter of the probe main body section 31 decreases from an outer diameter D1 to an outer diameter D2 toward a distal side. In the certain example, it is preferable that the outer diameter D1 is 7 mm. Further, it is preferable that the outer diameter D2 is 3.8 mm.

Furthermore, in the certain example of the present embodiment, it is preferable that a longitudinal dimension L5 from the abutment surface 33 to a proximal end (a vibration input end) E3 of the horn portion 36 in the longitudinal axis direction is 88.1 mm. Further, it is preferable that a horn longitudinal dimension (a second horn longitudinal dimension) L6 of the horn portion (a second horn portion) 36 from the proximal end (the vibration input end) E3 to a distal end (a vibration output end) E4 in the longitudinal axis direction is 14 mm. Also in the present embodiment, in the horn portion 36, the outer diameter of the probe main body section 31 decreases from the outer diameter D2 to an outer diameter D3 toward the distal side. In the certain example, it is preferable that the outer diameter D3 is 2.7 mm.

In the certain example of the present embodiment, it is preferable that a longitudinal dimension L7 from the abutment surface 33 to a distal end (a vibration output end) E6 of the sectional area increasing portion 37 in the longitudinal axis direction is 116.7 mm. Furthermore, there decreases an extending dimension L8 of the sectional area increasing portion 37 from a proximal end (a vibration input end) E5 to the distal end (the vibration output end) E6 in the longitudinal axis direction. Also in the present embodiment, in the sectional area increasing portion 37, the outer diameter of the probe main body section 31 increases from the outer diameter D3 to an outer diameter D4 toward the distal side. In the certain example, the outer diameter D4 is about the same as the outer diameter D2 at the proximal end E3 of the horn portion 36.

In the certain example of the present embodiment, it is preferable that a longitudinal dimension L9 from the distal end E6 of the sectional area increasing portion 37 to a proximal end E7 of the supported portion 38 in the longitudinal axis direction is 24.1 mm. Furthermore, in the supported portion 38, it is preferable that an extending dimension L10 from the proximal end E7 to a distal end E8 in the longitudinal axis direction is 3 mm. Further, in the supported portion 38, an outer diameter decreases from the outer diameter D4 to an outer diameter D5 in a proximal portion, and an outer diameter increases from the outer diameter D5 to an outer diameter D6 in a distal portion. In the certain example, the outer diameter D5 is slightly (about 0.4 mm) smaller than the outer diameter D4. Further, it is preferable that the outer diameter D6 is about the same as the outer diameter D4 and is 3.8 mm.

Furthermore, in a state where a vibrating body unit 20 longitudinally vibrates in an established frequency range (46 kHz or more and 48 kHz or less), a vibration node N1 is positioned at the proximal end E1 of the horn portion 35 or in the vicinity of the proximal end E1, and a vibration node N2 is positioned at the proximal end E3 of the horn portion 36 or in the vicinity of the proximal end E3. Furthermore, in the state where the vibrating body unit 20 longitudinally vibrates in the predetermined frequency range, a vibration antinode A3 is positioned in the sectional area increasing portion 37, and a vibration antinode (a most distal vibration antinode) A2 is positioned at the distal end of the ultrasonic probe 8. Further, in the state where the vibrating body unit 20 longitudinally vibrates in the established frequency range, a vibration node (a most distal vibration node) N3 that is one of vibration nodes of the longitudinal vibration is positioned in the supported portion 38. According to the above-mentioned constitution, also in the certain example of the present embodiment, in a case where the longitudinal vibration in which an amplitude at the vibration antinode is 18 μm is transmitted to the proximal end (the abutment surface 33) of the probe main body section 31, the longitudinal vibration in which the amplitude at the vibration antinode is 80 μm occurs at a distal end E9 of the probe main body section 31.

Figure 21:
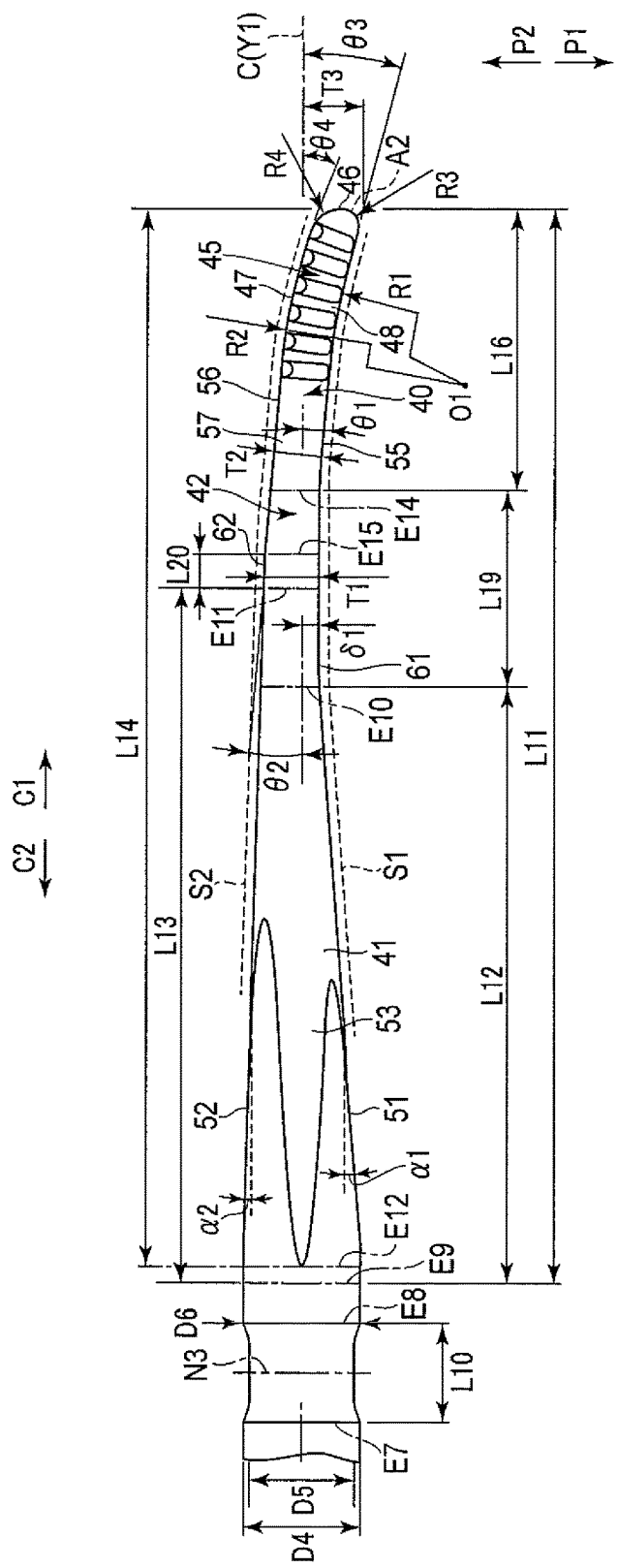
FIG. 21 is a schematic view of a distal portion of an ultrasonic probe according to a fourth embodiment seen from a first width direction side.
Figure 22:
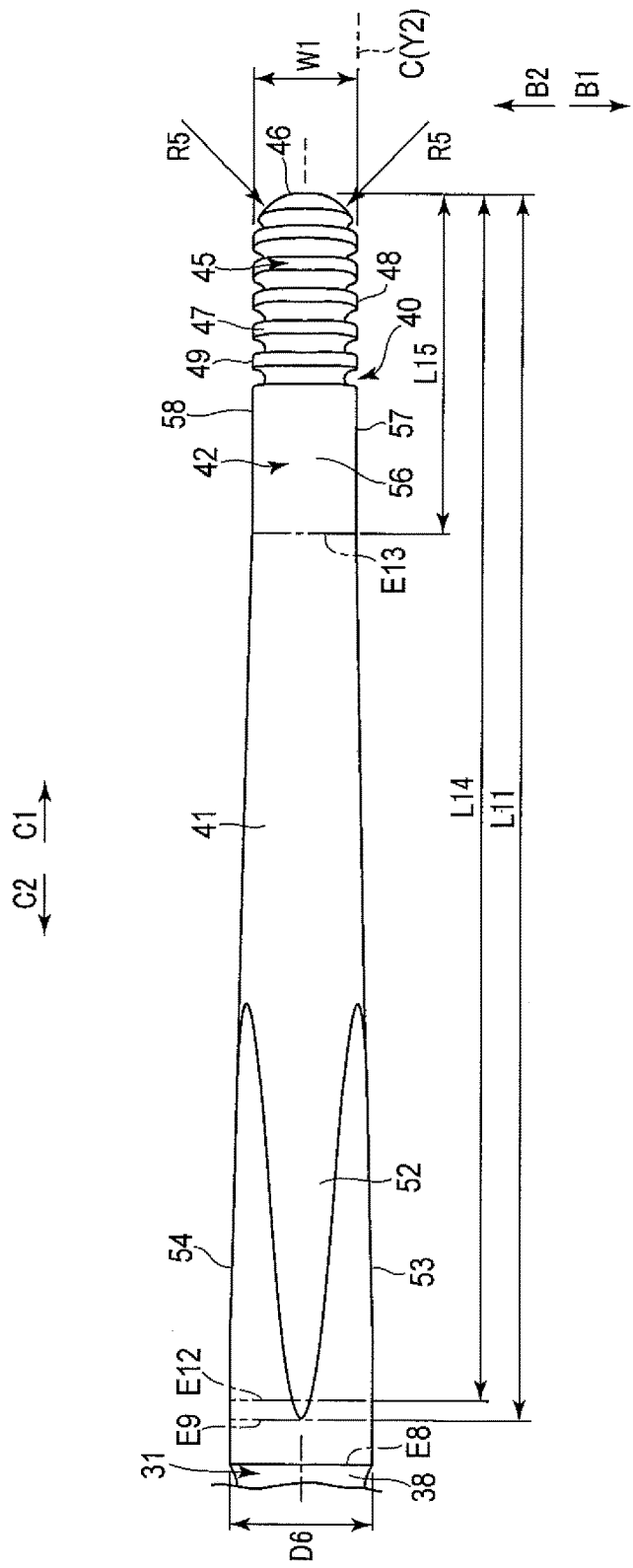
FIG. 22 is a schematic view of the distal portion of the ultrasonic probe according to the fourth embodiment seen from a second intersecting direction side.

FIG. 21 and FIG. 22 are views showing a constitution of a distal portion of the ultrasonic probe 8. FIG. 21 is a view of the ultrasonic probe 8 seen from a first width direction side, and FIG. 22 is a view of the ultrasonic probe 8 seen from a second intersecting direction side. It is to be noted that in FIG. 21, a range shown by a broken line S1 and a broken line S2 projects from a distal end of a sheath 7 toward the distal side.

As shown in FIG. 21 and FIG. 22, also in the present embodiment, the distal end E9 of the probe main body section 31 is positioned on the distal side with respect to the distal end E8 of the supported portion 38. Further, in the certain example, a distance between the distal end E8 of the supported portion 38 and the distal end of the probe main body section 31 in the longitudinal axis direction is about 1.2 mm. Furthermore, the distal end E9 of the probe main body section 31 is continuous with a proximal end of the tapered section 41. In the certain example of the present embodiment, it is preferable that a longitudinal dimension L11 from the distal end of the ultrasonic probe 8 to the proximal end (E9) of the tapered section 41 in the longitudinal axis direction is 32.5 mm.

Also in the present embodiment, the tapered section 41 includes a first narrowed outer surface 51 facing a first intersecting direction side, and in the tapered section 41, a distance (a first distance) δ from a longitudinal axis C to the first narrowed outer surface 51 in a first intersecting direction decreases from a proximal side toward the distal side between the proximal end (E9) and a first narrowing end position (a first distance decreasing end position) E10 in the longitudinal axis direction. In the certain example, it is preferable that a first narrowing dimension L12 of the tapered section 41 between the proximal end (E9) and the first constricting end position E10 in the longitudinal axis direction is 18 mm. Furthermore, also in the present embodiment, the tapered section 41 includes a second narrowed outer surface 52 facing the second intersecting direction side. In the tapered section 41, a distance (a second distance) δ' from the longitudinal axis C to the second narrowed outer surface 52 in a second intersecting direction decreases from the proximal side toward the distal side between the proximal end (E9) and a second narrowing end position (a second distance decreasing end position) E11 in the longitudinal axis direction. As compared with the second narrowing end position E11 (a distal end of the second constricted outer surface 52), the first narrowing end position E10 (a distal end of the first constricted outer surface 51) is positioned on a proximal side. In the certain example, it is preferable that a second narrowing dimension L13 between the proximal end (E9) of the tapered section 41 and the second narrowing end position E11 in the longitudinal axis direction is 21 mm. Due to the above-mentioned constitution, also in the tapered section 41 of the present embodiment, a thickness (a dimension) T of the ultrasonic probe 8 in the first intersecting direction and the second intersecting direction decreases toward the distal side between the proximal end (a thickness decreasing start position) of the tapered section 41 and the second narrowing end position (a thickness decreasing end position) E11 in the longitudinal axis direction. Furthermore, also in the present embodiment, in projection from a first width direction (one side of a width direction), a first narrowing angle α1 that is a narrowing angle (an acute angle) of the first narrowed outer surface 51 relative to the longitudinal axis direction is larger than a second narrowing angle α2 that is a narrowing angle (an acute angle) of the second narrowed outer surface 52 relative to the longitudinal axis direction, and the first constricting angle is different from the second constricting angle α2.

Also in the present embodiment, the tapered section 41 includes a third narrowed outer surface 53 facing the first width direction, and a fourth narrowed outer surface 54 facing a second width direction. Further, in the tapered section 41, a width (a dimension) W of the ultrasonic probe 8 in the first width direction and the second width direction decreases toward the distal side, between a width decreasing start position E12 and a width decreasing end position E13 in the longitudinal axis direction. Further, the width decreasing end position E13 becomes a distal end of each of the third narrowed outer surface 53 and the fourth narrowed outer surface 54, and becomes a distal end of the tapered section 41. In the certain example, it is preferable that a longitudinal dimension L14 from the distal end of the ultrasonic probe 8 to the width decreasing start position E12 in the longitudinal axis direction is 32 mm. Further, the width decreasing start position E12 is positioned on the distal side with respect to the proximal end (E9) of the tapered section 41 slightly (by about 0.5 mm). Furthermore, in the certain example, it is preferable that a longitudinal dimension L15 from the distal end of the ultrasonic probe 8 to the width decreasing end position E13 in the longitudinal axis direction is 9 mm. Further, the width decreasing end position E13 is positioned on the distal side with respect to the second narrowing end position E11 by about 2 mm.

A distance (a first distance) 61 from the longitudinal axis C to the first narrowed outer surface 51 (an outer peripheral surface of the ultrasonic probe 8) toward the first intersecting direction at the first narrowing end position E10 is smaller than a value of ½ of the outer diameter D6 at the distal end E9 of the probe main body section 31, and in the certain example, the distance 61 is 0.45 mm or more and 0.5 mm or less. Furthermore, a thickness T1 of the ultrasonic probe 8 in the first intersecting direction and the second intersecting direction at the second narrowing end position E11 is smaller than the outer diameter D6 at the distal end E9 of the probe main body section 31, and in the certain example, it is preferable that the thickness T1 is 1.7 mm. Further, at the width decreasing end position E13, a width W1 of the ultrasonic probe 8 in the first width direction and the second width direction is smaller than the outer diameter D6 of the probe main body section 31 at the distal end E9, and in the certain example, it is preferable that the width W1 is 2.8 mm.

The tapered section 41 is constituted as described above, and hence in the tapered section 41, a sectional area perpendicular to the longitudinal axis C decreases toward the distal side. Further, in the state where the vibrating body unit 20 longitudinally vibrates in the established frequency range (e.g., 46 kHz or more and 48 kHz or less), the vibration node (the most distal vibration node) N3 is positioned in the vicinity of the proximal end (E9) of the tapered section 41, and each of the vibration antinodes of the longitudinal vibration is positioned away from the tapered section 41 in the longitudinal axis direction. Consequently, in the tapered section 41 in which the sectional area decreases toward the distal side, the amplitude of the longitudinal vibration (ultrasonic vibration) is enlarged. In the certain example, in a case where the longitudinal vibration in which the amplitude at the vibration antinode is 80 µm is transmitted to the proximal end (E9) of the tapered section 41, the longitudinal vibration of an amplitude of 140 µm to 150 µm occurs at the distal end of the probe.

Furthermore, also in the present embodiment, the ⅛ wavelength ($\lambda/8$) in the state where the vibrating body unit 20 longitudinally vibrates in the established frequency range is small as compared with a dimension from the proximal end (E9) to the distal end (E13) of the tapered section 41 in the longitudinal axis direction. Furthermore, in the tapered section 41, the first narrowing dimension L12 between the proximal end (E9) and the first narrowing end position E10 in the longitudinal axis direction is larger than the ⅛ wavelength in the state where the vibrating body unit 20 longitudinally vibrates at 46 kHz or more and 48 kHz or less (the predetermined frequency range). It is to be noted that the first narrowing end position E10 is positioned most proximally among the positions (e.g., E10, E11 and E13) at each of which the narrowing ends on the outer peripheral surface (the narrowed outer surfaces 51 to 54) of the tapered section 41.

Also in the present embodiment, the curved extending section 40 including the first curved extending section 42 and the second curved extending section 45 extends in a state of curving relative to the probe main body section 31 (i.e., the longitudinal axis C) toward the first intersecting direction side. Further, the curved extending section 40 includes a first curved outer surface 55 facing the first intersecting direction side (the side toward which the curved extending section 40 curves), and in projection from the first width direction (one side of the width direction), a region of the first curved outer surface 55 located on the distal side with respect to a first curve start position E14 curves relative to the longitudinal axis direction (the probe main body section 31) toward the first intersecting direction side. Furthermore, the curved extending section 40 includes a second curved outer surface 56 facing the second intersecting direction side (a side opposite to the side on which the curved extending section 40 curves), and in the projection from the first width direction, a region of the second curved outer surface 56 located on the distal side with respect to a second curve start position E15 curves relative to the longitudinal axis direction toward the first intersecting direction side. That is, the first curved outer surface 55 starts curving relative to the longitudinal axis C in the first intersecting direction side at the first curve start position E14, and the second curved outer surface 56 starts curving relative to the longitudinal axis C in the first intersecting direction side at the second curve start position E15. Furthermore, also in the present embodiment, the curved extending section 40 includes a third curved outer surface 57 fading the first width direction side, and a fourth curved outer surface 58 directed on the second width direction side.

In the present embodiment, the first curve start position E14 is positioned on the distal side with respect to the second curve start position E15. Therefore, the curved extending section 40 extends from the second curve start position E15 which is a proximal end (a curve proximal end) toward the distal side. The ultrasonic probe 8 has a longitudinal dimension L16 from the distal end to the first curve start position E14 in the longitudinal axis direction. The longitudinal dimension L16 is smaller than the longitudinal dimension L15 from the distal end of the ultrasonic probe 8 to the width decreasing end position E13 in the longitudinal axis direction. Consequently, the first curve start position E14 is positioned on the distal side with respect to the width decreasing end position E13. In the certain example, the longitudinal dimension L16 is 8.5 mm.

Furthermore, in the present embodiment, the second curve start position (the curve proximal end) E15 is positioned on the proximal side with respect to the first curve start position E14, and positioned on the proximal side with respect to the width decreasing end position E13. Therefore, in the present embodiment, the proximal end (E15) of the curved extending section 40 is positioned on the proximal side with respect to the distal end (E13) of the tapered section 41. Consequently, in the present embodiment, a part of the tapered section 41 is formed by a part of the curved extending section 40 (the first curved extending section 42). Here, in the certain example, a dimension between the second curve start position (the curve proximal end) E15 and the width decreasing end position E13 in the longitudinal axis direction is about 1 mm, and a dimension between the width decreasing end position E13 and the first curve start position E14 in the longitudinal axis direction is about 0.5 mm.

Also in the present embodiment, a first axis parallel outer surface 61 facing the first intersecting direction is continuous between the first narrowed outer surface 51 and the first curved outer surface 55 in the longitudinal axis direction. The first axis parallel outer surface 61 extends in parallel (substantially parallel) with the longitudinal axis C between the first narrowing end position E10 and the first curve start position E14. Further, the first axis parallel outer surface 61 has an extending dimension (a first extending dimension) L19 in the longitudinal axis direction. On the first axis parallel outer surface 61, the distance δ from the longitudinal axis C toward the first intersecting direction is kept to be substantially constant at the distance δ1 from the first narrowing end position E10 to the first curve start position E14. Furthermore, also in the present embodiment, a second axis parallel outer surface 62 facing the second intersecting direction is continuous between the second narrowed outer surface 52 and the second curved outer surface 56 in the longitudinal axis direction. The second axis parallel outer surface 62 extends in parallel (substantially parallel) with the longitudinal axis C between the second narrowing end position E11 and the second curve start position E15. Further, the second axis parallel outer surface 62 has an extending dimension (a second extending dimension) L20 in the longitudinal axis direction. The extending dimension L19 of the first axis parallel outer surface 61 is larger than the extending dimension L20 of the second axis parallel outer surface 62. On the second axis parallel outer surface 62, a distance δ' from the longitudinal axis C in the second intersecting direction is kept to be substantially constant from the second constricting end position E11 to the second curve start position E15.

Due to such a constitution as described above, the thickness T of the ultrasonic probe 8 in the first intersecting direction and the second intersecting direction is kept to be substantially constant at the thickness T1 between the second narrowing end position E11 and the second curve start position E15 in the longitudinal axis direction. Furthermore, the width W of the ultrasonic probe 8 (the curved extending section 40) in the first width direction and the second width direction is kept to be substantially constant at the width W1 between the width decreasing end position E13 and the distal end of the ultrasonic probe 8 in the longitudinal axis direction.

Also in the present embodiment, in a distal portion of the tapered section 41, the distance (the first distance) δ1 from the longitudinal axis C to the outer peripheral surface of the ultrasonic probe 8 in the first intersecting direction is smaller than a value of ½ of the thickness T1 of the ultrasonic probe 8 in the first intersecting direction and the second intersecting direction. Consequently, in a case where there is stipulated a reference plane (a first reference plane) Y1 passing along the longitudinal axis C and perpendicularly to the first intersecting direction and the second intersecting direction, the ultrasonic probe 8 is nonsymmetrical about the reference plane Y1 which is a central plane in the tapered section 41. Further, in the tapered section 41, a cross section gravity center in a cross section perpendicular to the longitudinal axis C shifts from the longitudinal axis C toward the second intersecting direction side. Especially, between the first narrowing end position E10 and the second curve start position (a curve proximal end) E15, there increases the shift of the cross section gravity center relative to the longitudinal axis C in the second intersecting direction side. Furthermore, in a case where there is stipulated a reference plane (a second reference plane) Y2 passing along the longitudinal axis C and perpendicularly to the first width direction and the second width direction, the ultrasonic probe 8 is substantially symmetric about the reference plane Y2 which is a central plane in the tapered section 41.

In projection from the first width direction (one side of the width direction), in a region of an outer peripheral surface of the first curved extending section 42 which is directed on the first intersecting direction side, a tangent line at the first curve start position E14 has an acute angle δ1 relative to the longitudinal axis direction. Furthermore, in the projection from the first width direction, in a region of the outer peripheral surface of the first curved extending section 42 which faces the second intersecting direction side, a tangent line at the second curve start position (the curve proximal end) E15 has an acute angle δ2 relative to the longitudinal axis direction. The acute angle θ1 and the acute angle θ2 are larger than 0° and 10° or less, and in the certain example, the acute angle θ1 is 5° and the acute angle θ2 is 5°.

Also in the present embodiment, the second curved extending section 45 is continuous with the distal side of the first curved extending section 42, and the second curved extending section 45 extends in a state of curving relative to the first curved extending section 42 toward the first intersecting direction side. In the projection from the first width direction (one side of the width direction), a region of an outer peripheral surface of the second curved extending section 45 which faces the first intersecting direction side extends in a circular shape of a radius R1, and a region of the outer peripheral surface of the second curved extending section 45 which faces the second intersecting direction side extends in a circular shape of a radius R2. Further, a center O1 of each of the circle of the radius R1 and the circle of the radius R2 is positioned on the first intersecting direction side with respect to the curved extending section 40 (the ultrasonic probe 8). Consequently, also in the present embodiment, an acute angle of the second curved extending section 45 relative to the longitudinal axis direction increases toward the distal side.

In a region of the outer peripheral surface of the second curved extending section 45 which is directed on the first intersecting direction side, a tangent line at a distal end has an acute angle θ3 relative to the longitudinal axis direction, and in a region of the outer peripheral surface of the second curved extending section 45 which faces the second intersecting direction side, a tangent line at a distal end has an acute angle θ4 relative to the longitudinal axis direction. That is, at a distal end of the first curved outer surface 55, the curved extending section 40 has the acute angle θ3 relative to the longitudinal axis direction. Further, at a distal end of the second curved outer surface 56, the curved extending section 40 has the acute angle θ4 relative to the longitudinal axis direction. In the certain example, the radius R1 is 15 mm and the acute angle θ3 is 15°. Furthermore, in the certain example, the radius R2 is 16.5 mm and the acute angle θ4 is 200. Also in the present embodiment, similarly to the first embodiment, in the second curved outer surface 56 (a region of the outer peripheral surface of the second curved extending section 45 which faces a second perpendicular direction side), the acute angle θ4 of the tangent line at the distal end relative to the longitudinal axis direction is 10° or more and 30° or less, and more preferably 20° or more and 25° or less.

Furthermore, when a thickness direction of the ultrasonic probe 8 is stipulated in the same manner as in the first embodiment, in the present embodiment, the ultrasonic probe 8 is kept to be substantially constant at a thickness dimension T2 in the thickness direction, from the first curve start position E14 to the distal end in the longitudinal axis direction. That is, between the first curve start position E14 and the distal end of the ultrasonic probe 8, the thickness dimension T2 that is a distance between the first curved outer surface 55 and the second curved outer surface 56 is kept to be substantially constant. In the certain example, the thickness dimension T2 is 1.5 mm. Therefore, the acute angles θ1 to θ4 and the radiuses R1 and R2 are determined in a state where the thickness dimension T2 of the ultrasonic probe 8 is substantially constant from the first curve start position E14 to the distal end. Furthermore, also in the present embodiment, the region of the outer peripheral surface of the second curved extending section 45 which faces the first intersecting direction side has a separation distance T3 from the longitudinal axis C in the first intersecting direction at the distal end. In the certain example, it is preferable that the separation distance T3 is 1.9 mm.

Furthermore, also in the present embodiment, in the projection from the first width direction (the one side of the width direction), a portion between the first curved outer surface 55 and a distal surface 46 is formed into a curved surface of a corner radius R3. Furthermore, in the projection from the first width direction, a portion between the second curved outer surface 56 and the distal surface 46 is formed into a curved surface of a corner radius R4. In the certain example, the corner radius R3 is 0.5 mm and the corner radius R4 is 0.9 mm. Furthermore, in projection from the second intersecting direction (one side of the intersecting direction), each of a portion between the third curved outer surface 57 and the distal surface 46 and a portion between the fourth curved outer surface 58 and the distal surface 46 is formed into a curved surface of a corner radius R5. In the certain example, the corner radius R5 is 1.25 mm.

FIG. 23 is a view of the second curved extending section 45 (a distal portion of the curved extending section 40) seen from the first width direction side. Further, FIG. 24 is a cross-sectional view along the XXIV-XXIV line of FIG. 23 and shows a cross section perpendicular to an extending direction of the curved extending section 40. As shown in FIG. 21 to FIG. 24, also in the present embodiment, the second curved extending section 45 includes cutting surfaces 47 to 49 in the same manner as in the first embodiment. The first cutting surface 47 is disposed in the second curved extending section 45 and on the second curved outer surface 56. Further, in projection from each of the first width direction and the second width direction, the first abrading surface 47 is formed into a circular shape in which the center (O1) is positioned on the first intersecting direction side with respect to the curved extending section 40. Furthermore, the second cutting surface 48 is provided on the third curved outer surface 57, and the third cutting surface 49 is provided on the fourth curved outer surface 58.

The second curved extending section 45 has a thickness dimension T6 in a thickness direction of the curved extending section 40 between the first cutting surface 47 and the first curved outer surface 55, and the thickness dimension T6 is about the same size as the thickness dimension T2. Furthermore, the second curved extending section 45 has a width dimension W5 in the first width direction and the second width direction between the second cutting surface 48 (the third curved outer surface 57) and the third cutting surface 49 (the fourth curved outer surface 58), and the width dimension W5 is about the same size as the width dimension W1. Consequently, in a range in which the first abrading surface 47 extends (the second curved extending section 45), the thickness dimension T6 (T2) between the first cutting surface 47 and the first curved outer surface 55 in the thickness direction of the curved extending section 40 is smaller than the width dimension W5 (W1) between the third curved outer surface 57 and the fourth curved outer surface 58 in the first width direction and the second width direction.

Also in the present embodiment, on the second cutting surface 48, a plurality of (six in the present embodiment) extending grooves (first extending grooves) 63A to 63F are formed, and on the third cutting surface 49, a plurality of (six in the present embodiment) extending grooves (second extending grooves) 65A to 65F are formed. Each of the extending grooves 63A to 63F extends substantially perpendicularly to the extending direction of the curved extending section 40, and extends along the thickness direction of the curved extending section 40 in the present embodiment. Furthermore, the extending grooves 63A to 63F are rowed in parallel in the extending direction of the curved extending section 40. Each of the extending grooves 63A to 63F has an acute angle γ1 between the extending groove and the extending groove (corresponding one or two of the grooves 63A to 63F) disposed adjacent in the extending direction of the curved extending section 40. That is, the extending direction of each of the extending grooves 63A to 63F shifts as much as the acute angle γ1 from the extending direction of the adjacent extending groove (corresponding one or two of the grooves 63A to 63F). Furthermore, there is stipulated the most proximal extending groove 63F positioned most proximally among the extending grooves 63A to 63F. The extending direction of the most proximal extending groove 63F has an obtuse angle θ8 relative to the proximal side. In the certain example, the acute angle γ1 is 30 and the obtuse angle θ8 is 950. The extending grooves (first extending grooves) 63A to 63F extend as described above, and hence in the projection from the first width direction, the extending grooves 63A to 63F are extended on the second cutting surface 48 perpendicularly to the circular first cutting surface 47 in which the center (O1) is positioned on the first intersecting direction side with respect to the curved extending section 40. Therefore, in the present embodiment, in the projection from the first width direction, each of the extending grooves 63A to 63F forms an angle α3 between the extending groove and the first cutting surface 47, and the angle α3 is 90°. Further, the extending grooves 63A to 63F intersect at the center (O1) of the circle of the first cutting surface 47. Each of the extending grooves 63A to 63F has a width φ3 and a depth W3. In the certain example, the width φ3 is 0.5 mm and the depth W3 is 0.35 mm.

Each of the extending grooves (the second extending grooves) 65A to 65F is substantially symmetric with the corresponding extending groove (corresponding one of the grooves 63A to 63F) about the reference plane Y2 which is the central plane. Consequently, in the projection from the second width direction, the extending grooves 65A to 65F are extended on the third cutting surface 49 perpendicularly to the circular first cutting surface 47 in which the center is positioned on the first intersecting direction side with respect to the curved extending section 40. Furthermore, the acute angle γ1, the obtuse angle θ8, the width φ3 and the depth W3 are stipulated in connection with the extending grooves 65A to 65F in the same manner as in the extending grooves 63A to 63F. Furthermore, the second curved extending section 45 has a width direction dimension W4 in the first width direction and the second width direction from a bottom position of each of the extending grooves 63A to 63F to a bottom position of the corresponding extending groove (corresponding one of the grooves 65A to 65F). In the certain example, the width direction dimension W4 is 2.1 mm or more and 2.15 mm or less.

Furthermore, a plurality of (six in the present embodiment) relay groves 71A to 71F are formed on the first cutting surface 47. Each of the relay groves 71A to 71F extends substantially perpendicularly to the extending direction of the curved extending section 40, and the respective grooves are extended along the width directions (the first width direction and the second width direction) of the curved extending section 40 in the present embodiment. One end of each of the relay groves 71A to 71F is continuous with the corresponding extending groove (corresponding one of the grooves 63A to 63F), and the other end of each of the relay groves 71A to 71F is continuous with the corresponding extending groove (corresponding one of the grooves 65A to 65F). Each of the relay groves 71A to 71F has the same width ϕ3 as in the extending grooves 63A to 63F and 65A to 65F, and has a depth T5. In the certain example, the depth T5 is 0.3 mm or more and 0.35 mm or less. Furthermore, a bottom surface of each of the relay groves 71A to 71F seen from a second cutting surface 48 side (one side of the width direction) is formed into a circular shape of a radius ϕ3/2.

In a cross section of the second curved extending section 45 which is perpendicular to the extending direction, there is formed into a curved surface of a corner radius R6 in each of a portion between the first curved outer surface 55 (a region of the outer surface which faces a first perpendicular direction side) and the second cutting surface 48 and a portion between the first curved outer surface 55 and the third cutting surface 49. Furthermore, in the cross section of the second curved extending section 45 which is perpendicular to the extending direction, each of a portion between the first cutting surface 47 and the second cutting surface 48 and a portion between the first cutting surface 47 and the third cutting surface 49 is formed into a curved surface of a corner radius R7. In the certain example, the corner radius R6 is 0.5 mm and the corner radius R7 is 0.9 mm. The curved surface portion of the corner radius R6 is formed along the range S1 of FIG. 3 in the longitudinal axis direction, and the curved surface portion of the corner radius R7 is formed along the range S2 of FIG. 3 in the longitudinal axis direction. That is, also in the present embodiment, the curved surface portion of the corner radius R6 and the curved surface portion of the corner radius R7 extend from the distal end of the ultrasonic probe to the tapered section 41 in the longitudinal axis direction, and the curved surface portion of the corner radius R6 and the curved surface portion of the corner radius R7 are formed in a projecting portion (an exposed portion) of the ultrasonic probe 8 from the distal end of the sheath 7.

Also in the present embodiment, in the cross section of the second curved extending section 45 which is perpendicular to the extending direction, there is formed into a curved surface of a corner radius R8 in each of a portion between each of the relay groves 71A to 71F and the corresponding extending groove (corresponding one of the grooves 63A to 63F) and a portion between each of the relay groves 71A to 71F and the corresponding extending groove (corresponding one of the grooves 65A to 65F). In the certain example, the corner radius R8 is 0.55 mm.

Due to such a constitution as described above, also in the present embodiment, a function and an effect similar to those of the third embodiment are produced.

Furthermore, in the present embodiment, the relay groves 71A to 71F extend substantially perpendicularly to the extending direction of the curved extending section 40 (i.e., a vibrating direction by longitudinal vibration). The relay groves 71A to 71F extend substantially perpendicularly to the vibrating direction by the longitudinal vibration, and hence when a bone is cut with the first cutting surface 47 by use of the ultrasonic vibration, cutting properties of the bone improve.

Furthermore, each of the relay groves 71A to 71F is continuous with the corresponding extending groove (corresponding one of the grooves 63A to 63F) and the corresponding extending groove (corresponding one of the grooves 65A to 65F). Consequently, when the bone is cut with the cutting surfaces 47 to 49, the bone is evenly and uniformly cut, and the cutting properties further improve.

Furthermore, the extending grooves (the first extending grooves) 63A to 63F are extended perpendicularly to the circular first cutting surface 47 on the second cutting surface 48, and the extending grooves (the second extending grooves) 65A to 65F are extended perpendicularly to the circular first cutting surface 47 on the third cutting surface 49. Consequently, when the bone is cut with the second cutting surface 48 or the third cutting surface 49, the cutting properties of the bone improve.

Furthermore, in the present embodiment, there is formed into the curved surface of the corner radius R8 in each of the portion between each of the relay groves 71A to 71F and the corresponding extending groove (corresponding one of the grooves 63A to 63F) and the portion between each of the relay groves 71A to 71F and the corresponding extending groove (corresponding one of the grooves 65A to 65F). Consequently, the bone is effectively prevented from being left uncut between each of the relay groves 71A to 71F and the corresponding extending groove (corresponding one of the grooves 63A to 63F) and between each of the relay groves 71A to 71F and the corresponding extending groove (corresponding one of the grooves 65A to 65F).

Furthermore, in the present embodiment, the first curve start position E14 of the first curved outer surface 55 is positioned on the distal side with respect to the second curve start position E15 of the second curved outer surface 56. Consequently, when the first cutting surface 47 moves to a position to be contactable with a lower surface 312 of an acromion 303, a region of the outer surface which faces the first intersecting direction side (the back-surface-side region) is further hard to come in contact with a biological tissue or the like other than a treated target (the lower surface of the acromion 303) in the curved extending section 40 and the tapered section 41. Therefore, the first cutting surface 47 is further easily moved to the position to be contactable with the lower surface 312 of the acromion 303.

Modification

In the above-mentioned embodiments or the like, an ultrasonic probe (8) includes a probe main body section (31) which is extended along a longitudinal axis (C), and which is configured to vibrate in an established frequency range in a state where an ultrasonic vibration is transmitted from a proximal side toward a distal side; and a tapered section (101; 41) which is provided on the distal side with respect to the probe main body section (31), and in which a sectional area perpendicular to the longitudinal axis (C) decreases from the proximal side toward the distal side, the tapered section being configured to vibrate together with the probe main body section (31) in the established frequency range in a state where the ultrasonic vibration is transmitted from the probe main body section (31). In the state where the probe main body section (31) and the tapered section (101; 41) vibrate in the established frequency range, a most distal vibration node (N3) positioned most distally among the vibration nodes is positioned on the proximal side with respect to a proximal end (E9) of the tapered section (101; 41), and a ⅛ wavelength (λ/8) of the vibration is smaller than a taper dimension from the proximal end (E9) of the tapered section (101; 41) to a distal end (S5; E13) of the tapered section (101; 41) in a longitudinal axis direction.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An ultrasonic probe comprising:
a probe main body section which is extended along a longitudinal axis, and which is configured to vibrate in an established frequency range when an ultrasonic vibration is transmitted from a proximal side toward a distal side of the probe main body section; and
a tapered section which is provided on the distal side of the probe main body section, and in which a sectional area perpendicular to the longitudinal axis decreases from a proximal end toward a distal end, the tapered section being configured to vibrate with the probe main body section in the established frequency range when the ultrasonic vibration is transmitted from the probe main body section; and
a curved extending section which is provided on the distal end of the tapered section, and which curves relative to the probe main body section and the tapered section toward a first intersecting direction that intersects the longitudinal axis, the curved extending section being configured to vibrate with the probe main body section and the tapered section in the established frequency range when the ultrasonic vibration is transmitted from the probe main body section through the tapered section;
wherein:
when the probe main body section and the tapered section vibrate in the established frequency range, a most distal vibration node positioned most distally among vibration nodes is positioned on a proximal side of the proximal end of the tapered section, and a ⅛ wavelength of the vibration is smaller than a taper dimension from the proximal end of the tapered section to the distal end of the tapered section in a longitudinal axis direction,
the curved extending section includes:
a first curved outer surface facing the first intersecting direction;
a second curved outer surface facing a second intersecting direction that is opposite to the first intersecting direction,
a third curved outer surface facing a first width direction side, when two directions which intersect the longitudinal axis and are perpendicular to the first intersecting direction and the second intersecting direction are defined as a first width direction and a second width direction; and
a fourth curved outer surface facing a second width direction side,
the second curved outer surface includes a first cutting surface on which grooves are formed, and which is configured to cut a treated target,
the third curved outer surface includes a second cutting surface on which grooves are formed, and which is configured to cut the treated target, and
the fourth curved outer surface includes a third cutting surface on which grooves are formed, and which is configured to cut a treated target.
2. The ultrasonic probe of claim 1,
wherein in projection from each of the first width direction and the second width direction, the first cutting surface is formed into a circular shape in which a center is positioned on the first intersecting direction with respect to the curved extending section.
3. The ultrasonic probe of claim 1,
wherein the second cutting surface and the third cutting surface are different from the first cutting surface in extending pattern of the grooves.
4. The ultrasonic probe of claim 1, wherein
the second cutting surface includes first extending grooves extended along a thickness direction of the curved extending section,
the third cutting surface includes second extending grooves extended along the thickness direction of the curved extending section, and
the first cutting surface includes relay grooves in each of which one end is continuous with the first extending grooves and the other end is continuous with the second extending grooves.
5. An ultrasonic probe comprising:
a probe main body section which is extended along a longitudinal axis, and which is configured to vibrate in an established frequency range when an ultrasonic vibration is transmitted from a proximal side toward a distal side of the probe main body section;
a tapered section which is provided on the distal side of the probe main body section, and in which a sectional area perpendicular to the longitudinal axis decreases from a proximal end toward a distal end, the tapered section being configured to vibrate with the probe main body section in the established frequency range when the ultrasonic vibration is transmitted from the probe main body section; and
a curved extending section which is provided on the distal end of the tapered section, and which curves relative to the probe main body section and the tapered section toward a first intersecting direction that intersects the longitudinal axis, the curved extending section being configured to vibrate with the probe main body section and the tapered section in the established frequency range when the ultrasonic vibration is transmitted from the probe main body section through the tapered section,
wherein:
when the probe main body section and the tapered section vibrate in the established frequency range, a most distal vibration node positioned most distally among vibration nodes is positioned on a proximal side of the proximal end of the tapered section, and a ⅛ wavelength of the vibration is smaller than a taper dimension from the proximal end of the tapered section to the distal end of the tapered section in a longitudinal axis direction,
the curved extending section includes:
a first curved outer surface facing the first intersecting direction;
a second curved outer surface facing a second intersecting direction that is opposite to the first intersecting direction;
a first cutting surface that is formed of grooves on the second curved outer surface, and which is configured to cut a treated target;
a third curved outer surface facing a first width direction side, when two directions which intersect the longitudinal axis and are perpendicular to the first intersecting direction and the second intersecting direction are defined as a first width direction and a second width direction; and a fourth curved outer surface facing a second width direction side, and in a range in which the first cutting surface extends, a thickness dimension between the first cutting surface and the first curved outer surface in a thickness direction of the curved extending section is smaller than a width dimension between the third curved outer surface and the fourth curved outer surface in the first width direction and the second width direction.

6. The ultrasonic probe of claim 5, wherein in projection from each of the first width direction and the second width direction, the first cutting surface is formed into a circular shape in which a center is positioned on the first intersecting direction side with respect to the curved extending section.

7. An ultrasonic probe comprising:

a probe main body section which is extended along a longitudinal axis, and which is configured to vibrate in an established frequency range when an ultrasonic vibration is transmitted from a proximal side toward a distal side of the probe main body section;

a tapered section which is provided on the distal side of the probe main body section, and in which a sectional area perpendicular to the longitudinal axis decreases from a proximal end toward a distal end, the tapered section being configured to vibrate with the probe main body section in the established frequency range when the ultrasonic vibration is transmitted from the probe main body section; and a curved extending section which is provided on the distal end of the tapered section, and which curves relative to the probe main body section and the tapered section toward a first intersecting direction that intersects the longitudinal axis, the curved extending section being configured to vibrate with the probe main body section and the tapered section in the established frequency range when the ultrasonic vibration is transmitted from the probe main body section through the tapered section, wherein:

when the probe main body section and the tapered section vibrate in the established frequency range, a most distal vibration node positioned most distally among vibration nodes is positioned on a proximal side of the proximal end of the tapered section, and a ⅛ wavelength of the vibration is smaller than a taper dimension from the proximal end of the tapered section to the distal end of the tapered section in a longitudinal axis direction, the curved extending section includes a first curved outer surface facing the first intersecting direction, and a second curved outer surface facing a second intersecting direction that is opposite to the first intersecting direction, the tapered section includes:
a first narrowed outer surface which faces the first intersecting direction, and on which a first distance from the longitudinal axis in the first intersecting direction decreases from the proximal end toward the distal end; and a second narrowed outer surface which faces the second intersecting direction side, and on which a second distance from the longitudinal axis in the second intersecting direction decreases from the proximal end toward the distal end, and the ultrasonic probe further comprises:
a first axis parallel outer surface that faces the first intersecting direction, and that is continuous between the first narrowed outer surface and the first curved outer surface in the longitudinal axis direction, the first axis parallel outer surface being extended in parallel with the longitudinal axis; and a second axis parallel outer surface that faces the second intersecting direction, and that is continuous between the second narrowed outer surface and the second curved outer surface in the longitudinal axis direction, the second axis parallel outer surface being extended in parallel with the longitudinal axis.

8. The ultrasonic probe of claim 7, wherein a first extending dimension of the first axis parallel outer surface in the longitudinal axis direction is larger than a second extending dimension of the second axis parallel outer surface in the longitudinal axis direction.

* * * * *